(12) United States Patent
Doronina et al.

(10) Patent No.: US 11,510,959 B2
(45) Date of Patent: Nov. 29, 2022

(54) HYDROPHILIC ANTIBODY-DRUG CONJUGATES

(71) Applicant: Seagen Inc., Bothell, WA (US)

(72) Inventors: Svetlana Doronina, Snohomish, WA (US); Robert Lyon, Sammamish, WA (US); Peter Senter, Seattle, WA (US)

(73) Assignee: Seagen Inc., Bothell, WA (US)

( * ) Notice: Subject to any disclaimer, the term of this patent is extended or adjusted under 35 U.S.C. 154(b) by 0 days.

(21) Appl. No.: 17/160,225

(22) Filed: Jan. 27, 2021

(65) Prior Publication Data

US 2021/0283210 A1   Sep. 16, 2021

Related U.S. Application Data

(62) Division of application No. 15/118,031, filed as application No. PCT/US2015/016185 on Feb. 17, 2015, now Pat. No. 10,933,112.

(60) Provisional application No. 61/947,368, filed on Mar. 3, 2014, provisional application No. 61/940,759, filed on Feb. 17, 2014.

(51) Int. Cl.
| | |
|---|---|
| *A61K 38/05* | (2006.01) |
| *A61K 47/68* | (2017.01) |
| *A61K 9/00* | (2006.01) |

(52) U.S. Cl.
CPC .......... *A61K 38/05* (2013.01); *A61K 9/0019* (2013.01); *A61K 47/6803* (2017.08); *A61K 47/6861* (2017.08); *A61K 47/6867* (2017.08); *A61K 47/6889* (2017.08)

(58) Field of Classification Search
None
See application file for complete search history.

(56) References Cited

U.S. PATENT DOCUMENTS

| | | |
|---|---|---|
| 8,664,407 B2 | 3/2014 | Chen |
| 10,933,112 B2 | 3/2021 | Doronina et al. |
| 2009/0018086 A1 | 1/2009 | Doronina |
| 2012/0141509 A1 | 6/2012 | Doronina |
| 2017/0216391 A1 | 8/2017 | Doronina |

FOREIGN PATENT DOCUMENTS

| | | |
|---|---|---|
| EP | 2832856 A1 | 2/2015 |
| WO | 199819705 A1 | 5/1998 |
| WO | 2007086083 A1 | 8/2007 |
| WO | 2009117531 A1 | 9/2009 |
| WO | 2013147153 A1 | 10/2013 |

OTHER PUBLICATIONS

Doronina, S.O. et al. (Oct. 2008, e-pub, Sep. 20, 2008). "Novel Peptide Linkers for Highly Potent Antibody—Auristain Conjugate," Bioconugate Chem. 19:1960-1963.
Extended European Search Report, dated Oct. 2, 2017, for European Patent Application No. 15748980.8, 9 pages.
Harada, M. et al. (Dec. 31, 2000). "Determinants for the Drug Release From T-0128, Camptothecin Analogue-Carboxymethyl Dextran Conjugate," Journal of Controlled Release 69:399-412.
International Preliminary Report on Patentability, dated Aug. 23, 2016, for PCT Application No. PCT/US2015/16185, filed Feb. 17, 2016, 5 pages.
International Search Report and Written Opinion, dated May 1, 2015, for PCT Application No. PCT/US2015/16185, filed Feb. 17, 2015, 11 pages.
Shiose, Y. et al. (2009, e-pub. Dec. 18, 2008). "Systematic Research of Peptide Spacers Controlling Drug Release From Macromolecular Prodrug System, Carboxymethyldextran Polyalcohol-Peptide-Drug Conjugates," Bioconjugate Chem. 20:60-70.
Extended European Search Report, dated Sep. 30, 2021, for European Patent Application No. 21168364.4, 12 pages.

*Primary Examiner* — Samantha L Shterengarts
(74) *Attorney, Agent, or Firm* — Morrison & Foerster LLP

(57) ABSTRACT

Hydrophilic Linkers, Drug-Linker compounds, Drug-Ligand Conjugate compounds and Ligand-Linkers and methods of making and using the same are provided.

11 Claims, 5 Drawing Sheets

HYDROPHILIC ANTIBODY-DRUG CONJUGATES

This application is a divisional application of U.S. patent application Ser. No. 15/118,031, claiming International Filing Date of Feb. 17, 2015, now issued as U.S. Pat. No. 10,933,112, which is a National Stage Entry of International Application No. PCT/US15/16185, filed on Feb. 17, 2015, which claims priority benefit of U.S. Provisional Patent Application No. 61/940,759, filed Feb. 17, 2014, and U.S. Provisional Patent Application No. 61/947,368, filed Mar. 3, 2014, each of which is incorporated herein in its entirety.

BACKGROUND OF THE INVENTION

A great deal of interest has surrounded the use of monoclonal antibodies (mAbs) for the targeted delivery of cytotoxic agents to cancer cells. The design of antibody drug conjugates, by attaching a cytotoxic agent to an antibody, typically via a linker, involves consideration of a variety of factors. These factors include the identity and location of the chemical group(s) for conjugation of the cytotoxic agent, the mechanism of release of the cytotoxic agent, the structural element(s) (if any) providing release of the agent, and structural modification of the released free agent, if any. In addition, if the cytotoxic agent is to be released after antibody internalization, the structural elements for and mechanism of agent release must be consonant with the intracellular trafficking of the conjugate.

While a number of different drug classes have been evaluated for delivery via antibodies, only a few drug classes have proved sufficiently active as antibody-drug conjugates, while having a suitable toxicity profile, to warrant clinical development. One such class is the auristatins, related to the natural product dolastatin 10. Representative auristatins include MMAE (N-methylvaline-valine-dolaisoleuine-dolaproine-norephedrine) and MMAF (N-methylvaline-valine-dolaisoleuine-dolaproine-phenylalanine).

MMAE is an example of a cytotoxic agent that is active as a free drug, and is highly potent after conjugation to a monoclonal antibody (mAb) and release after internalization into cells. MMAE has been successfully conjugated to a mAb at the N-terminal amino acid of MMAE via a cathepsin B-cleavable peptide-based linker containing maleimidocaproyl-valine-citrulline (mc-vc-) and a self-immolative group, p-aminobenzyl-carbamoyl (PARC), to produce antibody-drug conjugates of the following structure, mAb-(mc-vc-PABC-MMAE)$_p$. (In the preceding formula, p refers to the number of (mc-vc-PARC-MMAE) units per mAb or antibody.) Upon cleavage of the bond between the vc peptide and the self-immolative PABC group, the PABC group releases itself from MMAE, liberating free MMAE.

Another auristatin, MMAF, is less active as a free drug (compared to MMAE), yet is highly potent after conjugation to an antibody, internalization and release into cells. MMAF has been successfully conjugated to a monoclonal, antibody (mAb) at its N-terminal amino acid via a cathepsin B-cleavable peptide-based linker containing maleimidocaproyl-valine-citrulline (mc-vc-) and a self-immolative group p-aminobenzyl-carbamoyl (PABC) to produce antibody-drug conjugates of the structure, mAb-(mc-vc-PABC-MMAF)$_p$. (p refers to the number of (mc-vc-PABC-MMAF) units per mAb or antibody). Upon cleavage of the bond between the peptide and the PABC subunit, the self-immolative PABC group releases itself from MMAF, liberating free MMAF.

MMAF is also active as a non-cleavable conjugate, containing the drug-linker maleimidocaproyl MMAF (mcMMAF). When this conjugate, mAb-(mcMMAF)$_p$, is internalized into cells, the active species released is cys-mcMMAF. Because the linker is non-cleavable, the maleimidocaproyl and a cysteine residue of the antibody remain attached to the N-terminus of MMAF. MMAF was also reported to be active as a C-terminal conjugate, attached at its C-terminal amino acid, phenylalanine, to a peptide-maleimidocaproyl linker. When this conjugate, (MMAF-peptide-mc)$_p$-mAb is internalized into cells, the active species, MMAF, is released following cleavage of the MMAF (phenylalanine)-peptide bond.

In animal models, these MMAE and MMAF conjugates generally exhibited a drug loading-dependent decrease in pharmacokinetic properties. In particular, as the number of drug-linker units attached to each antibody increased, the pharmacokinetics (PK) of the conjugates decreased.

Therefore, another important factor in the design of antibody-drug conjugates is the amount of drug that can be delivered per targeting agent (i.e., the number of cytotoxic agents attached to each targeting agent (e.g., an antibody), referred to as the drug load or drug loading). Historically, assumptions were that higher drugs loads were superior to lower drug loads (e.g., 8-loads vs 4-loads). The rationale was that higher loaded conjugates would deliver more drug (cytotoxic agents) to the targeted cells. This rationale was supported by the observations that conjugates with higher drug loadings were more active against cell lines in vitro. Certain later studies revealed, however, that this assumption was not confirmed in animal models. Conjugates having drug loads of 4 or 8 of certain auristatins were observed to have similar activities in mouse models. See, e.g., Hamblett et al., *Clinical Cancer Res.* 10:7063-70 (2004). Hamblett et al, further reported that the higher loaded ADCs were cleared more quickly from circulation in animal models. This faster clearance suggested a PK liability for higher loaded species as compared to lower loaded species. See Hamblett et al. In addition, higher loaded conjugates had lower MTDs in mice, and as a result had narrower reported therapeutic indices. Id. In contrast, ADCs with a drug loading of 2 at engineered sites in a monoclonal antibody were reported to have the same or better PK properties and therapeutic indices as compared to certain 4-loaded ADCs. For example, see Junutula et al., *Clinical Cancer Res.* 16:4769 (2010). Thus, recent trends are to develop ADCs with low drug loadings.

Alternative approaches to overcome the PK liability of higher loaded ADCs have been to append solubilizing groups to the ADCs. For example, polyethylene glycol polymers or other water soluble polymers have been included in linkers (e.g., between the drug and attachment site of an antibody) in an attempt to overcome PK liabilities. Another approach has been to append drug-polymers to an antibody, where each polymer contains a large number of drugs. These alternatives have not, however, necessarily achieved the desired result. In addition, appending solubilizing groups may increase manufacturing complexity of such conjugates.

There remains a need, therefore, for antibody drug conjugate formats (and more generally for formats for other conjugates), that allow for higher drug loading while maintaining other desirable characteristics of lower loaded conjugates, such as favorable PK properties. Surprisingly, the present invention addresses these needs.

BRIEF SUMMARY OF THE INVENTION

The present invention provides, inter glia, hydrophilic Ligand-Linker-Drug Conjugates. By designing the conjugates to have a hydrophilicity similar to the unconjugated targeting agent (e.g., a ligand such as an antibody), the conjugates retain the ability to provide pharmacokinetic (PK) properties similar to that of the unconjugated targeting agent in vivo. The conjugates can also have higher drug loadings (i.e., higher numbers of hydrophilic drug-linkers per targeting agent), as compared to lower loaded conjugates, while retaining such desirable PK properties and having the same or better activity in viva or example, 4-loaded or 8-loaded conjugates can have the same or better PK properties than their 2 or 4 loaded counterparts, respectively; such 4-loaded or 8-loaded conjugates can have the same or better activity than their 2 or 4 loaded counterparts, respectively.) Thus, targeting agents selected on the basis of certain desirable properties can be conjugated with drug linkers without substantially impairing such desirable properties as PK properties of the targeting agent alone. Also provided are method of making and using such conjugates.

Also provided are Linker Drug Compounds for conjugation to targeting agents (Ligands) and methods of preparing and using such compounds. Further provided are Ligand-Linker Compounds to which Drug Compounds can be attached as well as methods of preparing and using such. Compounds.

ABBREVIATIONS AND DEFINITIONS

Figure 1:
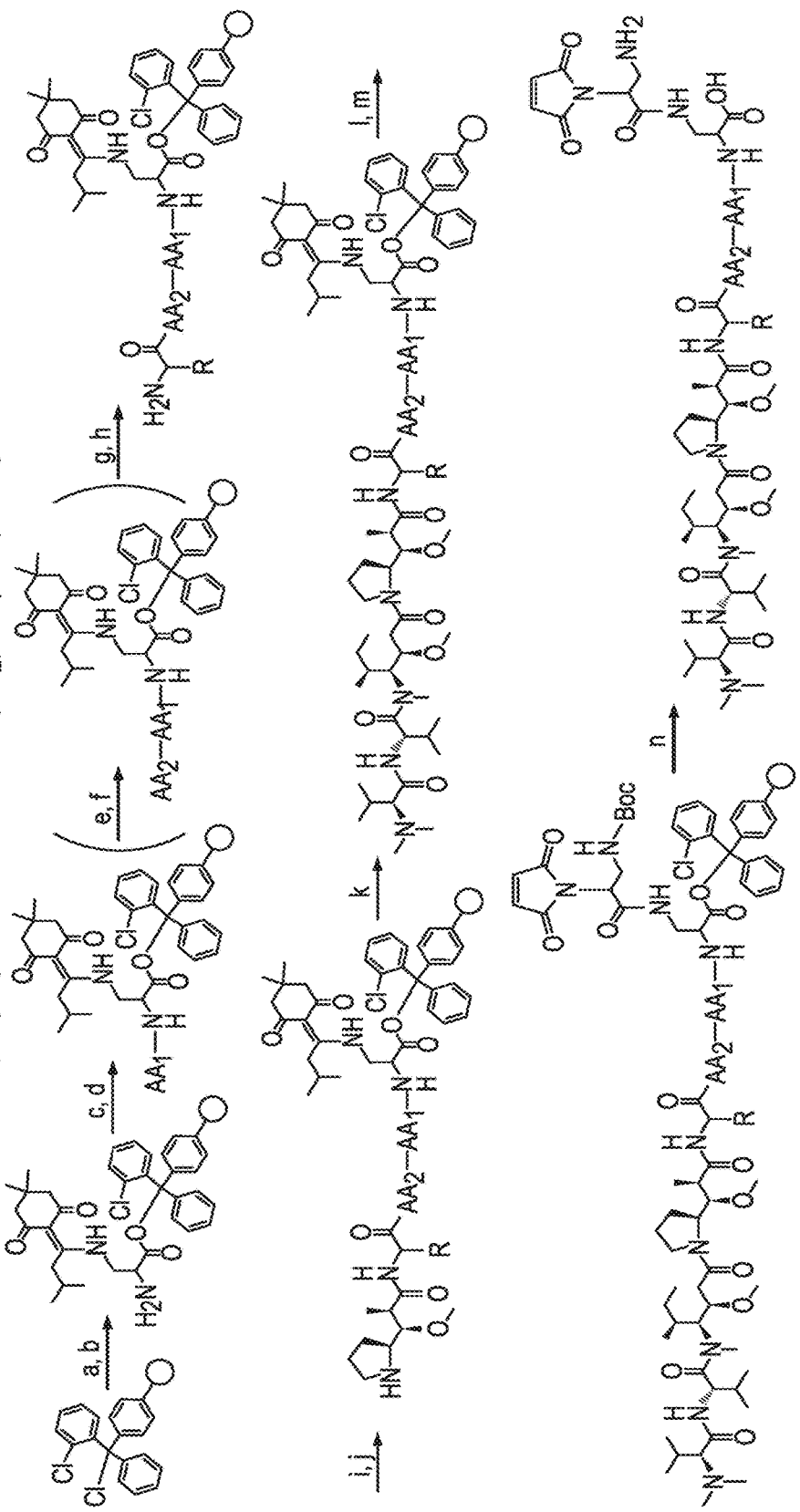
FIG. 1 depicts an exemplary synthetic scheme for assembly of the Ligand-Linker-Drug conjugates described herein.

Unless stated otherwise, the following terms and phrases as used herein are intended to have the following meanings. When trade names are used herein, the trade name includes the product formulation, the generic drug, and the active pharmaceutical ingredient(s) of the trade name product, unless otherwise indicated by context.

The term "hydrophilicity index" refers to a measure of the hydrophilicity of a conjugate relative to the hydrophilicity of the targeting agent alone (i.e., a Ligand, typically an antibody). The hydrophilicity index is measured as the retention time of a conjugate to that of the corresponding unconjugated targeting agent (alone) under high performance liquid chromatography (HPLC) conditions, as further described herein. For example, the retention time of a Ligand-Linker-Drug Conjugate, relative to the retention time of the unconjugated Ligand (typically an antibody), can be determined.

In selected embodiments, the retention time of the conjugate is not greater than two minutes slower than the retention time of the unconjugated ligand, as determined as described in the examples (referred to as a hydrophilicity index of 2). In certain embodiments, the retention time of the conjugate is not greater than one minute slower than the retention time of the unconjugated ligand, as determined as described in the examples (referred to as a hydrophilicity index of 1). In certain embodiments, the retention time of the conjugate is not greater than one half minute slower than the retention time of the unconjugated ligand, as determined as described in the examples (referred to as a hydrophilicity index of 0.5). If a different hydrophobic interaction column and/or method is used, it can be calibrated using conjugates from Tables 2 as references to determine reference conjugate mobilities (elution times) on the selected column and/or method. The determined reference mobilities on the selected hydrophobic interaction column and/or method can then be used to calculate a hydrophilicity index of a test article (as would be determined following Example 3). For example, an auristatin T-Glu-Dpr-MA, an me-MMAF and an mc-vc-PABC-MMAE drug linkers can be used to form conjugates to use as references. In another example, an auristatin T-Glu-Dpr-MA-h1F6 ADC, an h1F6-mc-MMAF and an h1F6-mc-vc-PABC-MMAE ADC can be used as references.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkane" or "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkane may be a monocyclic, a bicyclic or a polycylic ring system. Non limiting examples of heterocycloalkane groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A heterocycloalkane group can be attached to the remainder of the molecule through a ring carbon or a heteroatom.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower "alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

As used herein, a wavy line, "∼", that intersects a single, double or triple bond in any chemical structure depicted herein, represent the point attachment of the single, double, or triple bond to the remainder of the molecule.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as dialkylamino or —$NR^aR^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems, when described as 'substituted' are selected from the group of acceptable substituents described below.

The term "arylalkyl" is meant to include those radicals in which an aryl group is attached to an alkyl group (e.g., benzyl, phenethyl, and the like). Similarly, the term "heteroaryl-alkyl" is meant to include those radicals in which a heteroaryl group is attached to an alkyl group (e.g., pyridylmethyl, thiazolylethyl, and the like).

The above terms (e.g., "alkyl," "aryl" and "heteroaryl"), in some embodiments, will include both substituted and unsubstituted forms of the indicated radical. Preferred substituents for each type of radical are provided below.

Unless otherwise indicated by context, substituents for the alkyl radicals (including those groups often referred to as alkylene, alkenyl, alkynyl and cycloalkyl) can be a variety of groups selected from: -halogen, —OR', —NR'R", —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$N'R", —NR'S(O)$_2$R", —CN and —NO$_2$ in a number ranging from zero to (2 m'+1), where m' is the total number of carbon atoms in such radical. R', R" and R'" each independently refer to hydrogen, unsubstituted —C$_{1-8}$ alkyl, unsubstituted aryl, aryl substituted with 1-3 halogens, unsubstituted —C$_{1-8}$ alkyl, C$_{1-8}$ alkoxy or C$_{1-8}$ thioalkoxy groups, or unsubstituted aryl-C$_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro(C$_1$-C$_4$)alkoxy, and perfluoro(C$_1$-C$_4$)alkyl, in a number ranging from zero to the total number of open valences on the aromatic ring system; and where R', R" and R'" are independently selected from hydrogen, C$_{1-8}$, alkyl, haloalkyl, C$_{3-6}$ cycloalkyl, C$_{2-8}$ alkenyl, alkynyl, unsubstituted aryl and heteroaryl, (unsubstituted aryl)-C$_{1-4}$ alkyl, and unsubstituted aryloxy-C$_{1-4}$ alkyl. Other suitable substituents include each of the above aryl substituents attached to a ring atom by an alkylene tether of from 1-4 carbon atoms.

The term "base" refers to a functional group that deprotonates water to produce a hydroxide ion. Exemplary bases are amines and nitrogen containing heterocycles. Representative bases include —N(R$^3$)(R$^4$) wherein R$^3$ and R$^4$ are independently selected from H or C$_{1-6}$ alkyl, preferably H or methyl,

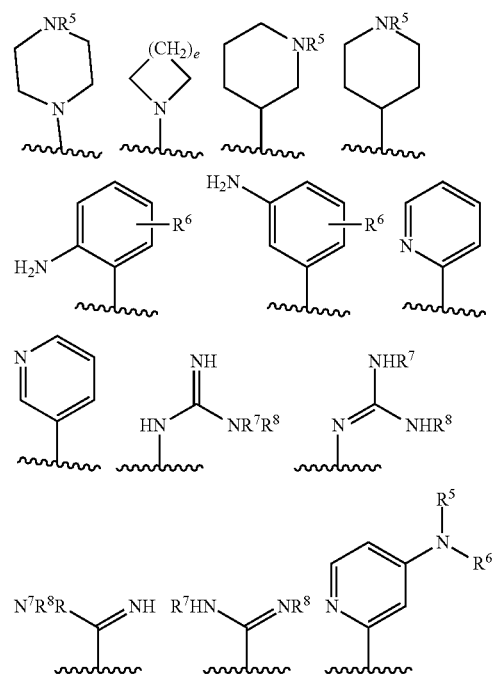

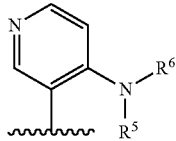

wherein $R^5$, $R^6$, $R^7$ and $R^8$ are, at each occurrence, independently selected from hydrogen or $C_{1-6}$ alkyl, preferably H or methyl, and e is 0-4. In some aspects, the base is a nitrogenous base.

The term "antibody" is used herein in the broadest sense and specifically covers intact monoclonal antibodies, polyclonal antibodies, monospecific antibodies, multispecific antibodies bispecific antibodies), and antibody fragments that exhibit the desired biological activity (i.e., specific binding to a target antigen). An intact antibody has primarily two regions: a variable region and a constant region. The variable region specifically binds to and interacts with a target antigen. The variable region includes complementary determining regions (CDR) that recognize and bind to a specific binding site on a particular antigen. The constant region may be recognized by and interact with the immune system (see, e.g., Janeway et al., 2001, *Immuno. Biology*, 5th Ed., Garland Publishing, New York). An antibody can be of any type (e.g., IgG, IgE, IgM, IgD, and IgA), class (e.g., IgG1, IgG2, IgG3, IgG4, IgA1 and IgA2) or subclass. The antibody can be derived from any suitable species. In some embodiments, the antibody is of human or murine origin. A monoclonal antibody can be, for example, human, Humanized or chimeric.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

An "intact antibody" is one which comprises an antigen-binding variable region as well as a light chain constant domain ($C_L$) and heavy chain constant domains, $C_H1$, $C_H2$, $C_H3$ and $C_H4$, as appropriate for the antibody class. The constant domains may be native sequence constant domains (e.g., human native sequence constant domains) or amino acid sequence variant thereof.

An "antibody fragment" comprises a portion of an intact antibody, comprising the antigen-binding or variable region thereof. Examples of antibody fragments include Fab, Fab', $F(ab')_2$, and Fv fragments, diabodies, triabodies, tetrabodies, linear antibodies, single-chain antibody molecules, scFv, scFv-Fc, multispecific antibody fragments formed from antibody fragment(s), a fragment(s) produced by a Fab expression library, or an epitope-binding fragments of any of the above which specifically bind to a target antigen (e.g., a cancer cell antigen, a viral antigen or a microbial antigen).

An "antigen" is an entity to which an antibody specifically binds. An antigen can be, for example, proteinaceous (e.g., a protein, polypeptide or peptide), non-proteinaceous (e.g., a carbohydrate), or a combination of the two.

The terms "specific binding" and "specifically binds" mean that the targeting agent or Ligand, such as an antibody or antigen binding fragment, will bind in a highly selective manner with its corresponding target antigen and not with the multitude of other antigens. For an antibody, the antibody or antibody fragment typically binds with an affinity of at least about $1 \times 10^{-7}$ M, and preferably $10^{-8}$ M to $10^{-9}$ M, $10^{-10}$ M, $10^{-11}$ M, or $10^{-12}$ M and binds to the predetermined antigen with an affinity that is at least two-fold greater than its affinity for binding to a non-specific antigen (e.g., BSA, casein) other than the predetermined antigen or a closely-related antigen having the same epitope.

The terms "inhibit" or "inhibition of" means to a reduce by a measurable amount, or to prevent entirely.

The term "therapeutically effective amount" refers to an amount of a conjugate (e.g., an antibody drug conjugate) that is effective to treat a disease or disorder in a mammal. In the case of cancer, a therapeutically effective amount of the conjugate may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit tumor growth; and/or relieve one or more of the symptoms associated with the cancer. To the extent the drug may inhibit growth and/or kill existing cancer cells, it may be cytostatic and/or cytotoxic. For cancer therapy, efficacy can, for example, be measured by assessing the time to disease progression (TTP) and/or determining the response rate (RR).

The term "substantial" or "substantially" refers to a majority, i.e. >50% of a population, of a mixture or a sample, preferably more than 50%, 55%, 60%, 65%, 70%, 75%, 80%, 85%, 90%, 91%, 92%, 93%, 94%, 95%, 96%, 97%, 98%, or 99% of a population.

The terms "intracellularly cleaved" and "intracellular cleavage" refer to a metabolic process or reaction inside a cell on a Ligand-Linker-Drug conjugate (e.g., an Antibody Drug Conjugate (ADC), or the like), whereby the covalent attachment (the Linker unit), between the $D_E$ moiety and the Ligand unit (e.g., an antibody (Ab)) is broken, resulting in the release of the $D_E$ unit. The cleaved moieties of the Ligand-Linker-Drug conjugate are thus intracellular metabolites.

The term "cytotoxic activity" refers to a cell-killing or a cytotoxic effect of a Ligand-Linker-Drug conjugate compound, typically via the released Drug unit, on the target cell, Cytotoxic activity may be expressed as the $IC_{50}$ value (also referred to as the half maximal inhibitory concentration), which is the concentration (molar or mass) per unit volume at which half the cells survive exposure to the conjugate.

The term "cytotoxic agent" as used herein refers a substance that kills cells or otherwise causes destruction of cells.

The terms "cancer" and "cancerous" refer to or describe the physiological condition or disorder in mammals that is typically characterized by unregulated cell growth, A "tumor" comprises cancerous cells.

An "autoimmune disease" is a disease or disorder arising from and directed against an individual's own tissues or proteins.

Examples of a "patient" include, but are not limited to, a human, rat, mouse, guinea pig, monkey, pig, goat, cow, horse, dog, cat, bird and fowl. In an exemplary embodiment, the patient is a human.

The terms "treat" or "treatment," unless otherwise indicated by context, refer to therapeutic treatment and prophylactic measures to prevent relapse, wherein the object is to inhibit or slow down (lessen) an undesired physiological change or disorder, such as the development or spread of cancer. Beneficial or desired clinical results include, but are not limited to, alleviation of symptoms, diminishment of extent of disease, a stabilized (i.e., not worsening) state of disease, delay or slowing of disease progression, amelioration or palliation of the disease state, and remission (whether partial or complete), whether detectable or undetectable. "Treatment" can also mean prolonging survival as compared to expected survival if not receiving treatment. Those in need of treatment include those already with the condition or disorder.

In the context of cancer, the term "treating" includes any or all of: inhibiting growth of tumor cells, cancer cells, or of a tumor; inhibiting replication of tumor cells or cancer cells, lessening of overall tumor burden or decreasing the number of cancerous cells, and ameliorating one or more symptoms associated with the disease.

In the context of an autoimmune disease, the term "treating" includes any or all of: inhibiting replication of cells associated with an autoimmune disease state including, but not limited to, cells that produce an autoimmune antibody, lessening the autoimmune-antibody burden and ameliorating one or more symptoms of an autoimmune disease.

The phrase "pharmaceutically acceptable salt," as used herein, refers to pharmaceutically acceptable organic or inorganic salts of a compound (e.g., a Drug, Drug-Linker, or a Ligand-Linker-Drug Conjugate). The compound can contain at least one amino group, and accordingly acid addition salts can be formed with the amino group. Exemplary salts include, but are not limited to, sulfate, trifluoroacetate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

DETAILED DESCRIPTION

General

The present invention is based, in part, on the discovery that certain combinations linking groups and cytotoxic agents can be used to prepare Ligand-Linker-Drug conjugates, such as antibody-drug conjugates (ADCs), that have a hydrophilicity similar to that of the unconjugated Ligand (i.e., a targeting agent, such as an antibody or antigen binding fragment). By maintaining a conjugate hydrophilicity similar to that of the unconjugated Ligand, the resulting conjugates can have higher drug loadings (e.g., at least 4 or 8 drug linkers per Ligand), while maintaining certain desirable characteristics of the Ligand alone, such as reduced clearance in vivo, increased pharmacokinetic profile in vivo, increased exposure of the conjugates to the target cell(s), etc. Advantageously, such hydrophilic conjugates can be designed to have a hydrophilicity similar to that of the Ligand without the need to include additional solubilizing groups, such as polyethylene glycol or other water soluble polymers. (Ligand-Linker-Drug conjugates are also referred to as Drug-Ligand conjugates, Ligand-Drug conjugates or Ligand Drug conjugates herein.)

The hydrophilic linking groups (also referred to as Linkers or Linker units) of the conjugates are designed for increased hydrophilicity. The linking group allows efficient release of the cytotoxic agent (also referred to as a Drug unit or Drug) at the target cell, sufficient to induce cytotoxicity or a cytostatic effect in the case of a cytotoxic agent. Typically, the hydrophilic linkers are designed for efficient release of the Drug unit once the conjugate has been internalized into the target cell. Suitable recognition sites for release of the Drug unit by cleavage are those that allow efficient separation of the unit from the hydrophilic linking group. Typically, the recognition site is a peptide cleavage site (such as is formed in combination with a cytotoxic agent that has an amino acid or peptide character at the site of attachment to the linking group). Examples of peptide cleavage sites include those recognized by intracellular proteases, such as those present in lysosomes. In embodiments where the linking group is attached to an amino acid of an effector moiety ($D_E$), $AA_1$ forms a cleavable peptide bond with the $D_E$ unit. The cleavable peptide bond is susceptible to cleavage by proteases when the conjugate reaches its targeted site. In other embodiments, $AA_1$ forms an amide bond with an attachment site of the effector moiety ($D_E$) that is susceptible to cleavage (e.g., by proteases) when the conjugate reaches its targeted site.

In some embodiments, the Drug units are auristatins that are designed to have increased hydrophilicity in combination with a hydrophilic Linker unit. The Drug units advantageously can be designed to have hydrophilic substituents, while retaining potent cytotoxic activity. Auristatin Drug units are attached at their C-terminal end to a Linker unit, as more fully described herein.

Accordingly, in some embodiments $L^H$ is a hydrophilic linker containing one, two, three or four hydrophilic amino acids, wherein the first amino acid forms a cleavage site with the portion of the Drug unit to which it is attached. In some embodiments, $L^H$ is a hydrophilic linker comprising one or two hydrophilic amino acids, wherein the first amino acid forms a cleavage site with the portion of the Drug unit to which it is attached. In some embodiments, $L^H$ is a hydrophilic linker comprising an amino acid that forms a cleavage site with the portion of the Drug unit to which it is attached. In some embodiments, the second, third and/or fourth hydrophilic amino acid is replaced by an optionally substituted alkylene or heteroalkylene group.

Conjugate hydrophilicity can be determined by comparing the hydrophilicity of the conjugate to that of the unconjugated targeting agent (i.e., Ligand or Ligand unit), referred to as the hydrophilicity index. In certain embodiments, the retention time of the conjugate is not greater than two minutes slower than the retention time of the unconjugated Ligand, as determined as described in the Examples. In certain other embodiments, the retention time of the conjugate is not greater than one minute slower than the retention time of the unconjugated Ligand, as determined as described in the Examples. In certain other embodiments, the retention time of the conjugate is not greater than one half minute slower than the retention time of the unconjugated Ligand, as determined as described in the Examples. Referring to the Examples, Example 3 discloses a preferred method for determining the hydrophilicity index of a conjugate. Alternatively, a different hydrophobic interaction column and/or method can be calibrated using conjugates from Tables 2 as references to determine reference conjugate mobilities (elution times) of the references on the selected column and/or method. The determined reference mobilities on the selected hydrophobic interaction column and/or method can then be used to calculate a hydrophilicity index of a test article (as would be determined following Example 3). For example, an auristatin T-Glu-Dpr-MA, an mc-MMAF and an mc-vc-PABC-MMAE drug linkers can be used to form conjugates to use as references. In another example, an auristatin T-Glu-Dpr-MA-h1F6 ADC, an h1F6-mc-MMAF and an h1F6-mc-vc-PABC-MMAE ADC can be used as references.

In view of the above, in one group of embodiments are provided a Ligand-Linker-Drug Conjugate comprising a Ligand unit and multiple Linker-Drug units attached to the Ligand unit. The Linker unit comprises a hydrophilic linker ($L^H$) assembly, including a Ligand attachment component, such as via a thioether linkage. The Drug unit comprises a cytotoxic agent having an attachment component for connection to the Linker unit. In another group of embodiments, Ligand-Linker-Drug conjugates are provided, wherein the Linker portion comprises a hydrophilic linker assembly and the Drug unit comprises a cytotoxic agent.

In related embodiments, methods are provided for administering the Ligand-Linker-Drug conjugates to a patient for the treatment of a disease. The disease can be, for example, a cancer or an autoimmune disease. The Ligand-Linker-Drug conjugates are administered in a therapeutically effective amount and on a therapeutically effective schedule. In some aspects, the conjugate dose is the same or less than that of a comparable two loaded conjugate (administered on a comparable schedule). In some aspects, the conjugate dose is the same or less than that of a comparable four loaded conjugate (administered on a comparable schedule). In some aspects, the conjugate dose is the same or less than that of a comparable two loaded conjugate, while the dosing schedule is the same or less frequent. In some aspects, the conjugate dose is the same or less than that of a comparable four loaded conjugate, while the dosing schedule is the same or less frequent. In some further aspects, the conjugate dose is less and the dosing schedule is the same or less frequent than that of a comparable two loaded conjugate. In some further aspects, the conjugate dose is less and the dosing schedule is the same or less frequent than that of a comparable four loaded conjugate. The comparator conjugate can be, for example, the same Ligand-Drug-Linker conjugate having a drug loading of 2 or 4.

In another group of embodiments, Drug-Linker units are provided wherein the Linker portion comprises a hydrophilic linker ($L^H$) assembly having a Ligand attachment component (e.g., an attached maleimide moiety), suitable for reacting with a Ligand. In another group of embodiments, Ligand-Linker conjugates are provided, wherein the Linker portion comprises a hydrophilic linker ($L^H$) assembly having features suitable for attachment and release of a Drug unit.

In another group of embodiments, methods of making Ligand-Linker-Drug conjugates are provided. In some aspects; the linker portion comprises a hydrophilic linker ($L^H$) assembly having an attached maleimide moiety, suitable for reacting with a Ligand. In a further aspect, the linker portion comprises a hydrophilic linker ($L^H$) assembly having features suitable for release of a Drug unit (when attached), Ligand-Linker Drug Conjugates In one aspect, Ligand-Linker-Drug conjugates having the following formula are provided:

(I)

or a pharmaceutically acceptable salt or solvate thereof.
wherein:
L is a Ligand that specifically binds to a target;
$L^A$ is a Ligand attachment component;
$L^H$ is an optionally branched hydrophilic linker, each branch of $L^H$ having the formula:

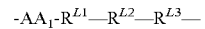

wherein:
$AA_1$ is a hydrophilic amino acid that forms a cleavable peptide bond with the C-terminal end of the Drug unit to which it is attached;
$R^{L1}$ is optional and is selected from a hydrophilic amino acid and an optionally substituted alkylene that may share an atom with $L^A$ when $R^{L1}$ is present and $R^{L2}$ and $R^{L3}$ are absent;
$R^{L2}$ is optional and is selected from a hydrophilic amino acid and an optionally substituted alkylene that may share an atom with $L^A$ when $R^{L2}$ is present and $R^{L3}$ is absent; and
$R^{L3}$ is optional and is selected from a hydrophilic amino acid and an optionally substituted alkylene that may share an atom with $L^A$ when $R^{L3}$ is present;
the subscript p is an integer of from 4 to about 20;
the subscript p' is an integer of from 1 to 4; and
D is has the formula:

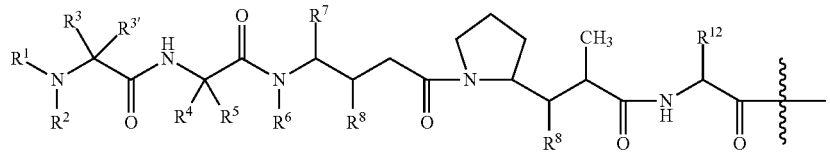

wherein:
$R^1$ and $R^2$ each are independently selected from the group consisting of hydrogen (H) and optionally substituted —$C_1$-$C_8$ alkyl; with the proviso that both $R^1$ and $R^2$ are not H, unless both of $R^3$ and $R^{3'}$ are not H;
$R^3$ is selected from the group consisting of H and optionally substituted —$C_1$-$C_8$ alkyl,
$R^{3'}$ is selected from the group consisting of H and optionally substituted —$C_1$-$C_8$ alkyl, and at least one of $R^3$ and $R^{3'}$ is not H;
$R^4$ is selected from the group consisting of H and optionally substituted —$C_1$-$C_8$ alkyl;
$R^5$ is selected from the group consisting of H and optionally substituted —$C_1$-$C_8$ alkyl;
or $R^4$ and $R^5$ jointly form a carbocyclic ring and have the formula —$(CR^aR^b)_n$—, wherein $R^a$ and $R^b$ are independently selected from the group consisting of H and optionally substituted —C$_1$-C$_8$ alkyl and n is selected from the group consisting of 2, 3, 4, 5 and 6;

the subscript p is an integer of from 4 to about 20;
the subscript p' is an integer of fro 1 to 4; and
D has the formula:

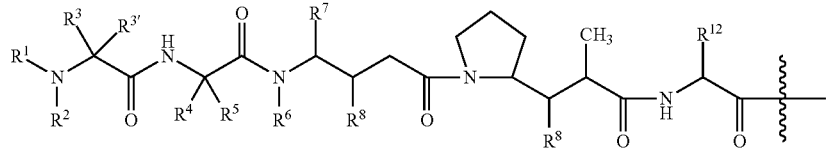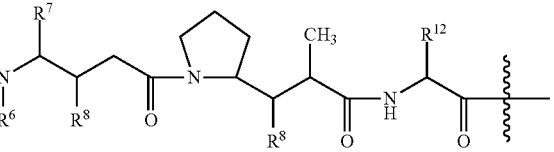

R$^6$ is selected from the group consisting of H and optionally substituted —C$_1$-C$_8$ alkyl;
R$^7$ is selected from the group consisting of H and optionally substituted —C$_1$-C$_8$ alkyl;
each R$^8$ is independently selected from the group consisting of H, —OH, optionally substituted —C$_1$-C$_8$ alkyl, and optionally substituted —O—(C$_1$-C$_8$ alkyl);
R$^{12}$ is selected from H, optionally substituted —C$_1$-C$_8$ alkyl, optionally substituted aryl, optionally substituted —X$^1$aryl, optionally substituted —C$_3$-C$_8$ carbocycle, optionally substituted —X$^1$—(C$_3$-C$_8$ carbocycle), optionally substituted —C$_1$-C$_8$ alkylene-NH$_2$, optionally substituted —C$_3$-C$_8$ heterocycle and optionally substituted —X$^1$—(C$_3$-C$_8$ heterocycle); and
each X$^1$ is independently —C$_1$-C$_{10}$ alkylene;
wherein the Ligand-Linker-Drug conjugate has a hydrophilicity index less than or equal to 2;
wherein the left and right lines of L$^H$ indicate covalent attachments to the Drug unit and L$^A$, respectively; and the wavy line of each D indicates a covalent attachment to L$^H$.

In related aspect, Ligand-Linker-Drug conjugates having the following formula are provided:

 (I')

or a pharmaceutically acceptable salt or solvate thereof, wherein:
L is a Ligand that specifically binds to a target;
L$^A$ is a Ligand attachment component;
L$^H$ is an optionally branched hydrophilic linker, each branch of L$^H$ having the formula:

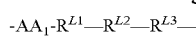
-AA$_1$-R$^{L1}$—R$^{L2}$—R$^{L3}$— wherein:
AA$_1$ is a hydrophilic amino acid that forms a cleavable peptide bond with the C-terminal end of the Drug unit to which it is attached;
R$^{L1}$ is selected from a hydrophilic amino acid and an optionally substituted alkylene that may share an atom with L$^A$ when R$^{L2}$ and R$^{L3}$ are not present;
R$^{L2}$ is optional and is selected from a hydrophilic amino acid and an optionally substituted alkylene that may share an atom with L$^A$ when R$^{L2}$ is present and R$^{L3}$ is not present; and
R$^{L3}$ is optional and is selected from a hydrophilic amino acid and an optionally substituted alkylene that may share an atom with L$^A$ when R$^{L3}$ is present;

wherein:
R$^1$ and R$^2$ each are independently selected from the group consisting of hydrogen (H) and optionally substituted —C$_1$-C$_4$ alkyl; with the proviso that both R$^1$ and R$^2$ are not H, unless both of R$^3$ and R$^{3'}$ are not H;
R$^3$ is selected from the group consisting of and optionally substituted —C$_1$-C$_4$ alkyl,
R$^{3'}$ is selected from the group consisting of H and optionally substituted —C$_1$-C$_4$ alkyl, and at least one of R$^3$ and R$^{3'}$ is not II;
R$^4$ is selected from the group consisting of H and optionally substituted —C$_1$-C$_4$ alkyl;
R$^5$ is selected from the group consisting of H and optionally substituted —C$_1$-C$_4$ alkyl;
or R$^4$ and R$^5$ jointly form a carbocyclic ring and have the formula —(CR$^a$R$^b$)$_n$—, wherein R$^a$ and R$^b$ are independently selected from the group consisting of H and optionally substituted —C$_1$-C$_4$ alkyl and n is selected from the group consisting of 2, 3, 4, 5 and 6;
R$^6$ is selected from the group consisting of and optionally substituted —C$_1$-C$_4$ alkyl;
R$^7$ is selected from the group consisting of H and optionally substituted —C$_1$-C$_4$ alkyl;
each R$^8$ is independently selected from the group consisting of H, —OH, optionally substituted —C$_1$-C$_4$ alkyl, and optionally substituted —O—(C$_1$-C$_4$ alkyl);
R$^{12}$ is selected from H, optionally substituted —C$_1$-C$_8$ alkyl, optionally substituted aryl, optionally substituted —X$^1$aryl, optionally substituted —C$_3$-C$_8$ carbocycle, optionally substituted —X$^1$—(C$_3$-C$_8$ carbocycle), optionally substituted —C$_1$-C$_8$ alkylene-NH$_2$, optionally substituted —C$_3$-C$_8$ heterocycle and optionally substituted —X$^1$—(C$_3$-C$_8$ heterocycle); and
each X$^1$ is independently —C$_1$-C$_{10}$ alkylene;
wherein the Ligand-Linker-Drug conjugate has a hydrophilicity index less than or equal to 2;
wherein the left and right lines of L$^H$ indicate covalent attachments to the Drug unit and L$^A$, respectively; and the wavy line of each D indicates a covalent attachment to L$^H$.

Various components of the Ligand-Linker-Drug conjugates of formulas I and I' are provided in more detail below.

In some aspects, the Ligand-Linker-Drug conjugates comprise a Ligand unit and at least four Linker-Drug units, wherein the Ligand unit and each of the Drug unit(s) are joined by a Linker unit(s) comprising a hydrophilic linker (L$^H$) assembly. In some further aspects, the Linker units are attached to the Ligand unit via a thioether bond. In some related aspects, each Linker unit further comprises a hydrolyzed succinimide ring (or succinic acid) directly conjugated to the Ligand unit via a thioether linkage.

In some aspects, the Ligand-Linker-Drug conjugates comprise a Ligand unit and at least six Linker-Drug units, wherein the Ligand unit and each of the Drug unit(s) are joined by a Linker unit(s) comprising a hydrophilic linker ($L^H$) assembly. In some further aspects, the Linker units are attached to the Ligand unit via a thioether bond. In some related aspects, each Linker unit further comprises a hydrolyzed succinimide ring (or succinic acid) directly conjugated to the Ligand unit via a thioether linkage.

In some aspects, the Ligand-Linker-Drug conjugates comprise a Ligand unit and at least eight Linker-Drug units, wherein the Ligand unit and each of the Drug unit(s) are joined by a Linker unit(s) comprising a hydrophilic linker ($L^H$) assembly. In some further aspects, the Linker units are attached to the Ligand unit via a thioether bond. In some related aspects, each Linker unit further comprises a hydrolyzed succinimide ring (or succinic acid) directly conjugated to the Ligand unit via a thioether linkage.

In some aspects, the Ligand-Linker-Drug conjugates comprise a Ligand unit and at least ten Linker-Drug units, wherein the Ligand unit and each of the Drug unit(s) are joined by a Linker unit(s) comprising a hydrophilic linker ($L^H$) assembly. In some further aspects, the Linker units are attached to the Ligand unit via, a thioether bond. In some related aspects, each Linker unit further comprises a hydrolyzed succinimide ring (or succinic acid) directly conjugated to the Ligand unit via a thioether linkage.

In some aspects, the Ligand-Linker-Drug conjugates comprise a Ligand unit and at least sixteen Linker-Drug units, wherein the Ligand unit and each of the Drug unit(s) are joined by a Linker unit(s) comprising a hydrophilic linker ($L^H$) assembly. In some further aspects, the Linker units are attached to the Ligand unit via a thioether bond. In some related aspects, each Linker unit further comprises a hydrolyzed succinimide ring (or succinic acid) directly conjugated to the Ligand unit via a thioether linkage.

Drug Unit

Referring to the Drug unit of formulas I and I' in some embodiments $R^{12}$ is selected from H, optionally substituted —$C_1$-$C_8$ alkyl, optionally substituted aryl, optionally substituted —$X^1$aryl, optionally substituted —$C_3$-$C_8$ carbocycle, optionally substituted —$X^1$—($C_3$-$C_8$ carbocycle), optionally substituted —$C_1$-$C_8$ alkylene-$NH_2$, optionally substituted —$C_3$-$C_8$ heterocycle and optionally substituted —$X^1$—($C_3$-$C_8$ heterocycle).

In some related embodiments, $R^{12}$ is not the side chain of phenylalanine or proline. In some further related embodiments, $R^{12}$ is not the side chain of phenylalanine, methionine, tryptophan or proline.

In some embodiments, $R^{12}$ is selected from the side chains of natural L-amino acids other than proline, and glycine. In some further embodiments, $R^{12}$ is selected from the side chains of natural L-amino acids other than proline, glycine or phenylalanine. In some further embodiments, $R^{12}$ is selected from the side chains of natural L-amino acids other than proline, glycine, tryptophan, methionine or phenylalanine.

In some further embodiments, $R^{12}$ is selected from the side chains of the group of hydrophilic amino acids consisting of threonine, serine, asparagine, aspartic acid, glutamine, glutamic acid, homoserine, hydroxyvaline, furyl alanine, threortine($PO_3H_2$), pyrazolyl alanine, triazolyl alanine and thiazolyl alanine.

In some embodiments, $R^{12}$ is the side chain of threonine.

Exemplary Drug units have the following formula, or a pharmaceutically acceptable salt thereof, wherein the wavy line indicates site of attachment to the Linker unit. In some exemplary units, the Drug unit is dimethyl- or monomethyl-auristatin F, as shown below:

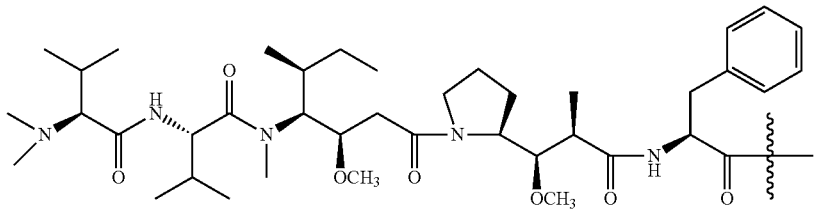

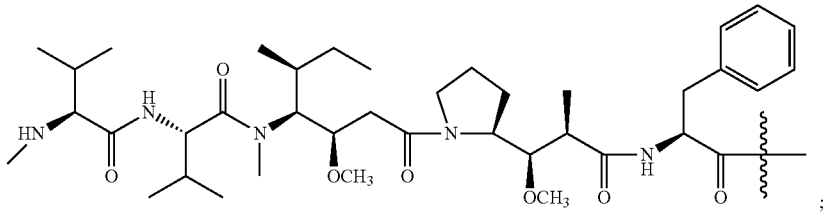

or a pharmaceutically acceptable salt or solvate thereof.

Other exemplary Drug units are the dimethyl- or monomethyl forms of auristatin T.

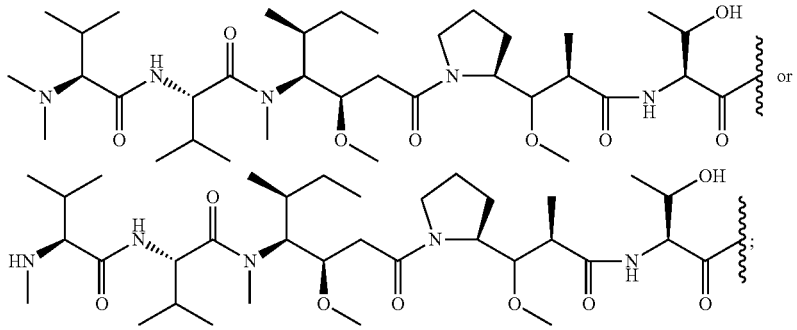

or a pharmaceutically acceptable salt or solvate thereof.

The Linker Unit

Referring to the Linker unit of formulas I and I', in some embodiments $L^A$ is covalently linked to a sulfur atom of the Ligand. In some aspects, the sulfur atom is that of a cysteine residue that can form an interchain disulfide bond of an antibody. In another aspect, the sulfur atom is that of a cysteine residue that has been introduced into the Ligand unit (e.g., by site directed mutagenesis or chemical reaction). In further aspects, the sulfur atoms to which the $L^A$'s are attached are selected from cysteine residues that form an interchain disulfide bond of an antibody and cysteine residues that have been introduced into the Ligand unit (e.g., by site directed mutagenesis or chemical reaction).

$AA_1$ forms a cleavable bond with the Drug unit. In embodiments where $AA_1$ is attached to an amino acid of the Drug unit, $AA_1$ forms a cleavable peptide bond with the Drug unit. The cleavable peptide bond is susceptible to cleavage by proteases when the conjugate reaches its target site. In some embodiments, $AA_1$ is a hydrophilic amino acid, typically an amino acid that is selected from the group consisting of Glycine and L forms of Aspartate, Glutamate, Asparagine, Glutamine, Histidine, Lysine, Arginine, Serine and Alanine. In some embodiments, $AA_1$ is Glutamate.

In embodiments where $R^{L1}$ is present and is a hydrophilic amino acid, it can be selected from the group consisting of Glycine; L or D forms of Aspartate, Glutamate, Asparagine, Glutamine, Histidine, Lysine, Arginine, Serine and Alanine; —NH—CH($R^a$)—CO—; and —N—CH(COOH)—$R^b$—; wherein $R^a$ is selected from —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$OH, —CH$_2$CH$_2$CO$_2$H, and —CH$_2$CH$_2$CH$_2$CO$_2$H; and $R^b$ is selected from —CH$_2$NH—, —CH$_2$CH$_2$NH—, —CH$_2$CH$_2$CH$_2$NH—, —CH$_2$CH$_2$CH$_2$CH$_2$NH—, —CH$_2$CH$_2$C(O)—, —CH$_2$CH$_2$CH$_2$C(O)—, and —CH$_2$CH$_2$CH$_2$CH$_2$C(O)—. In some further embodiments, $R^{L1}$ is selected from the group consisting of the D amino acids of Aspartate, Glutamate, Asparagine, Glutamine, Histidine, Lysine, Arginine, Serine and Alanine; Glycine; —NH—CH($R^a$)—C(O)—; and —NH—CH(COOH)—$R^b$—; wherein $R^a$ is selected from —CH$_2$NH$_2$, —CH$_2$CH$_2$NH$_2$—, —CH$_2$CH$_2$CH$_2$NH$_2$, —CH$_2$CH$_2$CH$_2$CH$_2$NH$_2$, —CH$_2$CH$_2$OH, —CH$_2$CH$_2$CH$_2$CO$_2$H, and —CH$_2$CH$_2$CH$_2$CO$_2$H; and $R^b$ is selected from —CH$_2$NH—, —CH$_2$CH$_2$NH—, —CH$_2$CH$_2$CH$_2$NH—, —CH$_2$CH$_2$C(O)—, —CH$_2$CH$_2$CH$_2$C(O)—, and —CH$_2$CH$_2$CH$_2$CH$_2$C(O)—.

In embodiments where $R^{L1}$ is present and is an optionally substituted alkylene, it can be a $C_1$-$C_6$ alkylene, optionally substituted with 1-4 substituents selected from —NH—, —C(O)—, —COOH, —N($C_1$-$C_3$ alkyl), —NH$_2$ or —NH ($C_1$-$C_3$ alkyl). In some embodiments, $R^{L1}$ is ethylenediamine, —NH—CH(COOH)—CH$_2$—NH— or —C(O)—CH(CH$_2$NH$_2$)—.

In embodiments where $R^{L2}$ is present and is a hydrophilic amino acid, it can be selected from the group consisting of Glycine; L or D forms of Aspartate, Glutamate, Asparagine, Glutamine, Histidine, Lysine, Arginine, Serine and Alanine; —NH—CH($R^a$)—C(O)—; and —NH—CH(COOH)—$R^b$; wherein $R^a$ is selected from —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$OH, —CH$_2$CH$_2$CH$_2$CO$_2$H, and —CH$_2$CH$_2$CH$_2$CH$_2$CO$_2$H; and $R^b$ is selected from —CH$_2$NH—, —CH$_2$CH$_2$NH—, —CH$_2$CH$_2$CH$_2$NH—, —CH$_2$—CH$_2$—CH$_2$—CH$_2$NH—, —CH$_2$—CH$_2$C(O)—, —CH$_2$CH$_2$CH$_2$C(O)—, and —CH$_2$CH$_2$CH$_2$CH$_2$C(O), In some further embodiments when $R^{L2}$ is present, it is selected from the group consisting of the D amino acids of Aspartate, Glutamate, Asparagine, Glutamine, Histidine, Lysine, Arginine, Serine and Alanine; Glycine; —NH—CH($R^a$)—C(O)—; and —NH—CH(COOH)—$R^b$—; wherein $R^a$ is selected from —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$OH, —CH$_2$CH$_2$CH$_2$CO$_2$H, and —CH$_2$CH$_2$CH$_2$CH$_2$CO$_2$H; and $R^b$ is selected from —CH$_2$NH—, —CH$_2$CH$_2$NH—, —CH$_2$CH$_2$CH$_2$NH—, —CH$_2$CH$_2$CH$_2$CH$_2$NH—, —CH$_2$CH$_2$C(O)—, —CH$_2$CH$_2$CH$_2$C(O)—, and —CH$_2$CH$_2$CH$_2$CH$_2$C(O)—.

In embodiments where $R^{L2}$ is present and is an optionally substituted alkylene, it can be a $C_1$-$C_6$ alkylene, optionally substituted with 1-4 substituents selected from —NH—, —C(O)—, —COOH, —N($C_1$-$C_3$ alkyl)-, —NH$_2$ or —NH ($C_1$-$C_3$ alkyl). In some embodiments, $R^{L2}$ is ethylenediamine, —NH—CH(COOH)—CH$_2$—NH— or —C(O)—CH(CH$_2$NH$_2$)—.

In embodiments where $R^{L3}$ is present, and is a hydrophilic amino acid, it can be selected from the group consisting of Glycine; L or D forms of Aspartate, Glutamate, Asparagine, Glutamine, Histidine, Lysine, Arginine, Serine and Alanine; —NH—CH($R^a$)—C(O)—; and —NH—CH(COOH)—$R^b$—; wherein $R^a$ is selected from —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$OH, —CH$_2$CH$_2$CH$_2$CO$_2$H, and —CH$_2$CH$_2$CH$_2$CH$_2$CO$_2$H; and $R^b$ is selected from —CH$_2$NH—, —CH$_2$CH$_2$NH—, —CH$_2$CH$_2$CH$_2$NH—, —CH$_2$CH$_2$CH$_2$CH$_2$NH—, —CH$_2$CH$_2$C(O)—, —CH$_2$CH$_2$CH$_2$C(O)—, and —CH$_2$CH$_2$CH$_2$CH$_2$C(O)—.

In some further embodiments when $R^{L3}$ is present, it is selected from the group consisting of the D amino acids of Aspartate, Glutamate, Asparagine, Glutamine, Histidine, Lysine, Arginine, Serine and Alanine; Glycine; —NH—CH(R$^a$)—C(O)—; and —NH—CH(COOH)—R$^b$—; wherein R$^a$ is selected from —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$OH, —CH$_2$CH$_2$CH$_2$CO$_2$H, and —CH$_2$CH$_2$CH$_2$CH$_2$CO$_2$H; and R$^b$) is selected from —CH$_2$NH—, —CH$_2$CH$_2$CH$_2$NH—, —CH$_2$CH$_2$CH$_2$CH$_2$NH—, —CH$_2$CH$_2$C(O)—, —CH$_2$CH$_2$CH$_2$C(O)—, and —CH$_2$CH$_2$CH$_2$CH$_2$C(O)—.

In embodiments where $R^{L3}$ is present and is an optionally substituted alkylene, it can be a C$_1$-C$_6$ alkylene, optionally substituted with 1-4 substituents selected from —NH—, —C(O)—, —COOH, —N(C$_1$-C$_3$ alkyl)-, —NH$_2$ or —NH (C$_1$-C$_3$ alkyl). In some embodiments, $R^{L1}$ is ethylenediamine, —NH—CH(COOH)—CH$_2$—NH— or —C(O)—CH(CH$_2$NH$_2$)—.

In some embodiments of the above, AA$_1$ is present and $R^{L1}$, $R^{L2}$ and $R^{L3}$ are absent.

In some embodiments of the above, AA$_1$ is present, $R^{L1}$ is present and $R^{L2}$ and $R^{L3}$ are absent.

In some embodiments of the above, AA$_1$ is present, $R^{L1}$ is present, $R^{L2}$ is present and $R^{L3}$ is absent.

In some embodiments the above, AA$_1$ is present, $R^{L1}$ is present, $R^{L2}$ is present and $R^{L3}$ is present.

In some embodiments of the above, AA$_1$ is a hydrophilic amino acid and at least one of $R^{L1}$, $R^{L2}$ and $R^{L3}$ is present and is an optionally substituted alkylene, as set forth above.

In some embodiments of the above, AA$_1$ is Glutamate and at least one of $R^{L1}$, $R^{L2}$ and $R^3$ is present and is an optionally substituted alkylene, as set forth above.

In some embodiments of the above, AA$_1$ is Glutamate, $R^{L1}$ is a hydrophilic amino acid and at least one of $R^{L2}$ and $R^{L3}$ is present and is an optionally substituted alkylene, as set forth above.

In some embodiments of the above, AA$_1$ and $R^{L1}$ are hydrophilic amino acids and at least one of $R^{L2}$ and $R^{L3}$ is present and is an optionally substituted alkylene, as set forth above.

In some embodiments of the above, AA$_1$ is a hydrophilic amino acid and $R^{L1}$ and optionally $R^{L2}$ are an optionally substituted alkylene, as set forth above.

In some embodiments of the above, L$^H$ does not include a glycine dipeptide (Gly-Gly), tripeptide or tetrapeptide. In some embodiments, L$^H$ does not include the peptide Asn-(D)Lys.

In some embodiments, L$^H$ will include a modified peptide, having from two to four amino acids. The modified peptide has an amino acid in the 1-position (AA$_1$) that is selected to optimize release of the Drug unit (e.g., by protease cleavage via an amide peptide bond). In one or both of positions $R^{L1}$ and $R^{L2}$ is an amino acid that reverses the orientation of typical N to C linkages of peptides (forming amide bonds) and facilitates attachment of the last amino acid (e.g., $R^{L2}$ or $R^{L3}$) which, prior to attachment of the Ligand unit, includes an α-amino group protected as a maleimide. The amino acid having a reversed N to C linkage is attached to the next group via its side chain. In some embodiments, this amino acid is an alpha amino acid. In other embodiments, it can be a beta or gamma amino acid. In some of these embodiments, the side chain is selected from —CH$_2$NH$_2$—, —CH$_2$CH$_2$NH$_2$—, —CH$_2$CH$_2$CH$_2$NH$_2$—, and —CH$_2$CH$_2$CH$_2$CH$_2$NH$_2$—.

In some embodiments of L$^H$, the amino acid having a reversed N to C linkage ($R^{L1}$) is attached to $R^{L2}$ or $R^{L3}$, where $R^{L2}$ or $R^{L3}$ is a hydrophilic amino acid or an optionally substituted alkylene, according to any of the embodiments described above.

In some embodiments of L$^H$, the amino acid having a reversed N to C linkage ($R^{L1}$) is attached to $R^{L2}$, where $R^{L2}$ is an optionally substituted alkylene, according to any of the embodiments described above.

In some further embodiments, L$^H$ is a hydrophilic, cleavable linker, each branch having the formula:

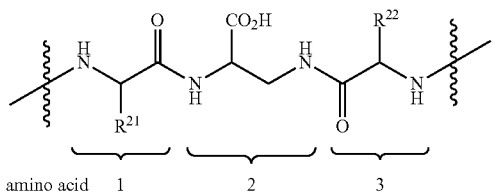

wherein $R^{21}$ is selected from —CH$_2$NH$_2$, —CH$_2$CH$_2$NH$_2$, —CH$_2$OH, —CH$_2$CH$_2$OH, —CH$_2$CO$_2$H, —CH$_2$CH$_2$CO$_2$H, —CH$_2$CH$_2$CH$_2$CO$_2$H and —CH$_2$CH$_2$CH$_2$CH$_2$CO$_2$H; and $R^{22}$ is selected from —CH$_2$NH$_2$, —CH$_2$CH$_2$NH$_2$, —CH$_2$OH, and —CH$_2$CH$_2$OH. The left and right wavy lines indicate attachments to the Drug unit and L$^A$, or the branch of L$^H$, respectively.

In further embodiments L$^H$, or a branch thereof, has the formula:

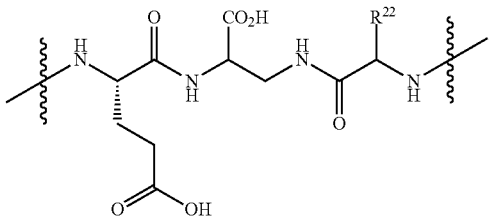

wherein $R^{22}$ is selected from —CH—NH$_2$, —CH$_2$CH$_2$NH$_2$, —CH$_2$OH, and —CH$_2$CH$_2$OH. In some embodiments, $R^{22}$ is selected from —CH$_2$NH$_2$ and —CH$_2$CH$_2$NH$_2$. The left and right wavy lines indicate attachments to the Drug unit and L$^A$, or the branch of L$^H$, respectively.

In certain embodiments, L$^H$, or a branch thereof, has the formula:

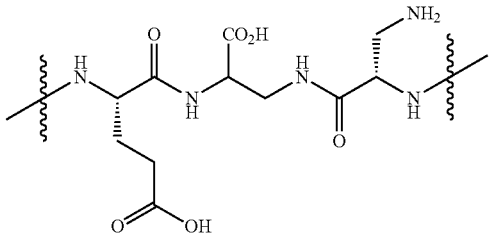

The left and right wavy lines indicate attachments to the Drug unit and $L^A$, respectively.

In certain embodiments, $L^H$, or a branch thereof, has the formula:

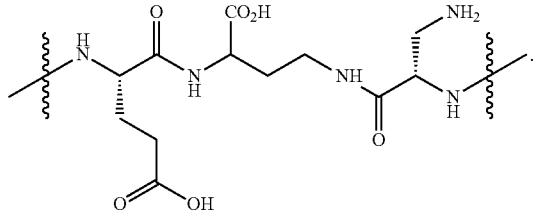 [SMILES: *N[C@@H](CN)C(=O)NCCC(NC(=O)[C@H](CCC(=O)O)N*)C(=O)O]

The left and right wavy lines indicate attachments to the Drug unit and $L^A$, or the branch of $L^H$, respectively.

In certain embodiments, $L^H$, or a branch thereof, has the formula:

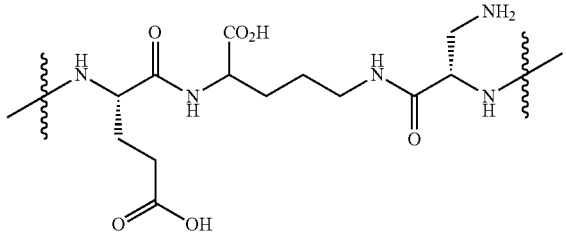 [SMILES: *N[C@@H](CN)C(=O)NCCCC(NC(=O)[C@H](CCC(=O)O)N*)C(=O)O]

The left and right wavy lines indicate attachments to the Drug unit and $L^A$, or the branch of $L^H$, respectively.

In certain embodiments, $L^H$, or a branch thereof, has the formula:

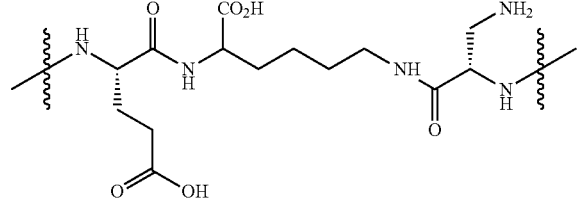

The left and right wavy lines indicate attachments to the Drug unit and $L^A$, or the branch of $L^H$, respectively.

In certain embodiments, $L^H$, or a branch thereof, has the formula:

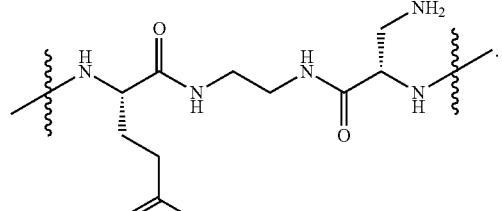

The left and right wavy lines indicate attachments to the Drug unit and $L^A$ or the branch of $L^H$, respectively.

In certain embodiments $L^H$, or a branch thereof, has the formula:

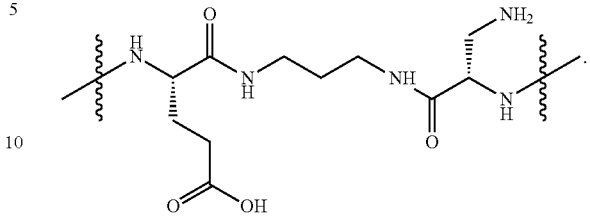

The left and right wavy lines indicate attachments to the Drug unit and $L^A$, respectively.

In certain embodiments, $L^H$, or a branch thereof, has the formula:

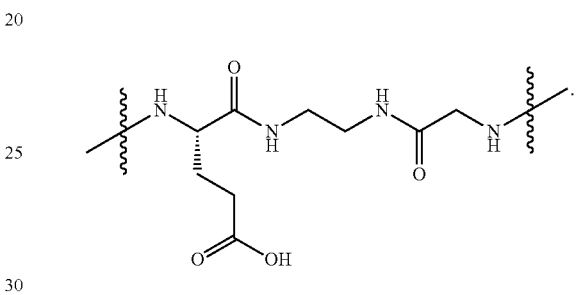

The left and right wavy lines indicate attachments to the Drug unit and $L^A$, or the branch of $L^H$, respectively.

In some further embodiments of the above, $L^H$ is a branched hydrophilic linker having the formula:

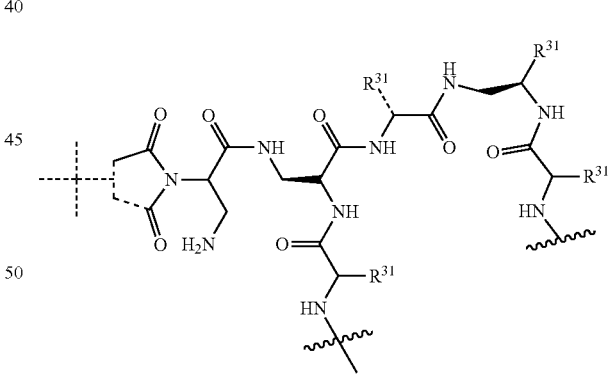

wherein each $R^{31}$ is independently selected from the group consisting of —$CH_2NH_2$, —$CH_2CH_2NH_2$, —$CH_2OH$, —$CH_2CH_2OH$, —$CH_2CO_2H$, —$CH_2CH_2CO_2H$, —$CH_2CH_2CH_2CO_2H$, and —$CH_2CH_2CH_2CH_2CO_2H$; and each of the bars adjacent the $R^{31}$ indicates an attachment to a $D_E$ unit, and the vertical dashed line indicates an attachment to a Ligand unit.

In some further embodiments of the above, $L^H$ is a branched hydrophilic linker having the formula:

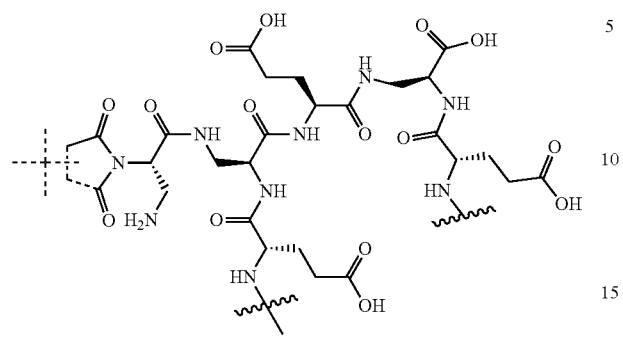

wherein each of the bars indicates attachment to a Drug unit, and the vertical dashed line indicates an attachment to a Ligand unit.

The $L^A$ subunit is described in more detail below.

Referring again to the Ligand-Linker-Drug conjugates of formulas I and I', in some further embodiments, the Ligand-Linker-Drug conjugates have a formula selected from:

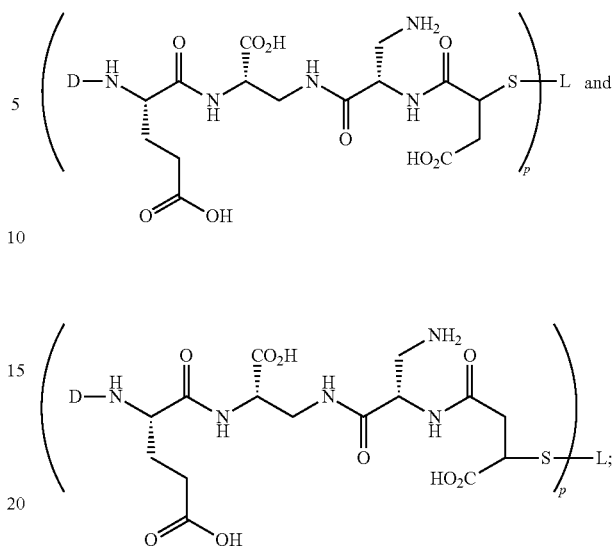

wherein S refers to a sulfur atom of the Ligand. Specific embodiments include the following:

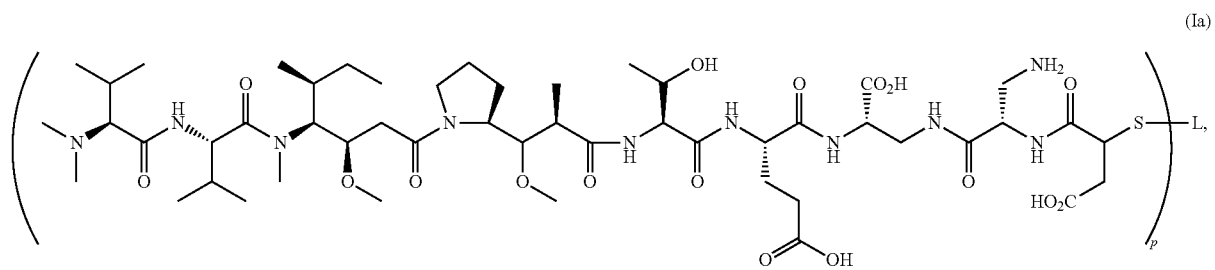

(Ia)

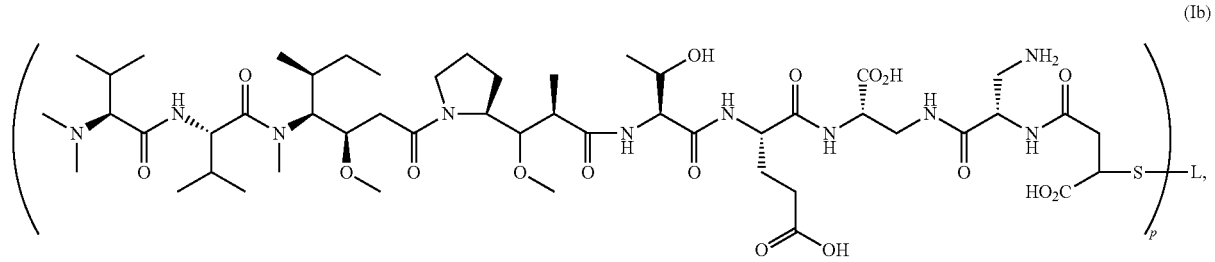

(Ib)

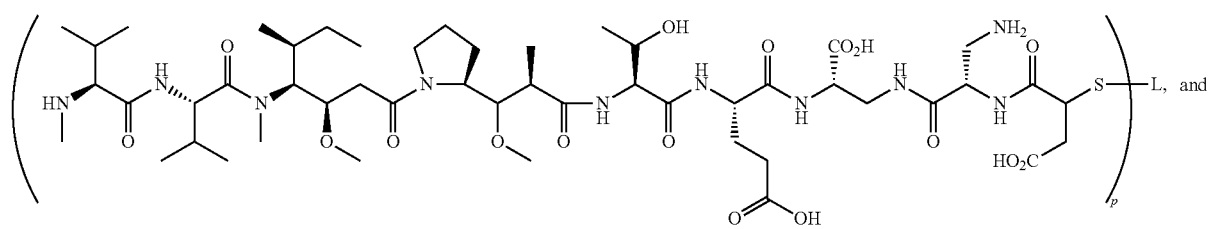

(Ic)

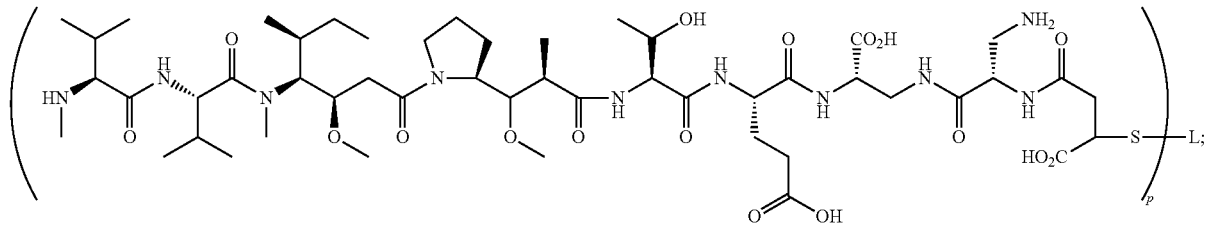

wherein S refers to a sulfur atom of the Ligand, or a pharmaceutically acceptable salt or solvate thereof.

In yet another aspect, Ligand-Linker-Drug conjugates having the following formula are provided:

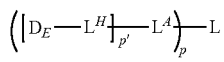

wherein;
L is a Ligand that specifically binds to a target;
$L^A$ is a Ligand attachment component;
$L^H$ is an optional hydrophilic linker, each branch of $L^H$ having the formula:

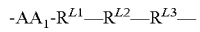

wherein
$AA_1$ is a hydrophilic amino acid that forms a cleavable bond with $D_E$;
$R^{L1}$ is optional and is selected from a hydrophilic amino acid or an optionally substituted alkylene, which may share an atom with $L^A$ when $R^{L1}$ is present and $R^{L2}$ and $R^{L3}$ are not present;
$R^{L2}$ is optional and is selected from a hydrophilic amino acid and an optionally substituted alkylene, which may share an atom with $L^A$ when $R^{L2}$ is present and $R^{L3}$ is not present; and
$R^{L3}$ is optional and is selected from a hydrophilic amino acid and an optionally substituted alkylene, which may share an atom with $L^A$ when $R^{L3}$ is present;
$L^A$ is a Ligand attachment component;
the subscript p is an integer of from 4 to about 20;
the subscript p' is an integer of from 1 to 4; and
the Ligand-Linker-Drug conjugate has a hydrophilicity index of less than or equal to 2;
wherein the left and right lines of $L^H$ indicate covalent attachments to the $D_E$ Unit and $L^A$, respectively; and
$D_E$ is effector moiety, as further described herein.

Various components of the Ligand-Linker-Drug conjugates of formula II are provided in more detail below.

In some aspects, the Ligand-Linker-Drug conjugates comprise a Ligand unit and at least four Linker-$D_E$ units, wherein the Ligand unit and each of the $D_E$ unit(s) are joined by a Linker unit comprising a hydrophilic linker ($L^H$) assembly. In some further aspects, the Linker units are attached to the Ligand unit via a thioether bond. In some related aspects, the Linker unit further comprises a hydrolyzed succinimide ring (or succinic acid) directly conjugated to the Ligand unit via a thioether linkage.

In some aspects, the Ligand-Linker-Drug conjugates comprise a Ligand unit and at least six Linker-$D_E$ units, wherein the Ligand unit and each of the $D_E$ unit(s) are joined by a Linker unit comprising a hydrophilic linker ($L^H$) assembly. In some further aspects, the Linker units are attached to the Ligand unit via a thioether bond. In some related aspects, the Linker unit further comprises a hydrolyzed succinimide ring (or succinic acid) directly conjugated to the Ligand unit via a thioether linkage.

In some aspects, the Ligand-Linker-Drug conjugates comprise a Ligand unit and at least eight Linker-$D_E$ units, wherein the Ligand unit and each of the $D_E$ unit(s) are joined by a. Linker unit comprising a hydrophilic linker ($L^H$) assembly. In some further aspects, the Linker units are attached to the Ligand unit via a thioether bond. In some related aspects, the Linker unit further comprises a hydrolyzed succinimide ring (or succinic acid) directly conjugated to the Ligand unit via a thioether linkage.

In some aspects, the Ligand-Linker-Drug conjugates comprise a Ligand unit and at least ten Linker-$D_E$ units, wherein the Ligand unit and each of the $D_E$ unit(s) are joined by a Linker unit comprising a hydrophilic linker ($L^H$) assembly. In some further aspects, the Linker units are attached to the Ligand unit via a thioether bond. In some related aspects, the Linker unit further comprises a hydrolyzed succinimide ring (or succinic acid) directly conjugated to the Ligand unit via a thioether linkage.

In some aspects, the Ligand-Linker-Drug conjugates comprise a Ligand unit and at least sixteen Linker-$D_E$ units, wherein the Ligand unit and each of the $D_E$ unit(s) are joined by a Linker unit comprising a hydrophilic linker ($L^H$) assembly. In some further aspects, the Linker units are attached to the Ligand unit via a thioether bond. In some related aspects, the Linker unit further comprises a hydrolyzed succinimide ring (or succinic acid) directly conjugated to the Ligand unit via a thioether linkage.

Referring to the Linker unit of formula II, in some embodiments $L^A$ is covalently linked to a sulfur atom of the Ligand. In some aspects, the sulfur atom is that of a cysteine residue that forms an interchain disulfide bond of an antibody. In another aspect, the sulfur atom is that of a cysteine residue that has been introduced into the Ligand unit (e.g., by site directed mutagenesis or chemical reaction). In further aspects, the sulfur atom(s) to which the $L^A$'s are attached are selected from cysteine residues that form an interchain disulfide bond of an antibody and cysteine residues that have been introduced into the Ligand unit (e.g., by site directed mutagenesis or chemical reaction).

$AA_1$ forms a cleavable bond with the $D_E$ unit. In embodiments where $AA_1$ is attached to an amino acid of the $D_E$ unit, $AA_1$ forms a cleavable peptide bond with the $D_E$ unit. The cleavable peptide bond is susceptible to cleavage by proteases when the conjugate reaches its target site. In other embodiments, $AA_1$ forms an amide bond with an attachment site of the effector moiety ($D_E$) that is susceptible to cleavage (e.g., by proteases) when the conjugate reaches its targeted site. In some embodiments of formula II, $AA_1$ is a hydrophilic amino acid, typically a natural amino acid that is selected from the group consisting of Glycine and L forms of Aspartate, Glutamate, Asparagine, Glutamine, Histidine, Lysine, Arginine, Serine and Alanine. In some embodiments, $AA_1$ is Glutamate.

In embodiments where $R^{L1}$ is present and is a hydrophilic amino acid, it can be selected from the group consisting of Glycine; L or D forms of Aspartate, Glutamate, Asparagine, Glutamine, Histidine, Lysine, Arginine, Serine and Alanine; —NH—CH($R^a$)—C(O)—; and —NH—CH(COOH)—$R^b$—; wherein $R^a$ is selected from —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$CH$_2$CO$_2$H, and —CH$_2$CH$_2$CH$_2$CH$_2$CO$_2$H; and $R^b$ is selected from —CH$_2$NH—, —CH$_2$CH$_2$NH—, —CH$_2$CH$_2$CH$_2$NH—, —CH$_2$CH$_2$CH$_2$CH$_2$NH—, —CH$_2$CH$_2$C(O)—, —CH$_2$CH$_2$CH$_2$C(O)—, and —CH$_2$CH$_2$CH$_2$CH$_2$C(O)—. In some further embodiments, $R^{L1}$ is selected from the group consisting of the D amino acids of Aspartate, Glutamate, Asparagine, Glutamine, Histidine, Lysine, Arginine, Serine and Alanine; Glycine; —NH—CH($R^a$)—C(O)—; and —NH—CH(COOH)—$R^b$—; wherein $R^a$ is selected from —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$OH, —CH$_2$CH$_2$CH$_2$CO$_2$H, and —CH$_2$CH$_2$CH$_2$CH$_2$CO$_2$H; and $R^b$ is selected from —CH$_2$NH—, —CH$_2$CH$_2$NH—, —CH$_2$CH$_2$CH$_2$NH—, —CH$_2$CH$_2$CH$_2$CH$_2$NH—, —CH$_2$CH$_2$C(O)—, —CH$_2$CH$_2$CH$_2$C(O)—, and —CH$_2$CH$_2$CH$_2$CH$_2$C(O)—.

In embodiments where $R^{L1}$ is present and is an optionally substituted alkylene, it can be a $C_1$-$C_6$ alkylene, optionally substituted with 1-4 substituents selected from —NH—, —C(O)—, —COOH, —N($C_1$-$C_3$ alkyl)-, —NH$_2$ or NH($C_1$-$C_3$ alkyl). In some embodiments, $R^{L1}$ is ethylenediamine, —NH—CH(COOH)—CH$_2$—NH— or —C(O)—CH(CH$_2$NH$_2$)—.

In embodiments where $R^{L2}$ is present and is a hydrophilic amino acid, it can be selected from the group consisting of Glycine; L or D forms of Aspartate, Glutamate, Asparagine, Glutamine, Histidine, Lysine, Arginine, Serine and Alanine; —NH—CH($R^a$)—C(O)—; and —NH—CH(COOH)—$R^b$—; wherein $R^a$ is selected from —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$OH, —CH$_2$CH$_2$CH$_2$CO$_2$H, and —CH$_2$CH$_2$CH$_2$CH$_2$CO$_2$H; and $R^b$ is selected from —CH$_2$NH—, —CH$_2$CH$_2$NH—, —CH$_2$CH$_2$CH$_2$NH—, —CH$_2$CH$_2$CH$_2$CH$_2$NH—, —CH$_2$CH$_2$C(O)—, —CH$_2$CH$_2$CH$_2$C(O)—, and —CH$_2$CH$_2$CH$_2$CH$_2$C(O)—.

In some further embodiments when $R^{L2}$ is present, it is selected from the group consisting of the D amino acids of Aspartate, Glutamate, Asparagine, Glutamine, Histidine, Lysine, Arginine, Serine and Alanine; Glycine; —NH—CH($R^a$)—C(O)—; and —NH—CH(COOH)—$R^b$—; wherein $R^a$ is selected from —CH$_2$NH$_2$—, —CH$_2$CH$_2$NH—, —CH$_2$CH$_2$CH$_2$NH$_2$, —CH$_2$CH$_2$CH$_2$CH$_2$NH$_2$, —CH$_2$CH$_2$OH, —CH$_2$CH$_2$CH$_2$CO$_2$H, and —CH$_2$CH$_2$CH$_2$CH$_2$CO$_2$H; and $R^b$ is selected from —CH$_2$NH—, —CH$_2$CH$_2$NH—, —CH$_2$CH$_2$CH$_2$NH—, —CH$_2$CH$_2$CH$_2$CH$_2$NH—, —CH$_2$CH$_2$C(O)—, —CH$_2$CH$_2$CH$_2$C(O)—, and —CH$_2$CH$_2$CH$_2$CH$_2$C(O)—.

In embodiments where $R^{L2}$ is present and is an optionally substituted alkylene, it can be a $C_1$-$C_6$ alkylene, optionally substituted with 1-4 substituents selected from —NH—, —C(O)—, —COOH, —N($C_1$-$C_3$ alkyl)-, —NH$_2$ or —NH($C_1$-$C_3$ alkyl). In some embodiments, $R^{L3}$ is ethylenediamine, —NH—CH(COOH)—CH$_2$—NH— or —C(O)—CH(CH$_2$NH$_2$)—.

In embodiments where $R^{L3}$ is present, and is a hydrophilic amino acid, it can be selected from the group consisting of Glycine; L or D forms of Aspartate, Glutamate, Asparagine, Glutamine, Histidine, Lysine, Arginine, Serine and Alanine; —NH—CH($R^a$)—C(O)—; and —NH—CH(COOH)—$R^b$—; wherein $R^a$ is selected from —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$—CH$_2$CO$_2$H, and —CH$_2$CH$_2$CH$_2$CH$_2$CO$_2$H; and $R^b$ is selected from —CH$_2$NH—, —CH$_2$CH$_2$NH—, —CH$_2$CH$_2$CH$_2$NH—, —CH$_2$CH$_2$CH$_2$CH$_2$NH—, —CH$_2$CH$_2$C(O)—, —CH$_2$CH$_2$CH$_2$C(O)—, and —CH$_2$CH$_2$CH$_2$CH$_2$C(O)—.

In some further embodiments when $R^{L3}$ is present, it selected from the group consisting of the D amino acids of Aspartate, Glutamate, Asparagine, Glutamine, Histidine, Lysine, Arginine, Serine and Alanine; Glycine; —NH—CH($R^a$)—C(O)—; and —NH—CH(COOH)—$R^b$—; wherein $R^a$ is selected from —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$—, —CH$_2$CH$_2$OH, —CH$_2$CH$_2$CH$_2$CO$_2$H and H$_2$CO$_2$H and —CH$_2$CH$_2$CH$_2$CH$_2$CO$_2$H; and $R^b$ is selected from —CH$_2$NH—, —CH$_2$CH$_2$NH—, —CH$_2$CH$_2$CH$_2$NH—, —CH$_2$CH$_2$CH$_2$CH$_2$NH—, —CH$_2$CH$_2$C(O)—, —CH$_2$CH$_2$CH$_2$C(O)—, and —CH$_2$CH$_2$CH$_2$CH$_2$C(O)—.

In embodiments where $R^{L3}$ present, and is an optionally substituted alkylene, it can be a $C_1$-$C_6$ alkylene, optionally substituted with 1-4 substituents selected from —NH—, —C(O)—, —COOH, —N($C_1$-$C_3$ alkyl)-, —NH$_2$ or —NH ($C_1$-$C_3$ alkyl). In some embodiments, $R^{L3}$ ethylenediamine, —NH—CH(COOH)—CH$_2$—NH— or —C(O)—CH(CH$_2$NH$_2$)—.

In some embodiments of the above, $AA_1$ is present and $R^{L1}$, $R^{L2}$ and $R^{L3}$ are absent.

In some embodiments of the above, $AA_1$ is present, $R^{L1}$ is present and $R^{L2}$ and $R^{L3}$ are absent.

In some embodiments of the above, $AA_1$ is present, $R^{L1}$ is present, $R^{L2}$ is present and $R^{L3}$ is absent.

In some embodiments of the above, $AA_1$ is present, $R^{L1}$ is present, $R^{L2}$ is present and $R^{L3}$ is present.

In some further of the above, $AA_1$ is a hydrophilic amino acid and at least one of $R^{L1}$, $R^{L2}$ and $R^{L3}$ is present and is an optionally substituted alkylene, as set forth above.

In some embodiments of the above, $AA_1$ is Glutamate and at least one of $R^{L1}$, $R^{L2}$ and $R^{L3}$ is present and is an optionally substituted alkylene, as set forth above.

In some embodiments of the above, $AA_1$ is Glutamate, $R^{L1}$ is a hydrophilic amino acid and at least one of $R^{L2}$ and $R^{L3}$ is present and is an optionally substituted alkylene, as set forth above.

In some further embodiments of the above, $AA_1$ and $R^{L1}$ are hydrophilic amino acids and at least one of $R^{L2}$ and $R^{L3}$ is present and is an optionally substituted alkylene, as set forth above.

In some embodiments of the above, $AA_1$ is a hydrophilic amino acid and $R^{L1}$ and optionally $R^{L2}$ are an optionally substituted alkylene, as set forth above.

In some embodiments of the above, $L^H$ does not include a glycine dipeptide (Gly-Gly), tripeptide or tetrapeptide. In some embodiments, $L^H$ does not include the peptide Asn-(D)Lys.

In some embodiments, $L^H$ will include a modified peptide, having from two to four amino. The modified peptide has an amino acid in the 1-position ($AA_1$) that is selected to optimize release of the $D_E$ unit (e.g., by protease cleavage via an amide peptide bond). In one or both of positions $R^{L1}$ and $R^{L2}$ is an amino acid which reverses the orientation of typical N to C linkages of peptides and facilitates attachment of the last amino acid (e.g., $R^{L2}$ or $R^{L3}$) which, prior to attachment of the Ligand unit, includes an α-amino group protected as a maleimide. The amino acid having a reversed N to C linkage is attached to the next group via its side chain. In some embodiments, this amino acid is an alpha amino acid. In other embodiments, it can be a beta or gamma amino acid. In some embodiments, the side chain is selected from $-CH_2NH_2$, $-CH_2CH_2NH_2$, $-CH_2CH_2CH_2NH_2-$, and $-CH_2CH_2CH_2CH_2NH_2$.

In some embodiments of $L^H$, the amino acid having a reversed N to C linkage ($R^{L1}$) is attached to $R^{L2}$ or $R^{L3}$, where $R^{L2}$ or $R^{L3}$ is a hydrophilic amino acid or an optionally substituted alkylene, according to any of the embodiments described above.

In some embodiments of $L^H$, the amino acid having a reversed N to C linkage ($R^{L1}$) is attached to $R^{L2}$, where $R^{L2}$ is an optionally substituted alkylene, according to any of the embodiments described above.

In some further embodiments, $L^H$ is a hydrophilic, cleavable linker, each branch having the formula:

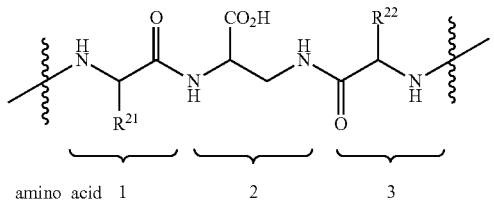

amino acid  1      2      3 wherein $R^{21}$ is selected from $-CH_2NH_2$, $-CH_2CH_2NH_2$, $-CH_2OH$, $-CH_2CH_2OH$, $-CH_2CO_2H$; $-CH_2CH_2CO_2H$, $-CH_2CH_2CH_2CO_2H$ and $-CH_2CH_2CH_2CH_2CO_2H$; and $R^{22}$ is selected from $-CH_2NH_2$, $-CH_2CH_2NH_2$, $-CH_2OH$, and $-CH_2CH_2OH$. The left and right wavy lines indicate attachments to the $D_E$ unit and $L^A$, or the branch of $L^H$, respectively.

In further embodiments. $L^H$, or a branch thereof, has the formula:

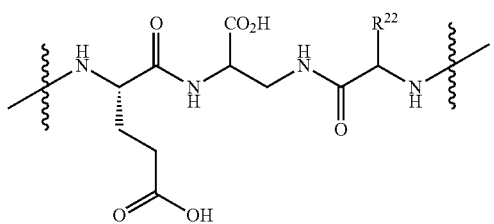

wherein $R^{22}$ is selected from $-CH_2NH_2$, $-CH_2CH_2NH_2$, $-CH_2OH$ and $-CH_2CH_2OH$. In some embodiments, $R^2$ is selected from $-CH_2NH_2$ and $-CH_2CH_2NH_2$. The left and right wavy lines indicate attachments to the $D_E$ unit and $L^A$, respectively.

In certain embodiments, $L^H$, or a branch thereof, has the formula:

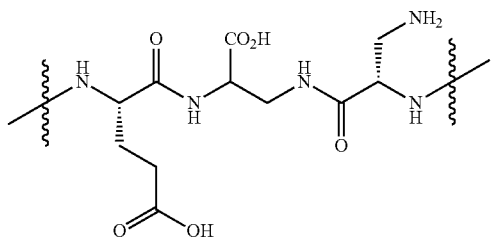

The left and right wavy lines indicate attachments to the $D_E$, unit and $L^A$, or the branch of $L^H$, respectively.

In certain embodiments, $L^H$, or a branch thereof, has the formula:

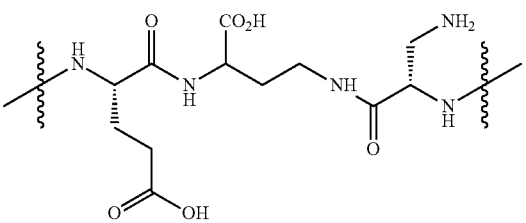

The left and right wavy lines indicate attachments to the $D_E$ unit and $L^A$, or the branch of $L^H$, respectively.

In certain embodiments, $L^H$, or a branch thereof, has the formula:

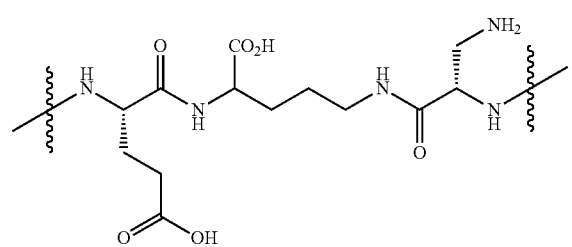

The left and right wavy lines indicate attachments to the $D_E$, unit and $L^A$, or the branch of $L^H$, respectively.

In certain embodiments, $L^H$, or a branch thereof, has the formula:

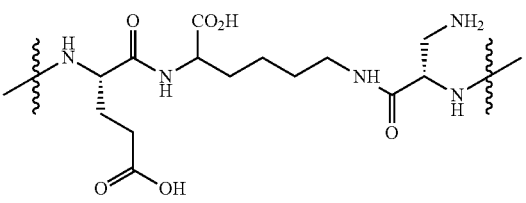

The left and right wavy lines indicate attachments to the $D_E$ unit and $L^A$, or the branch of $L^H$, respectively.

In certain embodiments, $L^H$, or a branch thereof, has the formula:

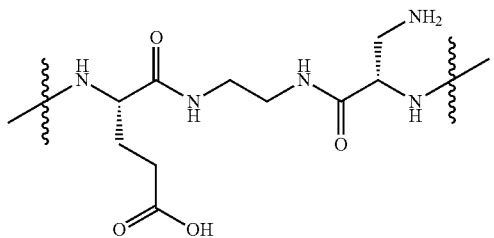

The left and right wavy lines indicate attachments to the $D_E$ unit and $L^A$, respectively.

In certain embodiments, $L^H$, or a branch thereof, has the formula:

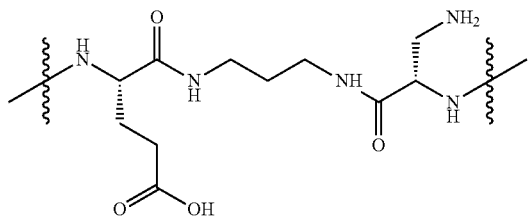

The left and right wavy lines indicate attachments to the $D_E$ unit and $L^A$, or the branch of $L^H$, respectively.

In certain embodiments, $L^H$, or a branch thereof, has the formula:

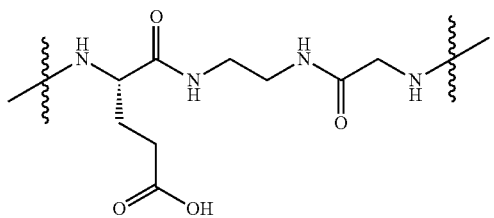 [SMILES: *NCC(=O)NCCNC(=O)[C@H](CCC(=O)O)N*]

The left and right wavy lines indicate attachments to the $D_E$ unit and $L^A$, or the branch of $L^H$, respectively.

In some further embodiments of the above, $L^H$ is a branched hydrophilic linker having the formula:

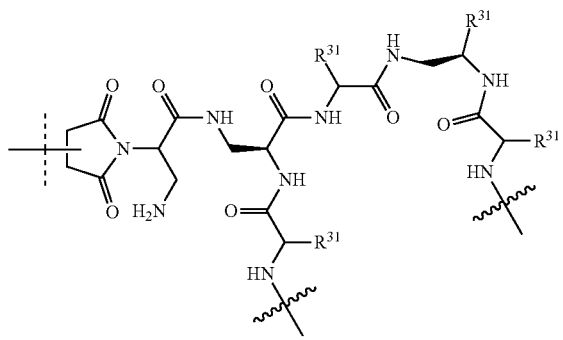

wherein each $R^{31}$ is independently selected from the group consisting of —CH$_2$NH$_2$, —CH$_2$CH$_2$NH$_2$, —CH$_2$OH, —CH$_2$CH$_2$OH, —CH$_2$CO$_2$H, —CH$_2$CH$_2$CO$_2$H, —CH$_2$CH$_2$CH$_2$CO$_2$H, and —CH$_2$CH$_2$CH$_2$CH$_2$CO$_2$H; and each of the bars adjacent the $R^{31}$ indicates an attachment to a $D_E$ unit and the vertical dashed line indicates an attachment to a Ligand unit.

In some further embodiments of the above, $L^H$ is a branched hydrophilic linker having the formula:

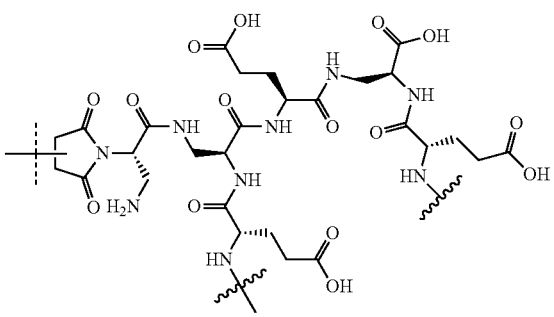

wherein each of the bars indicates attachment to a Drug unit, and the vertical dashed line indicates an attachment to a Ligand unit.

In some further embodiments of the above, a branched hydrophilic linker has the formula:

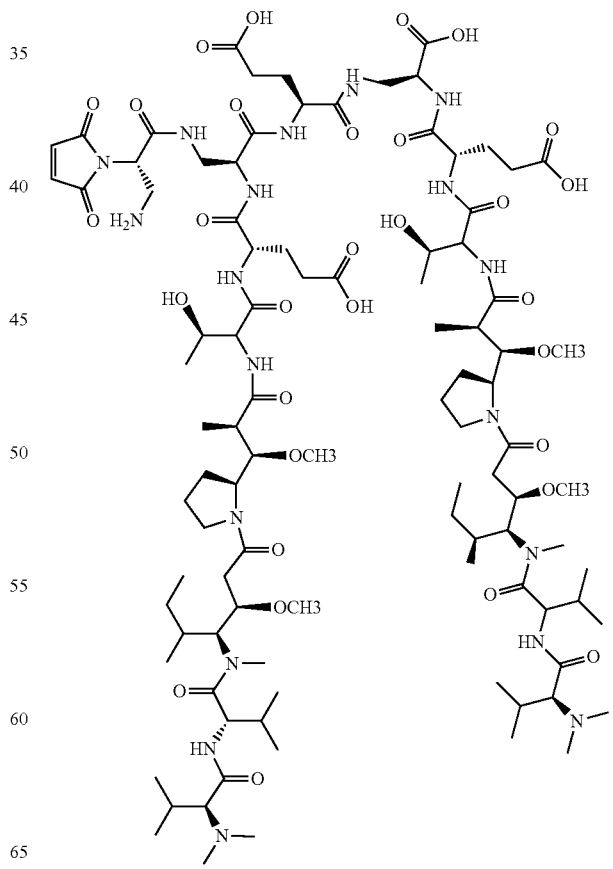

Referring again to the Ligand-Linker-Drug conjugates of formula II, in some further embodiments, the Ligand-Linker-Drug conjugates have a formula selected from:

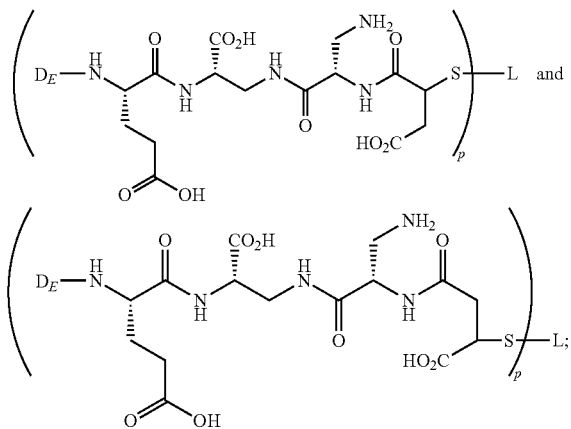

wherein S refers to a sulfur atom of the Ligand.

$L^A$—the Ligand Attachment Component

Referring again to formulas I, and I' (supra), $L^A$ is a Ligand attachment component. In some embodiments, $L^A$ can be a maleimide or a hydrolyzed maleimide or succinimide group (illustrated below as a succinic acid moiety). In some embodiments, wherein $L_A$ is attached to a Ligand unit, it is a hydrolyzed maleimide or succinimide group (illustrated as a succinic acid moiety). Accordingly, in some embodiments, $L^A$ has the formula:

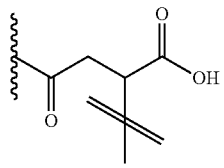

wherein the wavy line indicates the point of attachment to $L^H$ and the \\ indicates the point of attachment to L, the Ligand unit.

In other embodiments, $L^A$ has the formula:

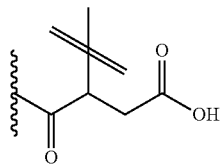

wherein the wavy line indicates the point of attachment to $L^H$ and the \\ indicates the point of attachment to L, the Ligand unit.

In the context of the present invention, in some embodiments (as shown above) $L^A$ is the vestige of a maleimide group used for attachment of the Ligand portion. The design of $L^H$ and $L^A$ allows for facile addition of a Ligand unit, as well as providing an additional carboxylic acid group which increases the hydrophilicity of the Ligand-Drug Conjugate. Still further, the maleimide nitrogen becomes an α-amine of amino acid 3 (with reference to $L^H$).

L—The Ligand

Referring again to foie u as I, I' and II, the Ligand unit (L-) is a targeting agent that specifically binds to a target moiety. The Ligand can specifically bind to a cell component or to other target molecules of interest. The target moiety, or target, is typically on the cell surface. In some aspects, the Ligand unit acts to deliver the Drug unit to the particular target cell population with which the Ligand unit interacts. Ligands include, but are not limited to, proteins, polypeptides and peptides as well as non-proteinaceous agents such as carbohydrates. Suitable Ligand units include, for example, antibodies, e.g., full-length (intact) antibodies, as well as antigen binding fragments thereof.

In embodiments where the Ligand unit is a non-antibody targeting agent, it can be a peptide or polypeptide, or a non-proteinaceous molecule, Examples of such targeting agents include an interferon, a lymphokine, a hormone, a growth factor and a colony-stimulating factor, a vitamin, a nutrient-transport molecule (such as, but not limited to, transferrin), or any other cell binding molecule or substance.

In some embodiments, $L^A$ is covalently linked to a sulfur atom of the Ligand. In some aspects, the sulfur atom is that of a cysteine residue that forms an interchain disulfide bond of an antibody. In another aspect, the sulfur atom is that of a cysteine residue that has been introduced into the Ligand unit (e.g., by site directed mutagenesis or chemical reaction). In further aspects, the sulfur atoms to the $L^A$'s are attached are selected from cysteine residues that form an interchain disulfide bond of an antibody and cysteine residues that have been introduced into the Ligand unit (e.g., by site directed mutagenesis or chemical reaction), In some embodiments, the a cysteine residue is introduced into the Fe region at position 239 according to the EU index numbering system as in Kabat (Kabat E. A. et al. (1991) Sequences of Proteins of Immunological Interest, 5th edition, NIH Publication No 91 3242).

In some aspects, a Ligand unit forms a bond with the maleimide present on $L^H$ via a sulfhydryl group of the Ligand to form a thio-substituted succinimide. The sulfhydryl group can be present on the Ligand in the Ligand's natural state, for example a naturally-occurring antibody, or can be introduced into the Ligand via chemical modification. Hydrolysis of the remaining succinimide produces the $L^A$ portion.

In one aspect, the Ligand unit has one or more lysine residues that can be chemically modified to introduce one or more sulfhydryl groups. The reagents that can be used to modify lysines include, but are not limited to, N-succinimidyl S-acetylthioacetate (SATA) and 2-Iminothiolane hydrochloride (Traut's Reagent).

In another embodiment, the Ligand unit can have one or more carbohydrate groups that can be chemically modified to have one or more sulfhydryl groups.

In another embodiment, the sulfhydryl groups can be generated by reduction of the interchain disulfides. Accordingly, in some embodiments, a Linker unit is conjugated to a cysteine residue of the reduced interchain disulfides.

In another embodiment, the sulfhydryl group is chemically introduced into the antibody, for example by introduction of a cysteine residue. Accordingly, in some embodiments, the Linker unit is conjugated to an introduced cysteine residue.

Useful non-immunoreactive protein, polypeptide, or peptide Ligands include, but are not limited to, transferrin, epidermal growth factors ("EGF"), bombesin, gastrin, gastrin-releasing peptide, platelet-derived growth factor, IL-2, IL-6, transforming growth factors ("TGF"), such as TGF-α and TGF-β, vaccinia growth factor ("VGF"), insulin and insulin-like growth factors I and II, somatostatin, lectins and apoprotein from low density lipoprotein.

Particularly preferred Ligands are antibodies. Useful polyclonal antibodies are heterogeneous populations of antibody molecules derived from the sera of immunized animals. Useful monoclonal antibodies are homogeneous populations of antibodies to a particular antigenic determinant (e.g., to a cancer cell antigen, a viral antigen, a microbial antigen, a protein, a peptide, a carbohydrate, a chemical, nucleic acid, or fragments thereof), A monoclonal antibody (mAb) to an antigen-of-interest can be prepared by using any technique known in the art which provides for the production of antibody molecules by continuous cell lines in culture.

Useful monoclonal antibodies include, but are not limited to, human monoclonal antibodies, humanized monoclonal antibodies, or chimeric human-mouse (or other species) monoclonal antibodies. The antibodies include full-length antibodies and antigen binding fragments thereof. Human monoclonal antibodies may be made by any of numerous techniques known in the art (e.g., Teng et al., 1983, *Proc. Natl. Acad. Sci. USA.* 80:7308-7312; Kozbor et al., 1983, *Immunology Today* 4:72-79; and Olsson et al., 1982, *Meth. Enzymol.* 92:3-16).

The antibody can be an antigen binding fragment, derivative or analog of an antibody that immunospecifically binds to target cells (e.g., cancer cell antigens, viral antigens, or microbial antigens) or other antibody bound to tumor cells or matrix. In this regard, "antigen binding" means that the fragment, derivative or analog is able to specifically bind to the target moiety. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay) (see, e.g., Kabat et al., 1991, *Sequences of Proteins of Immunological Interest*, Fifth Edition, National Institute of Health, Bethesda, Md.; Kabat E et al., 1980, *J. Immunology* 125(3):961-969).

Other useful antibodies include antigen binding fragments of antibodies such as, but not limited to, $F(ab')_2$ fragments, Fab fragments, Fvs, single chain antibodies, diabodies, tribodies, tetrabodies, scFv, scFv-FV, or any other molecule derived from an antibody and having the same specificity as the antibody.

Additionally, recombinant antibodies, such as chimeric and humanized monoclonal antibodies, comprising both human and non-human portions, which can be made using standard recombinant DNA techniques, are useful antibodies, A chimeric antibody is a molecule in which different portions are derived from different animal species, such as for example, those having a variable region derived from a murine monoclonal and human immunoglobulin constant regions. (See, e.g., U.S. Pat. Nos. 4,816,567; and 4,816,397, which are incorporated herein by reference in their entirety.) Humanized antibodies are antibody molecules from non-human species having one or more complementarity determining regions (CDRs) from the non-human species and a framework region derived from a human immunoglobulin molecule. (See, e.g., U.S. Pat. No. 5,585,089, which is incorporated herein by reference in its entirety.) Such chimeric and humanized monoclonal antibodies can be produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., 1988, *Science* 240:10414043; Liu et al., 1987, *Proc. Natl. Acad. Sci. USA* 84:3439-3443; Liu et al., 1987, *J. Immunol.* 139:3521-3526; Sun et al., 1987, *Proc. Natl. Acad. Sci. LISA* 84:214-218; Nishimura et al., 1987, *Cancer. Res.* 47:999-1005; Wood et al., 1985, *Nature* 314:446-449; and Shaw et al., 1988, *J. Natl. Cancer Inst.* 80:1553-1559; Morrison, 1985, *Science* 229:1202-1207; Oi et al., 1986, *BioTechniques* 4:214; U.S. Pat. No. 5,225,539; Jones et al., 1986, *Nature* 321:552-525; Verhoeyan et al., 1988, *Science* 239: 1534; and Beidler et al., 1988, *J. Immunol.* 141:4053-4060; each of which is incorporated herein by reference in its entirety.

Completely human antibodies are particularly desirable and can be produced using transgenic mice that are incapable of expressing endogenous immunoglobulin heavy and light chains variable region genes, but which can express human heavy and light chain variable region genes.

Antibodies can have modifications e.g., substitutions, deletions and/or additions) amino acid residues that interact with Fe receptors. In particular, antibodies can have modifications in amino acid residues identified as involved in the interaction between the anti-Fe domain and the Fail receptor (see, e.g., International Publication No. WO 97/34631 which is incorporated herein by reference in its entirety). Antibodies also can have modifications in amino acid residues identified as involved in the interaction between the anti-Fe domain and the Fe gamma receptor III.

Antibodies immunospecific for a cancer cell antigen can be obtained commercially or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, the literature publications, or by routine cloning and sequencing.

In a specific embodiment, antibodies for the treatment of cancer can be used. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database or a database like it, the literature publications, or by routine cloning and sequencing.

In another specific embodiment, antibodies for the treatment of an autoimmune disease are used in accordance with the compositions and methods of the invention. Antibodies immunospecific for an antigen of a cell that is responsible for producing autoimmune antibodies can be obtained from any organization (e.g., a university scientist or a company) or produced by any method known to one of skill in the art such as, e.g., chemical synthesis or recombinant expression techniques.

In certain embodiments, useful antibodies can bind to a receptor or a receptor complex. The receptor or receptor complex can comprise, for example, an immunoglobulin gene superfamily member, a TNT: receptor superfamily member, an integrin, a cytokine receptor, a chemokine receptor, a major histocompatibility protein, a lectin, or a complement control protein.

In some embodiments, the antibody is a humanized CD70 antibody (see, e.g., US 2009/0148942), a humanized CD19 antibody (see, e.g., US 2009/0136526), a chimeric or humanized CD30 antibody (see, e.g., US 2010/0239571), a humanized CD33 antibody (US 2013/0309223), a humanized Beta6 antibody (see, e.g., WO 2013/123152), or a humanized Liv-1 antibody (see, e.g., US 2013/0259860).

Drag Loading-"p"

Referring again generally to the Ligand-Linker-Drug conjugates of formulas I, I' and II, the number of Drug-Linker units per Ligand is represented by p. (In this context, the drug of the Drug-Linker can be a cytotoxic agent.) In embodiments wherein the linkers are not branched, p represents the number of Drug-Linker molecules per Ligand (e.g., antibody). When referring to individual conjugates, p is an integer representing the number of Drug-Linker molecules per Ligand. When referring to a composition containing multiple conjugates, p represents the average number of Drug-Linkers per Ligand (or in embodiments where the linkers are not branched, the average number of Drug-Linker molecules per Ligand (e.g., antibody)). The variable p ranges from 4 to 20, typically 6 to 12, 8 to 12 or 8 to 16, or up to 20.

The average number of Drug-Linker units per Ligand unit in a preparation from a conjugation reaction may be characterized by conventional means such as mass spectroscopy, ELISA assay, HIC and HPLC. The quantitative distribution of Ligand-Linker-Drug conjugates in terms of p may also be determined. In some instances, separation, purification, and characterization of homogeneous Ligand-Drug Conjugates, where p is a certain value from Ligand-Drug Conjugate with other drug loadings may be achieved by means such as reverse phase HPLC or electrophoresis.

Activity Assays

There are a number of different assays that can be used for determining whether a Ligand-Drug Conjugate exerts a cytotoxic effect on a cell line. In one example for determining whether a Ligand-Drug Conjugate exerts a cytotoxic effect on a cell line, a thymidine incorporation assay is used. For example, cells at a density of 5,000 cells/well of a 96-well plate are cultured for a 72-hour period and exposed to 0.5 µCi of $^3$H-thymidine during the final 8 hours of the 72-hour period, and the incorporation of $^3$H-thymidine into cells of the culture is measured in the presence and absence of Ligand-Drug Conjugate. The Ligand-Drug Conjugate has a cytotoxic effect on the cells if the cells of the culture have reduced $^3$H-thymidine incorporation compared to same cells cultured under the same conditions but not contacted with the Ligand-Drug Conjugate. (See also Klussman et al., *Bioconjugate Chemistry* 15: 765-773 (2004); Doronina et al., *Bioconjugate Chemistry* 17:114-124 (2006).)

In another example, for determining whether a Ligand-Drug Conjugate exerts a cytotoxic effect on a cell line, cell viability is measured by determining in a cell the uptake of a dye such as neutral red, trypan blue, or ALAMAR™ blue (see, e.g., Page et al., 1993, *Intl. J of Oncology* 3:473-476). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytoxicity (Skehan et al., 1990 *J. Nat'l Cancer Inst.* 82:1107-12); Preferred Ligand Drug Conjugates include those with an IC$_{50}$ value (defined as the mAb concentration that gives 50% cell kill) of less than 1000 ng/ml, preferably less than 500 ng/ml, more preferably less than 100 ng/ml, even most preferably less than 50 or even less than 10 rig/nil on the cell line;

Drug-Linker Compounds

In another aspect, Drug-Linker compounds are provided, having the formula:

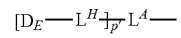

IV or a pharmaceutically acceptable salt or solvate thereof, wherein:

$L^A$ is a Ligand attachment component;

$L^H$ is an optionally branched hydrophilic linker, each branch having the formula:

-AA$_1$-R$^{L1}$—R$^{L2}$—R$^{L3}$— wherein:

AA$_1$ is a hydrophilic amino acid that forms a cleavable bond with the C-terminal end of the D$_E$ unit to which it is attached;

R$^{L1}$ is optional and is a hydrophilic amino acid or an optionally substituted alkylene, which may share an atom with $L^A$ when R$^{L1}$ is present and R$^{L2}$ and R$^{L3}$ are absent;

R$^{L2}$ is optional and is selected from a hydrophilic amino acid and an optionally substituted alkylene, which may share an atom with $L^A$ when R$^{L2}$ is present and R$^{L3}$ is absent; and R$^{L3}$ is optional and is selected from a hydrophilic amino acid and an optionally substituted alkylene, which may share an atom with $L^A$ when R$^{L3}$ is present;

the subscript p' is an integer of from 1 to 4; and

D$_E$ is an effector moiety (as described herein);

wherein a Ligand-Linker-Drug conjugate formed with the Drug-Linkers has a hydrophilicity index of less than or equal to 2; and wherein the left and right lines of $L^H$ indicate covalent attachments to the D$_E$ unit and $L^A$, respectively.

In related aspect IV', Drug-Linker compounds having the following formula are provided:

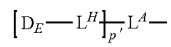

IV' or a pharmaceutically acceptable salt or solvate thereof, wherein:

$L^A$ is a. Ligand attachment component;

$L^H$ is an optionally branched hydrophilic linker having the formula:

-AA$_1$-R$^{L1}$—R$^{L2}$—R$^{L3}$— wherein:

AA$_1$ is a hydrophilic amino acid that forms a cleavable bond with the C-terminal end of the D$_F$ unit to which it is attached;

R$^{L1}$ is a hydrophilic amino acid or an optionally substituted alkylene, which may share an atom with $L^A$ when R$^{L3}$ and R$^{L3}$ are not present;

R$^{L2}$ is optional and is selected from a hydrophilic amino acid and an optionally substituted alkylene, which may share an atom with $L^A$ when R$^{L2}$ is present and R$^{L3}$ is not present; and $R^{L3}$ is optional and is selected from a hydrophilic amino acid and an optionally substituted alkylene, which may share an atom with $L_A$ when $R^{L3}$ is present;

$L^A$ is a Ligand attachment component;

the subscript p' is an integer of from 1 to 4;

and $D_E$ is an effector moiety (as described herein);

wherein the Ligand-Linker-Drug conjugates formed of the Drug-Linkers have a hydrophilicity index of less than or equal to 2;

wherein the left and right lines of $L^H$ indicate covalent attachments to the $D_E$ unit and $L^A$, respectively.

Various components of the Ligand-Linker-Drug conjugates of formulas IV and IV' are provided in more detail below.

Drug Unit, $D_E$

Referring to the formulas IV and IV', the Drug Unit, $D_E$, is an effector moiety having the formula:

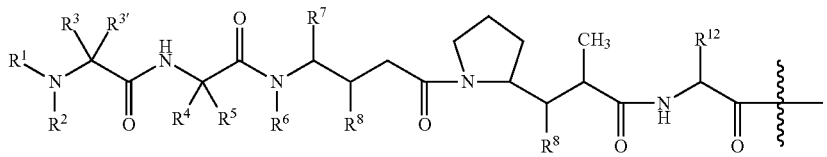

wherein:

$R^1$ and $R^2$ each are independently selected from the group consisting of hydrogen (H) and optionally substituted —$C_1$-$C_8$ alkyl; with the proviso that both $R^1$ and $R^2$ are not H, unless both of $R^3$ and $R^{3'}$ are not H;

$R^3$ is selected from the group consisting of H and optionally substituted —$C_1$-$C_8$ alkyl, $R^{3'}$ is selected from the group consisting of H and optionally substituted —$C_1$-$C_8$ alkyl, and at least one of $R^3$ and $R^{3'}$ is not H;

$R^4$ is selected from the group consisting of H and optionally substituted —$C_1$-$C_8$ alkyl;

$R^5$ is selected from the group consisting of H and optionally substituted —$C_1$-$C_8$ alkyl;

or $R^4$ and $R^5$ jointly form a carbocyclic ring and have the formula —$(CR^aR^b)_n$—, wherein $R^a$ and $R^b$ are independently selected from the group consisting of H and optionally substituted —$C_1$-$C_8$ alkyl and n is selected from the group consisting of 2, 3, 4, 5 and 6;

$R^6$ is selected from the group consisting of H and optionally substituted —$C_1$-$C_8$ alkyl;

$R^7$ is selected from the group consisting of H and optionally substituted —$C_1$-$C_8$ alkyl;

each $R^8$ is independently selected from the group consisting of H, —OH, optionally substituted —$C_1$-$C_8$ alkyl, and optionally substituted —O—($C_1$-$C_8$ alkyl);

$R^{12}$ is selected from H, optionally substituted —$C_1$-$C_8$ alkyl, optionally substituted aryl, optionally substituted —$X^1$aryl, optionally substituted —$C_3$-$C_8$ carbocycle, optionally substituted —$X^1$—($C_3$-$C_8$ carbocycle), optionally substituted —$C_1$-$C_8$ alkylene-$NH_2$, optionally substituted —$C_3$-$C_8$ heterocycle and optionally substituted —$X^1$—($C_3$-$C_8$ heterocycle); and each $X^1$ is independently $C_1$-$C_{10}$ alkylene.

In some related embodiments, $R^{12}$ is not the side chain of phenylalanine or proline. In some further related embodiments, $R^{12}$ is not the side chain of phenylalanine, methionine, tryptophan or proline.

In some embodiments, $R^{12}$ is selected from the side chains of natural L-amino acids (other than proline) and glycine. In some further embodiments, $R^{12}$ is selected from the side chains of natural L-amino acids, other than proline, glycine or phenylalanine. In some further embodiments, $R^{12}$ is selected from the side chains of natural L-amino acids, other than proline, glycine, tryptophan, methionine or phenylalanine.

In some further embodiments, $R^{12}$ is selected from the side chains of the group of hydrophilic amino acids consisting of threonine, serine, asparagine, aspartic acid, glutamine, glutamic acid, homoserine, hydroxyvaline, furyl alanine, threonine($PO_3H_2$), pyrazolyl alanine, triazolyl alanine and thiazolyl alanine.

In some embodiments, $R^{12}$ is the side chain of threonine.

The Linker Unit

Referring to the Linker unit of formulas IV and IV', in some embodiments, $L^A$ is covalently linked to a sulfur atom of the Ligand. In some aspects, the sulfur atom is that of a cysteine residue that forms an interchain disulfide bond of an antibody. In another aspect, the sulfur atom is that of a cysteine residue that has been introduced into the Ligand unit (e.g., by site directed mutagenesis or chemical reaction). In further aspects, the sulfur atoms to which the $L^A$'s are attached are selected from cysteine residues that form an interchain disulfide bond of an antibody and cysteine residues that have been introduced into the Ligand unit (e.g., by site directed mutagenesis or chemical reaction).

$AA_1$ forms a cleavable bond with the effector moiety, $D_E$, such as a Drug unit. In embodiments where $AA_1$ is attached to an amino acid of $D_E$, $AA_1$ forms a cleavable peptide bond with $D_E$. The cleavable peptide bond is susceptible to cleavage by proteases when the conjugate reaches its target site. In other embodiments, $AA_1$ forms an amide bond with an attachment site of the effector moiety that is susceptible to cleavage (e.g., by proteases) when the conjugate reaches its targeted site. In some embodiments, $AA_1$ is a hydrophilic amino acid, typically a natural amino acid that is selected from the group consisting of Glycine and L forms of Aspartate, Glutamate, Asparagine, Glutamine, Histidine, Lysine, Arginine, Serine and Alanine. In some embodiments, $AA_1$ is Glutamate.

In embodiments where $R^{L1}$ is present and is a hydrophilic amino acid, it can be selected from the group consisting of Glycine; L or D forms of Aspartate, Glutamate, Asparagine, Glutamine, Histidine, Lysine, Arginine, Serine and Alanine; —NH—CH($R^a$)—C(O)—; and —NH—CH(COOH)—$R^b$—; wherein $R^a$ is selected from —$CH_2NH_2$, —$CH_2CH_2NH_2$, —$CH_2CH_2CH_2NH_2$, —$CH_2CH_2CH_2CH_2NH_2$, —$CH_2CH_2OH$, —$CH_2CH_2CH_2CO_2H$, and —$CH_2CH_2CH_2CH_2CO_2H$; and $R^b$ is selected from —$CH_2NH$—, —$CH_2CH_2NH$—, —$CH_2CH_2$—$CH_2NH$—, —$CH_2CH_2CH_2CH_2NH$—, —$CH_2CH_2C(O)$—, —$CH_2CH_2CH_2C(O)$—, and —$CH_2CH_2CH_2CH_2C(O)$—. In some further embodiments, $R^{L1}$ is selected from the group consisting of D amino acids of Aspartate, Glutamate, Asparagine, Glutamine, Histidine, Lysine, Arginine, Serine and Alanine; Glycine; —NH—CH($R^a$)—C(O)—; and —NH—CH(COOH)—$R^b$—; wherein $R^a$ is selected from —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$OH—, —CH$_2$CH$_2$CH$_2$CO$_2$H, and —CH$_2$CH$_2$CH$_2$CH$_2$CO$_2$H; and $R^b$ is selected from —CH$_2$NH—, —CH$_2$CH$_2$NH—, —CH$_2$CH$_2$CH$_2$NH—, —CH$_2$CH$_2$CH$_2$CH$_2$NH—, —CH$_2$CH$_2$C(O)—, —CH$_2$CH$_2$CH$_2$C(O)—, and —CH$_2$CH$_2$CH$_2$CH$_2$C(O)—.

In embodiments where $R^{L1}$ is present and is an optionally substituted alkylene, it can be a $C_1$-$C_6$ alkylene, optionally substituted with 1-4 substituents selected from —NH—, —C(O)—, —COOH, —N($C_1$-$C_3$ alkyl)-, —NH$_2$ or —NH($C_1$-$C_3$ alkyl). In some embodiments, $R^{L1}$ is ethylenediamine, —NH—CH(COOH)—CH$_2$—NH— or —C(O)—CH(CH$_2$NH$_2$)—.

In embodiments where $R^{L2}$ is present and is a hydrophilic amino acid, it can be selected from the group consisting of Glycine; L or D forms of Aspartate, Glutamate, Asparagine, Glutamine, Histidine, Lysine, Arginine, Serine and Alanine; —NH—CH($R^a$)—C(O)—; and —NH—CH(COOH)—$R^b$—; wherein $R^a$ is selected from —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$OH, —CH$_2$CH$_2$CH$_2$CO$_2$H, and —CH$_2$CH$_2$CH$_2$CH$_2$CO$_2$H; and $R^b$ is selected from —CH$_2$NH—, —CH$_2$CH$_2$NH—, —CH$_2$CH$_2$CH$_2$NH—, —CH$_2$CH$_2$CH$_2$CH$_2$NH—, —CH$_2$CH$_2$C(O)—, —CH$_2$CH$_2$CH$_2$C(O)—, and —CH$_2$CH$_2$CH$_2$CH$_2$C(O)—.

In some further embodiments when $R^{L2}$ is present, it selected from the group consisting of the D amino acids of Aspartate, Glutamate, Asparagine, Glutamine, Histidine, Lysine, Arginine, Serine and Alanine; Glycine; —NH—CH($R^a$)—C(O)—; and —NH—CH(COOH)—$R^b$—; wherein $R^a$ is selected from —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$OH, —CH$_2$CH$_2$CH$_2$CO$_2$H, and —CH$_2$CH$_2$CH$_2$CH$_2$CO$_2$H; and $R^b$ is selected from —CH$_2$NH—, —CH$_2$CH$_2$NH—, —CH$_2$CH$_2$CH$_2$NH—, —CH$_2$CH$_2$CH$_2$CH$_2$NH—, —C$_2$CH$_2$C(O)—, —CH$_2$CH$_2$CH$_2$C(O)—, and —CH$_2$CH$_2$CH$_2$CH$_2$C(O)—.

In embodiments where R' is present and is an optionally substituted alkylene, it can be a $C_1$-$C_6$ alkylene, optionally substituted with 1-4 substituents selected from —NH—, —C(O)—, —COOH, —N($C_1$-$C_3$ alkyl)-, —NH$_2$ or NH($C_1$-$C_3$ alkyl). In some embodiments, $R^{L2}$ is ethylenediamine, —NH—CH(COOH)—CH$_2$—NH— or —C(O)—CH(CH$_2$NH$_2$)—.

In embodiments where $R^{L3}$ is present, and is a hydrophilic amino acid, it can be selected from the group consisting of Glycine; L or D forms of Aspartate, Glutamate, Asparagine, Glutamine, Histidine, Lysine, Arginine, Serine and Alanine; —NH—CH($R^a$)—C(O)—; and —NH—CH(COOH)—$R^b$—; wherein $R^a$ is selected. from —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$OH, —CH$_2$CH$_2$CH$_2$CO$_2$H, and —CH$_2$CH$_2$CH$_2$CH$_2$CO$_2$H; and $R^b$ is selected from —CH$_2$NH—, —CH$_2$CH$_2$NH—, —CH$_2$CH$_2$CH$_2$NH—, —CH$_2$CH$_2$CH$_2$CH$_2$NH—, —CH$_2$CH$_2$C(O)—, —CH$_2$CH$_2$CH$_2$C(O)—, and —CH$_2$CH$_2$CH$_2$CH$_2$C(O)—.

In some further embodiments when $R^{L3}$ is present, it is selected from the group consisting of the D amino acids of Aspartate, Glutamate, Asparagine, Glutamine, Histidine, Lysine, Arginine, Serine and Alanine; Glycine; —NH—CH($R^a$)—C(O)—; and —NH—CH(COOH)—$R^b$—; wherein $R^a$ is selected from —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$OH, —CH$_2$CH$_2$CH$_2$CO$_2$H, and —CH$_2$CH$_2$CH$_2$CH$_2$CO$_2$H; and $R^b$ is selected from —CH$_2$NH—, —CH$_2$CH$_2$NH—, —CH$_2$CH$_2$CH$_2$NH—, —CH$_2$CH$_2$CH$_2$CH$_2$NH—, —CH$_2$CH$_2$C(O)—, —CH$_2$CH$_2$CH$_2$C(O)—, and —CH$_2$CH$_2$CH$_2$CH$_2$C(O)—.

In embodiments where $R^{L3}$ is present and is an optionally substituted alkylene, it can be a $C_1$-$C_6$ alkylene, optionally substituted with 1-4 substituents selected from —NH—, —C(O)—, —COOH, —N($C_1$-$C_3$ alkyl)-, —NH$_2$ or —NH—($C_1$-$C_3$ alkyl). In some embodiments, $R^{L3}$ is ethylenediamine, —NH—CH(COOH)—CH$_2$—NH— or —C(O)—CH(CH$_2$NH$_2$)—.

In some embodiments of the above, $AA_1$ is present and $R^{L1}$, $R^{L2}$ and $R^{L3}$ are absent.

Ira some embodiments of the above, $AA_1$ is present, $R^{L1}$ is present and $R^{L2}$ and $R^{L3}$ are absent.

In some embodiments of the above, $AA_1$ is present, $R^{L1}$ is present, $R^{L2}$ is present and $R^{L3}$ is absent.

In some embodiments the above, $AA_1$ is present, $R^{L1}$ is present, $R^{L2}$ is present and $R^{L3}$ is present.

In some embodiments of the above, $AA_1$ is a hydrophilic amino acid and at least one of $R^{L1}$, $R^{L2}$ and $R^{L3}$ is present and is an optionally substituted alkylene, as set forth above.

In some embodiments of the above, $AA_1$ is Glutamate and at least one of $R^{L1}$, $R^{L2}$ and $R^{L3}$ is present and is an optionally substituted alkylene, as set forth above.

In some embodiments of the above, $AA_1$ is Glutamate, $R^{L1}$ is a hydrophilic amino acid and at least one of $R^{L2}$ and $R^{L3}$ is present and is an optionally substituted alkylene, as set forth above.

In some embodiments of the above, $AA_1$ and $R^{L1}$ are hydrophilic amino acids and at least one of $R^{L2}$ and $R^{L3}$ is present and is an optionally substituted alkylene, as set forth above.

In some embodiments of the above, $AA_1$ is a hydrophilic amino acid and $R^{L1}$ and optionally $R^{L2}$ are an optionally substituted alkylene, as set forth above.

In some embodiments of the above, $L^H$ does not include a glycine dipeptide (Gly-Gly), tripeptide or tetrapeptide. In some embodiments, $L^H$ does not include the peptide Asn-(D)Lys.

In some embodiments, $L^H$ will include a modified peptide, having twin two to four amino acids. The modified peptide has an amino acid in the 1-position ($AA_1$) that is selected to optimize release of the $D_E$ unit (e.g., by protease cleavage via an amide peptide bond). In one or both of positions $R^{L1}$ and $R^{L2}$ is an amino acid which reverses the orientation of typical N to C linkages of peptides and facilitates attachment of the last amino acid (e.g., $R^{L2}$ or $R^{L3}$) which, prior to attachment of the Ligand unit, includes an α-amino group protected as a maleimide. The amino acid having a reversed N to C linkage is attached to the next group via its side chain. In some embodiments, this amino acid is an alpha amino acid. In other embodiments, it can be a beta or gamma amino acid. In some of these embodiments, the side chain is selected from —CH$_2$NH$_2$—, —CH$_2$—CH$_2$NH$_2$—, —CH$_2$CH$_2$CH$_2$NH$_2$—, and —CH$_2$CH$_2$CH$_2$CH$_2$NH$_2$—.

In some embodiments of $L^H$, the amino acid having a reversed N tea C linkage ($R^{L1}$) is attached to $R^{L2}$ or $R^{L3}$, where $R^{L2}$ or $R^{L3}$ is a hydrophilic amino acid or an optionally substituted alkylene, according to any of the embodiments described above.

In some embodiments of $L^H$, the amino acid having a reversed N to C linkage ($R^{L1}$) is attached to $R^{L2}$, where $R^{L2}$ is an optionally substituted alkylene, according to any of the embodiments described above.

In some further embodiments, $L^H$ is a hydrophilic, cleavable linker, each branch having the formula:

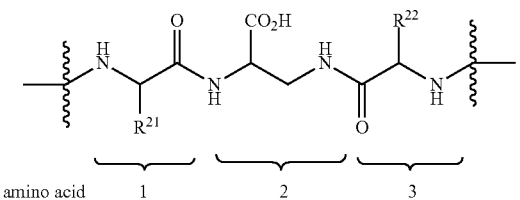

amino acid    1    2    3 wherein $R^{21}$ is selected from —$CH_2NH_2$, —$CH_2CH_2NH_2$, —$CH_2OH$, —$CH_2CH_2OH$, —$CH_2CO_2H$, —$CH_2CH_2CO_2H$, —$CH_2CH_2CH_2CO_2H$, and —$CH_2CH_2CH_2CH_2CO_2H$; and $R^{22}$ is selected from —$CH_2NH_2$, —$CH_2CH_2NH_2$, —$CH_2OH$, and —$CH_2CH_2OH$. The left and right wavy lines indicate attachments to the $D_E$ unit and $L^A$, respectively.

In further embodiments $L^H$, or a branch thereof, has the formula:

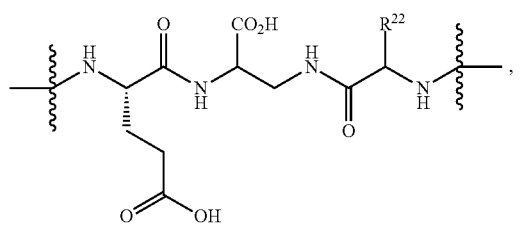

wherein $R^{22}$ is selected from —$CH_2NH_2$, —$CH_2CH_2NH_2$, —$CH_2OH$, and —$CH_2CH_2OH$. In some embodiments, $R^{22}$ is selected from —$CH_2NH_2$ and —$CH_2CH_2NH_2$. The left and right wavy lines indicate attachments to the $D_E$ unit and $L^A$, respectively.

In certain embodiments, or a branch thereof, has the formula:

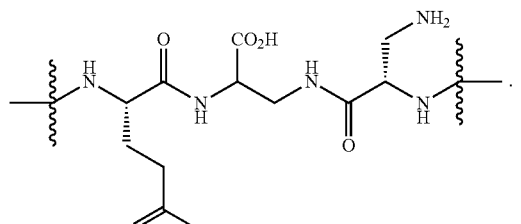

The left and right wavy lines indicate attachments to the $D_E$ unit and $L^A$, respectively.

In certain embodiments, $L^H$, or a branch thereof, has the formula:

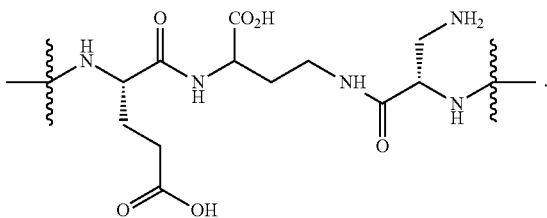 [SMILES: *N[C@@H](CN)C(=O)NCCC(NC(=O)[C@H](CCC(=O)O)N*)C(=O)O]

The left and right wavy lines indicate attachments to the $D_E$ unit and $L^A$, respectively.

In certain embodiments, $L^H$, or a branch thereof, has the formula:

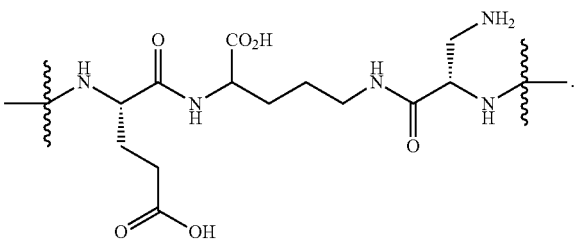 [SMILES: *N[C@@H](CN)C(=O)NCCCC(NC(=O)[C@H](CCC(=O)O)N*)C(=O)O]

The left and right wavy lines indicate attachments to the $D_E$, unit and $L^A$, respectively.

In certain embodiments, $L^H$, or a branch thereof, has the formula:

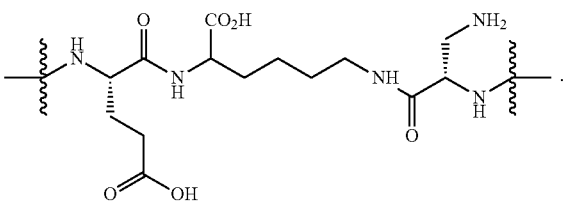 [SMILES: *N[C@@H](CN)C(=O)NCCCCC(NC(=O)[C@H](CCC(=O)O)N*)C(=O)O]

The left and right wavy lines indicate attachments to the $D_E$ unit and $L^A$, respectively.

In certain embodiments, $L^H$, or a branch thereof, has the formula:

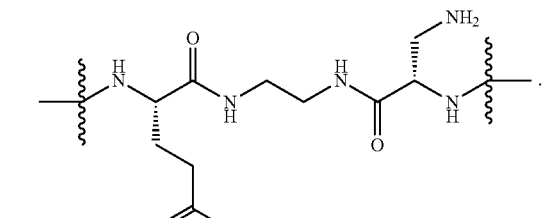

The left and right wavy lines indicate attachments to the $D_E$ unit and $L^A$, respectively.

In certain embodiments, $L^H$, or a branch thereof, has the formula:

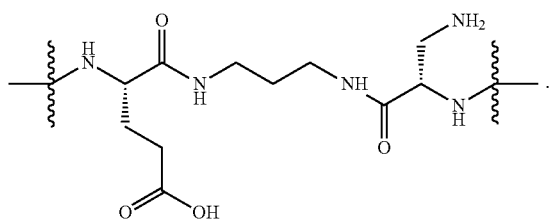 [SMILES: *N[C@@H](CN)C(=O)NCCCNC(=O)[C@H](CCC(=O)O)N*]

The left and right wavy lines indicate attachments to the $D_E$ unit and $L^A$, respectively.

In certain embodiments, $L^H$, or a branch thereof, has the formula:

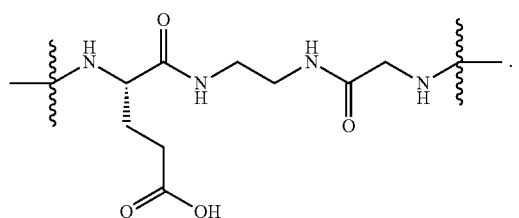 [SMILES: *NCC(=O)NCCNC(=O)[C@H](CCC(=O)O)N*]

The left and right wavy lines indicate attachments to the $D_E$ unit and $L^A$, respectively.

In some further embodiments of the above, $L^H$ is a branched hydrophilic linker having the formula:

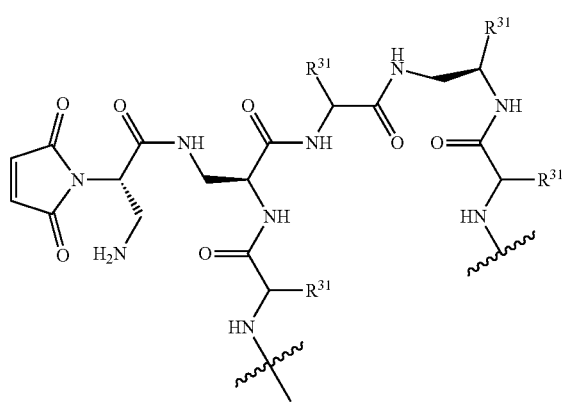

wherein each $R^{31}$ is independently selected from the group consisting of —CH$_2$NH$_2$, —CH$_2$CH$_2$NH$_2$, —CH$_2$OH, —CH$_2$CH$_2$OH, —CH$_2$CO$_2$H, —CH$_2$CH$_2$CO$_2$H, —CH$_2$CH$_2$CH$_2$CO$_2$H, and —CH$_2$CH$_2$CH$_2$CH$_2$CO$_2$H; and each of the bars indicate attachment site for a $D_E$ unit.

In some further embodiments of the above, $L^H$ is a branched hydrophilic linker having the formula:

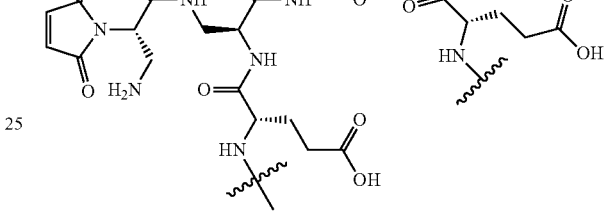

wherein each of the bars indicates attachment to a $D_E$ unit.

The $L^A$ subunit is described in more detail above.

Referring again to the Drug Linker conjugates of formulas IV and IV', in some further embodiments, the Drug-Linkers have a formula selected from:

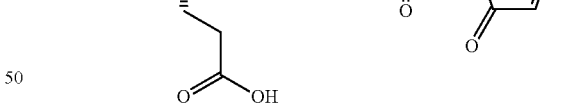

Specific embodiments include the following:

(IVa)

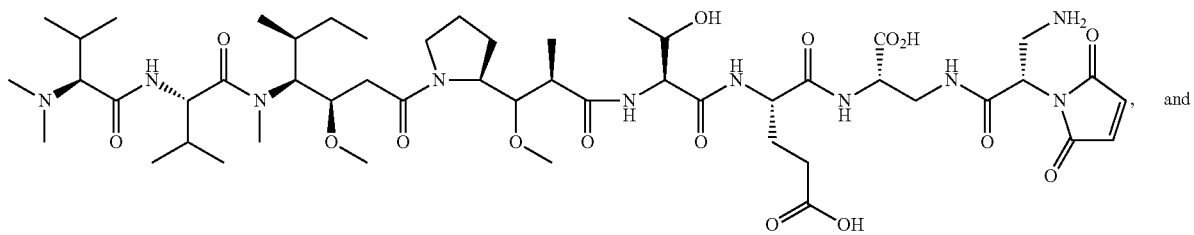

and

-continued

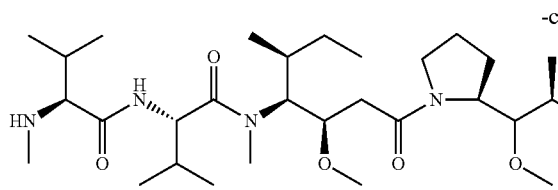 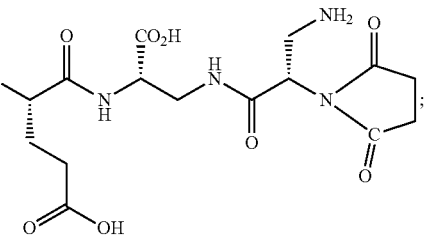

;

or a pharmaceutically acceptable salt or solvate thereof.

Linkers

In another aspect, hydrophilic linkers are provided having the formula:

$$(L^H)_{p'}\text{-}L^A \qquad (VII)$$

wherein:

$L^H$ is an optionally branched hydrophilic linker having the formula:

$$\text{-AA}_1\text{-}R^{L1}\text{—}R^{L2}\text{—}R^{L3}\text{—};$$

$L^A$ is a Ligand Attachment component; and p' is an integer from 1 to 4; and the left and right lines of $L^{Fi}$ indicate attachment sites for a $D_E$ unit and $L^A$, respectively;

or a pharmaceutically acceptable salt or solvate thereof.

Referring to Formula VII, in some embodiments, $L^A$ is covalently linked to a sulfur atom of the Ligand. $L^A$ can be, for example, a maleimide or succimimide, suitable for attachment to a sulfur atom.

$AA_1$ can form a cleavable bond with an effector moiety $D_E$, such as a Drug unit. In embodiments where $AA_1$ is attached to an amino acid of $D_E$, $AA_1$ forms a cleavable peptide bond with $D_E$. The cleavable peptide bond is susceptible to cleavage by proteases when the conjugate reaches its target site. In other embodiments, $AA_1$ forms an amide bond with an attachment site of the effector moiety that is susceptible to cleavage (e.g., by proteases) when the conjugate reaches its target site. In some embodiments, $AA_1$ is a hydrophilic amino acid, typically a natural amino acid that is selected from the group consisting of Glycine and L forms of Aspartate, Glutamate, Asparagine, Glutamine, Histidine, Lysine, Arginine, Serine and Alanine. In some embodiments, $AA_1$ is Glutamate.

In embodiments where $R^{L1}$ is present and is a hydrophilic amino acid, it can be selected
from the group consisting of Glycine; L or D forms of Aspartate, Glutamate, Asparagine, Glutamine, Histidine, Lysine, Arginine, Serine and Alanine; —NH—CH($R^a$)—C(O)—; and —NH—CH(COOH)—$R^b$—; wherein $R^a$ is selected
from —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$OH, —CH$_2$CH$_2$CH$_2$CO$_2$H, and —CH$_2$CH$_2$CH$_2$CH$_2$CO$_2$H; and $R^b$ is selected
from —CH$_2$NH—, —CH$_2$CH$_2$NH—, —CH$_2$CH$_2$CH$_2$NH—, —CH$_2$CH$_2$CH$_2$CH$_2$NH—, —CH$_2$CH$_2$C(O)—, —CH$_2$CH$_2$CH$_2$C(O)—, and —CH$_2$CH$_2$CH$_2$CH$_2$C(O)—. In some further embodiments, $R^{L1}$ is selected from the group consisting of the D amino acids of Aspartate, Glutamate, Asparagine, Glutamine, Histidine, Lysine, Arginine, Serine and Alanine; Glycine; —NH—CH($R^a$)—C(O)—; and —NH—CH(COOH)—$R^b$—; wherein $R^a$ is selected
from —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$OH, —CH$_2$CH$_2$CH$_2$CO$_2$H, and —CH$_2$CH$_2$CH$_2$CH$_2$CO$_2$H; and $R^b$ is selected
from —CH$_2$NH—, —CH$_2$CH$_2$NH—, —CH$_2$CH$_2$CH$_2$NH—, —CH$_2$CH$_2$CH$_2$CH$_2$NH—, —CH$_2$CH$_2$C(O)—, —CH$_2$CH$_2$CH$_2$C(O)—, and —CH$_2$CH$_2$CH$_2$CH$_2$C(O)—.

In embodiments where $R^{L1}$ is present and is an optionally substituted alkylene, it can be a $C_1$-$C_6$ alkylene, optionally substituted with 1-4 substituents selected from —NH—, —C(O)—, —COOH, —N($C_1$-$C_3$ alkyl), —NH$_2$ or —NH ($C_1$-$C_3$ alkyl). In some embodiments, $R^{L1}$ is ethylenediamine, —NH—CH(COOH)—CH$_2$—NH— or —C(O)—CH(CH$_2$NH$_2$)—.

In embodiments where $R^{L2}$ is present and is a hydrophilic amino acid, it can be selected
from the group consisting of Glycine; L or D forms of Aspartate, Glutamate, Asparagine, Glutamine, Histidine, Lysine, Arginine, Serine and Alanine; —NH—CH($R^a$)—C(O)—; and —NH—CH(COOH)—$R^b$—; wherein $R^a$ is selected
from —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$OH, —CH$_2$CH$_2$CH$_2$CO$_2$H, and —CH$_2$CH$_2$CH$_2$CH$_2$CO$_2$H; and $R^b$ is selected
from —CH$_2$NH—, —CH$_2$CH$_2$NH—, —CH$_2$CH$_2$CH$_2$NH—, —CH$_2$CH$_2$CH$_2$CH$_2$NH—, —CH$_2$CH$_2$C(O)—, —CH$_2$CH$_2$CH$_2$C(O)—, and —CH$_2$CH$_2$CH$_2$CH$_2$C(O)—. In some further embodiments when $R^{L2}$ is present, it is selected from the group consisting of the D amino acids of Aspartate, Glutamate, Asparagine, Glutamine, Histidine, Lysine, Arginine, Serine and Alanine; Glycine; —NH—CH($R^a$)—C(O)—; and —NH—CH(COOH)—$R^b$—; wherein $R^a$ is selected.
from —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$OH, —CH$_2$CH$_2$CH$_2$CO$_2$H, and —CH$_2$CH$_2$CH$_2$CH$_2$CO$_2$H; and $R^b$ is selected
from —CH$_2$NH—, —CH$_2$CH$_2$NH—, —CH$_2$CH$_2$CH$_2$NH—, —CH$_2$CH$_2$CH$_2$CH$_2$NH—, —CH$_2$CH$_2$C(O)—, —CH$_2$CH$_2$CH$_2$C(O)—, and —CH$_2$CH$_2$CH$_2$CH$_2$C(O)—.

In embodiments where $R^{L2}$ is present and is an optionally substituted alkylene, it can be a $C_1$-$C_6$ alkylene, optionally substituted with 1-4 substituents selected from —NH—, —C(O)—, —COOH, —N($C_1$-$C_3$ alkyl)-, —NH or —NH($C_1$-$C_3$ alkyl). In some embodiments, $R^{L2}$ is ethylenediamine, —NH—CH(COOH)—CH$_2$—NH— or —C(O)—CH(CH$_2$NH$_2$)—.

In embodiments where $R^{L3}$ is present, and is a hydrophilic amino acid, it can be selected from the group consisting of Glycine; L or D forms of Aspartate, Glutamate, Asparagine, Glutamine, Histidine, Lysine, Arginine, Serine and Alanine; —NH—CH($R^a$)—C(O)—; and —NH—CH(COOH)—$R^b$—; wherein $R^a$ is selected from —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$OH, —CH$_2$CH$_2$CH$_2$CO$_2$H, and —CH$_2$CH$_2$CH$_2$CH$_2$CO$_2$H; and $R^b$ is selected from —CH$_2$NH—, —CH$_2$CH$_2$NH—, —CH$_2$CH$_2$CH$_2$NH—, —CH$_2$CH$_2$CH$_2$CH$_2$NH—, —CH$_2$CH$_2$C(O)—, —CH$_2$CH$_2$CH$_2$C(O)—, and —CH$_2$CH$_2$CH$_2$CH$_2$C(O)—.

In some further embodiments when $R^{L3}$ is present, it is selected from the group consisting of the 1) amino acids of Aspartate, Glutamate, Asparagine, Glutamine, Histidine, Lysine, Arginine, Serine and Alanine; Glycine; —NH—CH($R^a$)—C(O)—; and —NH—CH(COOH)—$R^b$—; wherein $R^a$ is selected from —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$OH, —CH$_2$CH$_2$CH$_2$CO$_2$H, and —CH$_2$CH$_2$CH$_2$CH$_2$CO$_2$H; and $R^b$ is selected from —CH$_2$NH—, —CH$_2$CH$_2$NH—, —CH$_2$CH$_2$CH$_2$NH—, —CH$_2$CH$_2$CH$_2$CH$_2$NH—, —CH$_2$CH$_2$C(O)—, —CH$_2$CH$_2$CH$_2$C(O)—, and —CH$_2$CH$_2$CH$_2$CH$_2$C(O)—.

In embodiments where $R^{L3}$ is present and is an optionally substituted alkylene, it can be a $C_1$-$C_6$ alkylene, optionally substituted with 1-4 substituents selected from —NH—, —C(O)—, —COOH, —N($C_1$-$C_3$ alkyl)-, —NH$_2$ or —NH($C_1$-$C_3$ alkyl). In some embodiments, $R^{L3}$ is ethylenediamine, —NH—CH(COOH)—CH$_2$—NH— or —C(O)—CH(CH$_2$NH$_2$)—.

In some embodiments of the above, AA$_1$ is present and $R^{L1}$, $R^{L2}$ and $R^{L3}$ are absent.

In some embodiments of the above, AA$_1$ is present, $R^{L1}$ is present and $R^{L2}$ and $R^{L3}$ are absent.

In some embodiments of the above, AA$_1$ is present, $R^{L1}$ is present, $R^{L2}$ is present and $R^{L3}$ is absent.

In some embodiments of the above, AA$_1$ is present, $R^{L1}$ is present, $R^{L2}$ is present and $R^{L3}$ is present.

In some embodiments of the above, AA$_1$ is a hydrophilic amino acid and at least one of $R^{L1}$, $R^{L2}$ and $R^{L3}$ s present and is an optionally substituted alkylene, as set forth above.

In some embodiments of the above, AA$_1$ is Glutamate and at least one of $R^{L1}$, $R^{L2}$ and $R^{L3}$ is present and is an optionally substituted alkylene, as set forth above.

In some embodiments of the above, AA$_1$ is Glutamate, $R^{L1}$ is a hydrophilic amino acid and at least one of $R^{L2}$ and $R^{L3}$ is present and is an optionally substituted alkylene, as set forth above.

In some embodiments of the above, AA$_1$ and $R^{L1}$ are hydrophilic amino acids and at least one of $R^{L2}$ and $R^{L3}$ is present and is an optionally substituted alkylene, as set forth above.

In some embodiments of the above, AA$_1$ is a hydrophilic amino acid and $R^{L1}$ and optionally $R^{L3}$ are an optionally substituted alkylene, as set forth above.

In some embodiments of the above, $L^H$ does not include a glycine dipeptide (Gly-Gly), tripeptide or tetrapeptide. In some embodiments, $L^H$ does not include the peptide Asn-(D)Lys.

In some embodiments, $L^H$ will include a modified peptide, having from two to four amino acids. The modified peptide has an amino acid in the 1-position (AA$_1$) that is selected to optimize release of the D$_E$ unit (e.g., by protease cleavage via an amide peptide bond). In one or both of positions $R^{L1}$ and $R^{L2}$ is an amino acid which reverses the orientation of typical N to C linkages of peptides and facilitates attachment of the last amino acid (e.g., $R^{L2}$ or $R^{L3}$) which, prior to attachment of the Ligand unit, includes an α-amino group protected as a maleimide. The amino acid having a reversed N to C linkage is attached to the next group via its side chain. In some embodiments, this amino acid is an alpha amino acid. In other embodiments, it can be a beta or gamma amino acid. In some of these embodiments, the side chain is selected from —CH$_2$NH$_2$—, —CH$_2$CH$_2$NH$_2$—, —CH$_2$CH$_2$CH$_2$NH$_2$—, and —CH$_2$CH$_2$CH$_2$CH$_2$NH$_2$—.

In some embodiments of $L^H$, the amino acid having a reversed N to C linkage ($R^{L1}$) attached to $R^{L2}$ or $R^{L3}$, where $R^{L2}$ or $R^{L3}$ is a hydrophilic amino acid or an optionally substituted alkylene, according to any of the embodiments described above.

In some embodiments of $L^H$, the amino acid having a reversed N to C linkage $R^{L1}$ attached to $R^{L''}$, where $R^{L2}$ is an optionally substituted alkylene, according to any of the embodiments described above.

In some further embodiments, $L^H$ is a hydrophilic, cleavable linker, each branch having the formula:

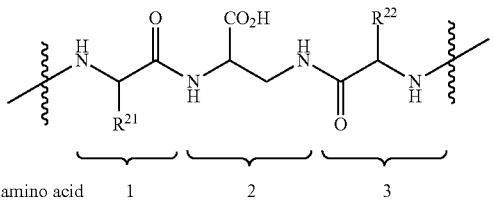

amino acid   1       2       3 wherein $R^{21}$ is selected from —CH$_2$NH$_2$, —CH$_2$CH$_2$NH$_2$—, —CH$_2$OH, —CH$_2$CH$_2$OH, —CH$_2$CO$_2$H, —CH$_2$CH$_2$CO$_2$H, —CH$_2$CH$_2$CH$_2$CO$_2$H, and —CH$_2$CH$_2$CH$_2$CO$_2$H; and $R^{22}$ is selected from —CH$_2$NH$_2$, —CH$_2$CH$_2$NH$_2$, —CH$_2$OH, and —CH$_2$CH$_2$OH. The left and right wavy lines indicate attachment site for the D$_E$ unit and $L^A$, respectively.

In further embodiments $L^H$, or a branch thereof, has the formula:

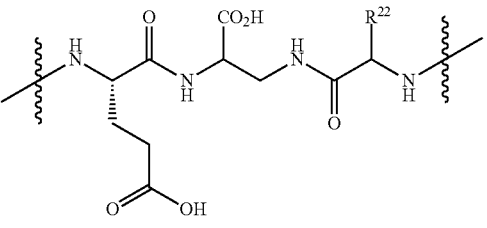

wherein $R^{22}$ is selected from —CH$_2$NH$_2$, —CH$_2$CH$_2$NH$_2$, —CH$_2$OH, and —CH$_2$CH$_2$OH. In some embodiments, $R^{22}$ is selected from —CH$_2$NH$_2$ and —CH$_2$CH$_2$NH$_2$. The left and right wavy lines indicate attachment sites for the D$_E$ unit and $L^A$, respectively.

In certain embodiments, $L^H$, or a branch thereof, has the formula:

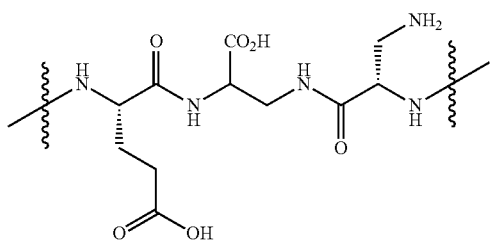

The left and right wavy lines indicate attachments to the $D_E$ unit and $L^A$, respectively.

In certain embodiments, $L^H$, or a branch thereof, has the formula:

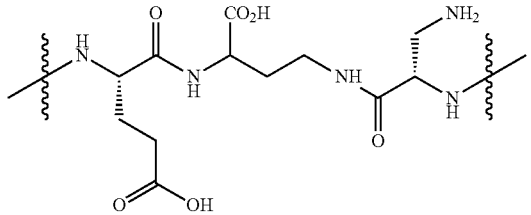

The left and right wavy lines indicate attachment sites for the $D_E$ unit and $L^A$, respectively.

In certain embodiments, $L^H$, or a branch thereof, has the formula:

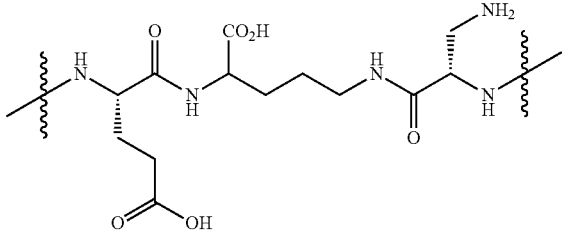

The left and right wavy lines indicate attachment sites for the $D_E$ unit and $L^A$, respectively.

In certain embodiments, $L^H$, or a branch thereof, has the formula:

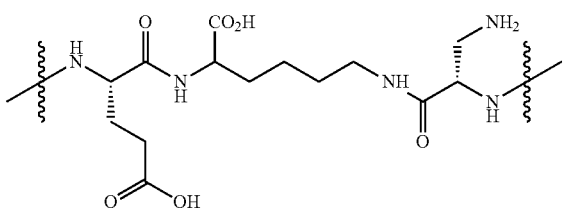

The left and right wavy lines indicate attachment sites for the $D_E$ unit and $L^A$ respectively.

In certain embodiments, L or a branch thereof, has the formula:

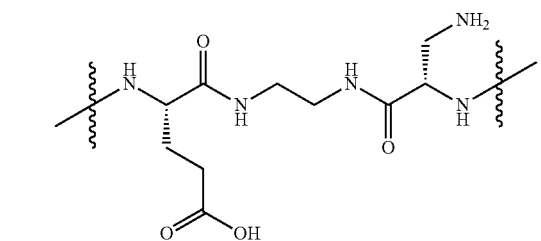

The left and right wavy lines indicate attachment sites for the $D_E$ unit and $L^A$, respectively.

In certain embodiments, $L^H$, or a branch thereof, has the formula:

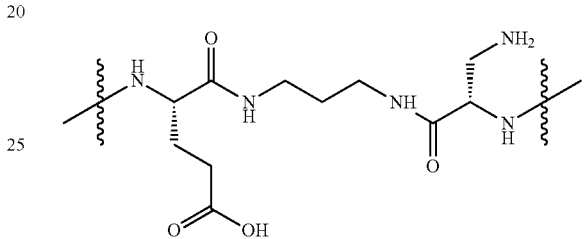

The left and right wavy lines indicate attachment sites for the $D_E$ unit and $L^A$, respectively.

In certain embodiments, $L^H$, or a branch thereof, has the formula:

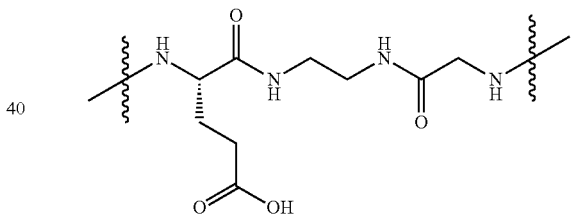

The left and right wavy lines indicate attachment sites for the $D_E$ unit and $L^A$, respectively.

In some further embodiments of the above, $L^H$ is a branched hydrophilic linker having the formula:

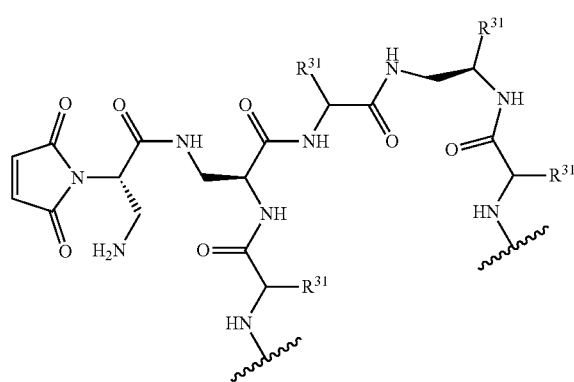

wherein each $R^{31}$ is independently selected from the group consisting of —CH$_2$NH$_2$, —CH$_2$CH$_2$NH$_2$, —CH$_2$OH, —CH$_2$CH$_2$OH, —CH$_2$CO$_2$H, —CH$_2$CH$_2$CO$_2$H, —CH$_2$CH$_2$CH$_2$CO$_2$H, and —CH$_2$CH$_2$CH$_2$CH$_2$CO$_2$H; and each of the bars indicates an attachment site for a D$_E$ unit.

In some further embodiments of the above, L$^H$ is a branched hydrophilic linker having the formula:

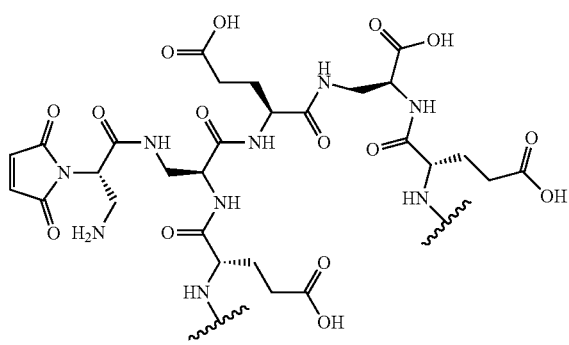 [SMILES: *N[C@@H](CCC(=O)O)C(=O)N[C@@H](CNC(=O)[C@H](CCC(=O)O)NC(=O)[C@H](CNC(=O)[C@H](CN)N1C(=O)C=CC1=O)NC(=O)[C@H](CCC(=O)O)N*)C(=O)O]

wherein each of the bars indicates an attachment site for a D$_E$ unit, and the vertical dashed line indicates an attachment site for the Ligand unit.

The L$^A$ subunit is described in more detail herein.

In each of the embodiments shown above, each of the amine, hydroxyl and carboxylic acid groups are optionally in protected form. Suitable protecting groups are provided in, for example, Greene and Wuts, Protective Groups in Organic Synthesis, J. Wiley & Sons and are generally selected to be removable independent of one another.

Linker-Ligand Conjugates

In yet another aspect, Linker-Ligand conjugates are provided, having a formula selected from:

([L$_H$]$_{p'}$-L$^A$)$_p$-L    (X)

or a pharmaceutically acceptable salt or solvate thereof; wherein:

L is a Ligand that specifically binds to a target;

L$^H$ is an optionally branched hydrophilic linker, each branch of L$^H$ having the formula:

-AA$_1$-R$^{L1}$—R$^{L2}$—R$^{L3}$— ;

L$^A$ is a Ligand Attachment component;

the subscript p is an integer from about 4 to 20; and the subscript p' is an integer from 1 to 4;

wherein the left and right lines of indicate attachment sites to the D$_E$ Unit and L$^A$ respectively.

AA$_1$ can form a cleavable bond with an effector moiety D$_E$, such as a Drug unit. In embodiments where AA$_1$ is attached to an amino acid of D$_E$, AA$_1$ forms a cleavable peptide bond with D$_E$. The cleavable peptide bond is susceptible to cleavage by proteases when the conjugate reaches its target site. In other embodiments, AA$_1$ forms an amide bond with an attachment site of the effector moiety that is susceptible to cleavage (e.g., by proteases) when the conjugate reaches its target site. In some embodiments, AA$_1$ is a hydrophilic amino acid, typically a natural amino acid that is selected from the group consisting of Glycine and L forms of Aspartate, Glutamate, Asparagine, Glutamine, Histidine, Lysine, Arginine, Serine and Alanine. In some embodiments, AA$_1$ is Glutamate.

In some embodiments, L$^A$ is covalently linked to a sulfur atom of the Ligand. L$^A$ can be, for example, a maleimide or succinimide, suitable for attachment to a sulfur atom.

In embodiments where R$^{L1}$ is present and is a hydrophilic amino acid, it can be selected from the group consisting of Glycine; L or D forms of Aspartate, Glutamate, Asparagine, Glutamine, Histidine, Lysine, Arginine, Serine and Alanine; —NH—CH(R$^a$)—C(O)—; and —NH—CH(COOH)—R$^b$; wherein R$^a$ is selected from —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$OH, —CH$_2$CH$_2$CH$_2$CO$_2$H, and —CH$_2$CH$_2$CH$_2$CH$_2$CO$_2$H; and R$^b$ is selected from —CH$_2$NH—, —CH$_2$CH$_2$NH—, —CH$_2$CH$_2$CH$_2$NH—, —CH$_2$CH$_2$CH$_2$CH$_2$NH—, —CH$_2$CH$_2$C(O)—, —CH$_2$CH$_2$CH$_2$C(O)—, and —CH$_2$CH$_2$CH$_2$CH$_2$C(O)—. In some further embodiments, R$^{L1}$ is selected from the group consisting of the D amino acids of Aspartate, Glutamate, Asparagine, Glutamine, Histidine, Lysine, Arginine, Serine and Alanine; Glycine; CH(R$^a$)—C(O)—; and —NH—CH(COOH)—R$^b$—; wherein R$^a$ is selected from —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$OH, —CH$_2$CH$_2$CH$_2$CO$_2$H, and —CH$_2$CH$_2$CH$_2$CH$_2$CO$_2$H; and R$^b$ is selected from —CH$_2$NH—, —CH$_2$CH$_2$NH—, —CH$_2$CH$_2$CH$_2$NH—, —CH$_2$CH$_2$CH$_2$CH$_2$NH—, —CH$_2$CH$_2$C(O)—, —CH$_2$CH$_2$CH$_2$C(O)—, and —CH$_2$CH$_2$CH$_2$CH$_2$C(O)—.

In embodiments where R$^{L1}$ is present and is an optionally substituted alkylene, it can be a C$_1$-C$_6$ alkylene, optionally substituted with 1-4 substituents selected from —NH—, —C(O)—, —COOH, —N(C$_1$-C$_3$ alkyl)-, —NH$_2$ or —NH(C$_1$-C$_3$ alkyl). In some embodiments, R$^{L1}$ is ethylenediamine, —NH—CH(COOH)—CH$_2$—NH— or —C(O)—CH(CH$_2$NH$_2$)—.

In embodiments where R$^{L2}$ is present and is a hydrophilic amino acid, it can be selected from the group consisting of Glycine; L or D forms of Aspartate, Glutamate, Asparagine, Glutamine, Histidine, Lysine, Arginine, Serine and Alanine; —NH—CH(R$^a$)—C(O)—; and —NH—CH(COOH)—R$^b$—; wherein R$^a$ is selected from —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$OH, —CH$_2$CH$_2$CH$_2$CO$_2$H, and —CH$_2$CH$_2$CH$_2$CH$_2$CO$_2$H; and R$^b$ is selected from —CH$_2$NH—, —CH$_2$CH$_2$NH—, —CH$_2$CH$_2$CH$_2$NH—, —CH$_2$CH$_2$CH$_2$CH$_2$NH$_2$, —CH$_2$CH$_2$C(O)—, —CH$_2$CH$_2$CH$_2$C(O)—, and —CH$_2$CH$_2$CH$_2$CH$_2$C(O)—.

In some further embodiments when R$^{L3}$ is present, it is selected from the group consisting of the 1) amino acids of Aspartate, Glutamate, Asparagine, Glutamine, Histidine, Lysine, Arginine, Serine and Alanine; Glycine; —NH—CH(R$^a$)—C(O)—; and —NH—CH(COOH)—R$^b$—; wherein R$^a$ is selected from —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$OH, —CH$_2$CH$_2$CH$_2$CO$_2$H, and —CH$_2$CH$_2$CH$_2$CH$_2$CO$_2$H; and R$^b$ is selected from —CH$_2$NH—, —CH$_2$CH$_2$NH—, —CH$_2$CH$_2$CH$_2$NH—, —CH$_2$CH$_2$—CH$_2$CH$_2$NH—, —CH$_2$CH$_2$C(O)—, —CH$_2$CH$_2$CH$_2$C(O)—, and —CH$_2$CH$_2$CH$_2$CH$_2$C(O)—.

In embodiments where R$^{L2}$ is present and is an optionally substituted alkylene, it can be a C$_1$-C$_6$ alkylene, optionally substituted with 1-4 substituents selected from —NH—, —CO)—, —COOH, —N($C_1$-$C_3$ alkyl)-, —$NH_2$ or —NH ($C_1$-$C_3$ alkyl). In some embodiments, $R^{L3}$ is ethylenediamine, —NH—CH(COOH)—$CH_2$—NH— or —C(O)—CH($CH_2NH_2$)—.

In embodiments where $R^{L3}$ is present, and is a hydrophilic amino acid, it can be selected from the group consisting of Glycine; L or D forms of Aspartate, Glutamate, Asparagine, Glutamine, Histidine, Lysine, Arginine, Serine and Alanine; —NH—CH($R^a$)—C(O)—; and —NH—CH(COOH)—$R^b$—; wherein $R^a$ is selected
from —$CH_2NH_2$, —$CH_2CH_2NH_2$, —$CH_2CH_2CH_2NH_2$, —$CH_2CH_2CH_2CH_2NH_2$, —$CH_2CH_2OH$, —$CH_2CH_2CH_2CO_2H$, and —$CH_2CH_2CH_2CH_2CO_2H$; and $R^b$ is selected
from —$CH_2NH$—, —$CH_2CH_2NH$—, —$CH_2CH_2CH_2NH$—, —$CH_2CH_2CH_2CH_2NH$—, —$CH_2CH_2C(O)$—, —$CH_2CH_2CH_2C(O)$—, and —$CH_2CH CH_2CH_2C(O)$, In some further embodiments when $R^{L3}$ is present, is selected from the group consisting of the D amino acids of Aspartate, Glutamate, Asparagine, Glutamine, Histidine, Lysine, Arginine, Serine and Alanine; Glycine; —NH—CH($R^a$)—C(O)—; and —NH—CH(COOH)—$R^b$—; wherein $R^a$ is selected
from —$CH_2NH_2$, —$CH_2CH_2NH_2$, —$CH_2CH_2CH_2NH_2$, —$CH_2CH_2CH_2CH_2NH_2$, —$CH_2CH_2OH$, —$CH_2CH_2CH_2CO_2H$, and —$CH_2CH_2CH_2CH_2CO_2H$; and $R^b$ is selected
from —$CH_2NH$—, —$CH_2CH_2NH$—, —$CH_2CH_2CH_2NH$—, —$CH_2CH_2CH_2CH_2NH$—, —$CH_2CH_2C(O)$—, —$CH_2CH_2CH_2C(O)$—, and —$CH_2CH_2CH_2CH_2C(O)$—.

In embodiments where $R^{L3}$ is present and is an optionally substituted alkylene, it can be a $C_1$-$C_6$ alkylene, optionally substituted with 1-4 substituents selected from —NH—, —C(O)—, —COOH, —N($C_1$-$C_{11}$ alkyl)-, —$NH_2$ or NH($C_1$-$C_3$ alkyl). In some embodiments, R' ethylenediamine, —NH—CH(COOH)—$CH_2$—NH— or —C(O)—CH($CH_2NH_2$)—.

In some embodiments of the above, $AA_1$ is present and $R^{L1}$, $R^{L2}$ and $R^{L3}$ are absent.

In some embodiments of the above, $AA_1$ is present, $R^{L1}$ is present and $R^{L2}$ and $R^{L3}$ are absent.

In some embodiments of the above, $AA_1$ is present, $R^{L1}$ is present, $R^{L2}$ is present and $R^{L3}$ is absent.

In some embodiments of the above, $AA_1$ present, $R^{L1}$ is present, $R^{L2}$ is present and $R^{L3}$ is present.

In some embodiments of the above, $AA_1$ is a hydrophilic amino acid and at least e of $R^{L1}$, $R^{L2}$ and $R^{L3}$ is present and is an optionally substituted alkylene, as set forth above.

In some embodiments of the above, $AA_1$ is Glutamate and at least one of $R^{L1}$, $R^{L2}$ and $R^{L3}$ is present and is an optionally substituted alkylene, as set forth above.

In some embodiments of the above, $AA_1$ is Glutamate, $R^1$ is a hydrophilic amino acid and at least one of $R^{L2}$ and $R^{L3}$ is present and is an optionally substituted alkylene, as set forth above.

In some embodiments of the above, and $R^{L1}$ are hydrophilic amino acids and at least one of $R^{L2}$ and $R^{L3}$ is present and is an optionally substituted alkylene, as set forth above.

In some embodiments of the above, $AA_1$ is a hydrophilic amino acid and $R^{L1}$ and optionally $R^{L2}$ are an optionally substituted alkylene, as set forth above.

In some embodiments of the above, $L^H$ does not include a glycine dipeptide (Gly-Gly), tripeptide or tetrapeptide. In some embodiments, $L^H$ does not include the peptide Asn-(D)Lys.

In some embodiments, $L^H$ will include a modified peptide, having from two to four amino acids. The modified peptide has an amino acid in the 1-position ($AA_1$) that is selected to optimize release of the $D_E$ unit (e.g., by protease cleavage via an amide peptide bond). In one or both of positions $R^{L1}$ and $R^{L2}$ is an amino acid which reverses the orientation of typical N to C linkages of peptides and facilitates attachment of the last amino acid (e.g., $R^{L2}$ or $R^{L3}$) which, prior to attachment of the Ligand unit, includes an α-amino group protected as a maleimide. The amino acid having a reversed N to C linkage is attached to the next group via its side chain. In some embodiments, this amino acid is an alpha amino acid. In other embodiments, it can be a beta or gamma amino acid. In some of these embodiments, the side chain is selected
from —$CH_2NH_2$—, —$CH_2CH_2NH_2$—, —$CH_2CH_2CH_2NH_2$—, and —$CH_2CH_2CH_2CH_2NH_2$—.

In some embodiments of $L^H$, the amino acid having a reversed N to C linkage ($R^{L1}$) attached to $R^{L2}$ or $R^{L3}$, where $R^{L2}$ or $R^{L3}$ is a hydrophilic amino acid or an optionally substituted alkylene, according to any of the embodiments described above.

In some embodiments of $L^H$, the amino acid having a reversed N to C linkage $R^{L1}$ attached to $R^{L2}$, where $R^{L2}$ is an optionally substituted alkylene, according to any of the embodiments described above.

In some further embodiments, $L^H$ is a hydrophilic, cleavable linker, each branch having the formula:

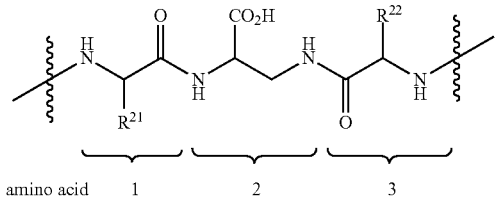

amino acid   1        2        3 wherein $R^{21}$ is selected from —$CH_2NH_2$, —$CH_2CH_2NH_2$, —$CH_2OH$, —$CH_2CH_2OH$, —$CH_2CO_2H$, —$CH_2CH_2CO_2H$, —$CH_2CH_2CH_2CO_2H$, and —$CH_2CH_2CH_2CH_2CO_2H$; and $R^{22}$ is selected from —$CH_2NH_2$, —$CH_2CH_2NH_2$, —$CH_2OH$, and —$CH_2CH_2OH$. The left and right wavy lines indicate attachments to the $D_E$ unit and $L^A$, respectively.

In further embodiments $L^A$, or a branch thereof, has the formula:

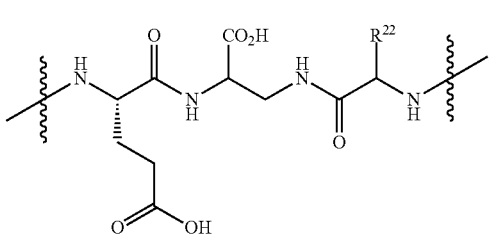

wherein $R^{22}$ is selected from —$CH_2NH_2$, —$CH_2CH_2NH_2$, —$CH_2OH$, and —$CH_2CH_2OH$. In some embodiments, $R^{22}$ is selected from —$CH_2NH_2$, and —$CH_2CH_2NH_2$, The left and right wavy lines indicate attachments to the $D_E$ unit and $L^A$, respectively.

In certain embodiments, $L^H$, or a branch thereof, has the formula:

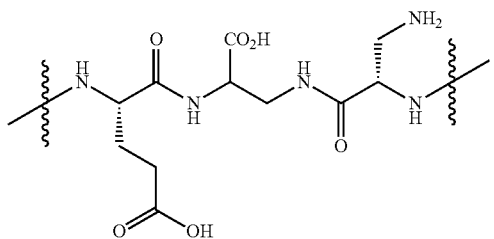

The left and right wavy lines indicate attachments to the $D_E$ unit and $L^A$, respectively.

In certain embodiments, $L^H$, or a branch thereof, has the formula:

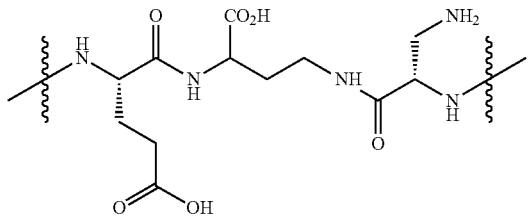

The left and right wavy lines indicate attachments to the $D_E$ unit $L^A$ and respectively.

In certain embodiments, $L^H$, or a branch thereof, has the formula:

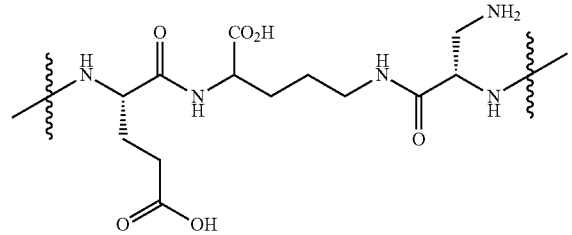

The left and right wavy lines indicate attachments to the $D_E$ unit and $L^A$, respectively.

In certain embodiments, $L^H$, or a branch thereof, has the formula:

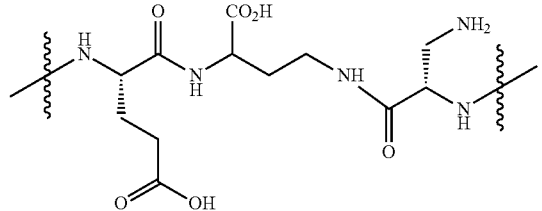

The left and right wavy lines indicate attachments to the $D_E$ unit and $L^A$, respectively.

In certain embodiments, $L^H$, or a branch thereof, has the formula:

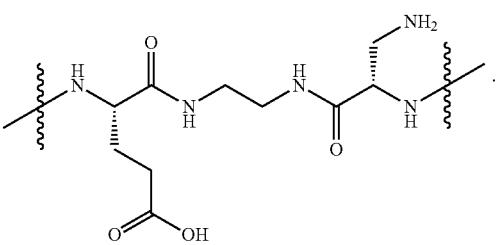 [SMILES: *N[C@@H](CN)C(=O)NCCNC(=O)[C@H](CCC(=O)O)N*]

The left and right wavy lines indicate attachments to the $D_E$ unit and $L^A$, respectively.

In certain embodiments, $L^H$, or a branch thereof, has the formula:

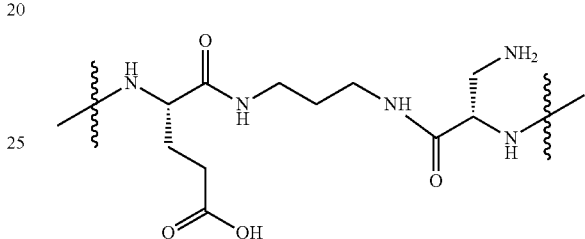

The left and right wavy lines indicate attachments to the $D_E$ unit and $L^A$, respectively.

In certain embodiments, $L^H$, or a branch thereof, has the formula:

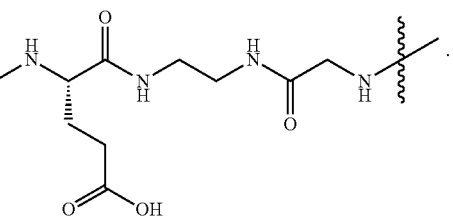

The left and right wavy lines indicate attachments to the $D_E$ unit and $L^A$, respectively.

In some further embodiments of the above, $L^H$ is a branched hydrophilic linker having the formula:

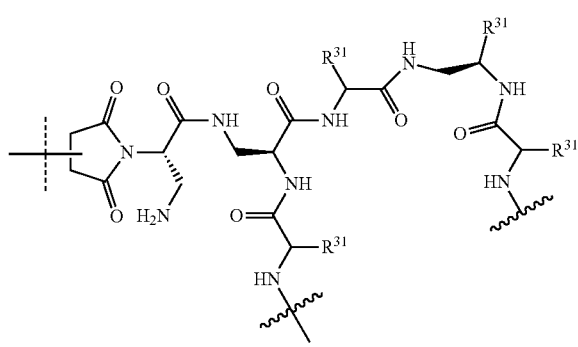

wherein each $R^{31}$ is independently selected from the group consisting of —$CH_2NH_2$, —$CH_2CH_2NH_2$, —CH$_2$OH, —CH$_2$CH$_2$OH, —CH$_2$CO$_2$H, —CH$_2$CH$_2$CO$_2$H, —CH$_2$CH$_2$CH$_2$CO$_2$H, and —CH$_2$CH$_2$CH$_2$CH$_2$CO$_2$H; and each of the bars indicates attachment site for a D$_E$ unit, and the vertical dashed line indicates an attachment site for the Ligand unit.

In some further embodiments of the above, L$^H$ is a branched hydrophilic linker having the formula:

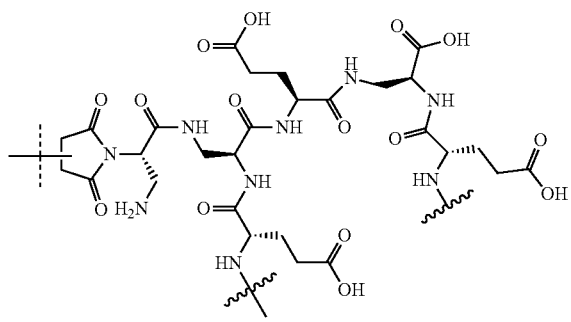

wherein each of the bars indicates attachment to a D$_E$ unit, and the vertical dashed line indicates an attachment site for the Ligand unit.

The L$^4$ subunit is described in more detail above.

In each of the embodiments shown above, each of the amine, hydroxyl and carboxylic acid groups are optionally in protected form. Suitable protecting groups are provided in Greene and Wuts, Protective Groups in Organic Synthesis, J. Wiley & Sons and are generally selected to be removable independent of one another.

(VIIa)

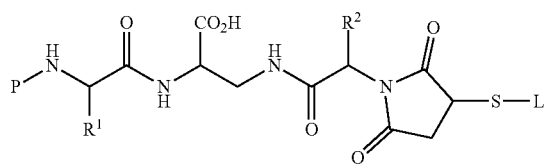

(VIIb)

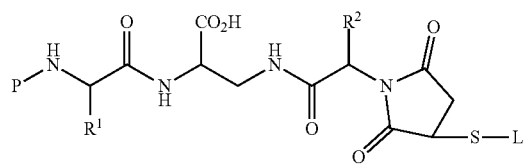

(VIIc)

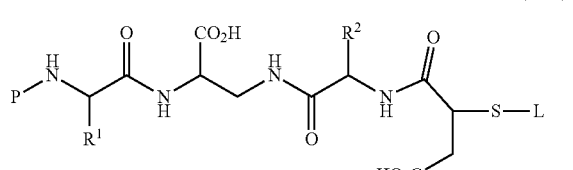

(VIId)

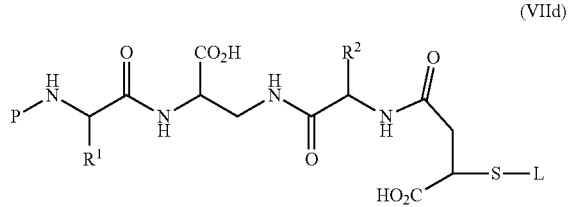

wherein P is H or a protecting group, and each of the remaining functional groups present in R$^1$, R$^2$, the carboxylic acids shown are optionally protected and S is a sulfur atom of the Ligand.

Treatment of Diseases

Further provided are methods of treatment of disease using the Ligand-Linker-Drug conjugates of any of the formulas described herein. The disease can be, for example, a cancer or tiara autoimmune disease. The Ligand-Linker-Drug conjugates are administered in a therapeutically effective amount and on a therapeutically effective schedule, in some aspects, the conjugate dose is the same or less than that of a comparable two loaded conjugate. In some aspects, the conjugate dose is the same or less than that of a comparable four loaded conjugate. In some aspects, the conjugate dose is the same or less than that of a comparable two loaded conjugate, while the dosing schedule is the same or less frequent. In some aspects, the conjugate dose is the same or less than that of a comparable four loaded conjugate, while the dosing schedule is the same or less frequent. In some further aspects, the conjugate dose is greater and the dosing schedule is the same or less frequent than that of a comparable two loaded conjugate. In some further aspects, the conjugate dose is less and the dosing schedule is the same or less frequent than that of a comparable four loaded conjugate. The comparator conjugate can be, for example, the same Ligand-Drug-Linker conjugate having a drug loading of 2 or 4, Treatment of Cancer The Ligand-Linker-Drug Conjugates are useful for inhibiting the multiplication of a tumor cell or cancer cell, causing apoptosis in a tumor or cancer cell, or for treating cancer in a patient. The Ligand-Linker-Drug Conjugates can be used accordingly in a variety of settings for the treatment of cancers. The Ligand-Drug Conjugates can be used to deliver a drug to a tumor cell or other cancer cell. Without being bound by theory, in one embodiment, the Ligand unit of a Ligand-Linker-Drug Conjugate specifically binds to a target (e.g., an antigen on a cancer-cell), and the Ligand-Drug Conjugate can be taken up (internalized) inside a tumor cell or cancer cell through receptor-mediated endocytosis or other internalization mechanism. The antigen can be attached to a tumor cell or cancer cell or can be an extracellular matrix protein associated with the tumor cell or cancer cell. Once inside the cell, the drug (cytotoxic agent) is released within the cell. In an alternative embodiment, the Drug or Drug unit is cleaved from the Ligand-Linker-Drug Conjugate outside the tumor cell or cancer cell, and the Drug or Drug unit subsequently penetrates the cell.

The Ligand-Linker-Drug Conjugates can provide conjugation-specific tumor or cancer drug targeting, thus reducing general toxicity of the drug (if administered alone).

In one embodiment, the Ligand unit specifically binds to the tumor cell or c r cell.

In another embodiment, the Ligand unit specifically binds to a tumor cell or cancer cell antigen which is on the surface of the tumor cell or cancer cell.

In another embodiment, the Ligand unit specifically binds to a tumor cell or cancer cell antigen which is an extracellular matrix protein associated with the tumor cell or cancer cell.

The specificity of the Ligand unit for a particular tumor cell or cancer cell can be important for determining those tumors or cancers that are most effectively treated.

Particular types of cancers that can be treated with Ligand-Linker-Drug conjugates include, but are not limited to, solid tumors (such an renal cell cancer, liver cancer and skin cancer) and blood-borne cancers (such as acute myeloblastic leukemia (AML), chronic myelocytic leukemia (CML), chronic lymphocytic leukemia (CLL) and multiple myeloma), Acute and chronic leukemias and lymphomas (such as Hodgkin Lymphoma and non-Hodgkin Lymphoma) can be treated.

Cancers, including, but not limited to, a tumor, metastasis, or other disease or disorder characterized by uncontrolled cell growth, can be treated or inhibited by administration of the Ligand-Linker Drug Conjugates.

In other embodiments, methods for treating cancer are provided, including administering to a patient in need thereof an effective amount of a Ligand-Drug Conjugate and a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. The Ligand-Drug Conjugates can be administered to a patient that has also undergone surgery as treatment for the cancer.

In some embodiments, the patient also receives an additional treatment, such as radiation therapy. In a specific embodiment, the Ligand-Drug Conjugate is administered concurrently with the chemotherapeutic agent or with radiation therapy. In another specific embodiment, the chemotherapeutic agent or radiation therapy is administered prior or subsequent to administration of a Ligand Drug conjugate.

A chemotherapeutic agent can be administered over a series of sessions or as a single dose. Any one or a combination of the chemotherapeutic agents, such a standard of care chemotherapeutic agent(s), can be administered.

Additionally, methods of treatment of cancer with a Ligand-Drug Conjugate are provided as an alternative to chemotherapy or radiation therapy where the chemotherapy or the radiation therapy has proven or can prove too toxic, e.g., results in unacceptable or unbearable side effects, for the subject being treated. The patient being treated can, optionally, be treated with another cancer treatment such as surgery, radiation therapy or chemotherapy, depending on which treatment is found to be acceptable or bearable.

Treatment of Autoimmune Diseases

The Ligand-Drug Conjugates are useful for killing or inhibiting the replication of a cell(s) that produces or is involved in an autoimmune disease or for treating an autoimmune disease. The Ligand-Drug Conjugates can be used accordingly in a variety of settings for the treatment of an autoimmune disease in a patient. The Ligand-Drug Conjugates can be used to deliver a drug to a target cell. Without being bound by theory, in one embodiment, the Ligand-Drug Conjugate specifically binds to an antigen on the surface of a target cell, and the Ligand-Linker-Drug conjugate is then taken up inside a target-cell through receptor-mediated endocytosis or other internalization mechanism. Once inside the cell, the Drug unit is released. The released Drug unit is then free to migrate in the cytosol and induce cytotoxic or cytostatic activities. In an alternative embodiment, the Drug is cleaved from the Ligand-Drug Conjugate outside the target cell, and the Drug or Drug unit subsequently penetrates the cell.

In one embodiment, the Ligand unit binds to an autoimmune antigen. In one aspect, the antigen is on the surface of a cell involved in an autoimmune condition.

In another embodiment, the Ligand unit binds to an autoimmune antigen which is on the surface of a cell.

In one embodiment, the Ligand unit binds to activated lymphocytes that are associated with the autoimmune disease state.

In a further embodiment, the Ligand-Drug Conjugate kills or inhibit the multiplication of cells that produce an autoimmune antibody associated with a particular autoimmune disease.

Particular types of autoimmune diseases that can be treated with the ligand drug conjugates include, but are not limited to, Th2 lymphocyte related disorders (e.g., atopic dermatitis, atopic asthma, rhinoconjunctivitis, allergic rhinitis, Omenn's syndrome, systemic sclerosis, and graft versus host disease); Th1 lymphocyte-related disorders (e.g., rheumatoid arthritis, multiple sclerosis, psoriasis, Sjorgren's syndrome, Hashimoto's thyroiditis, Grave's disease, primary biliary cirrhosis, Wegener's granulomatosis, and tuberculosis); activated B lymphocyte-related disorders (e.g., systemic lupus erythematosus, Goodpasture's syndrome, rheumatoid arthritis, and type I diabetes).

Methods for treating an autoimmune disease are also disclosed including administering to a patient in need thereof an effective amount of a Ligand-Linker-Drug Conjugate and another therapeutic agent known for the treatment of an autoimmune disease.

Treatment of Infectious Diseases

The Ligand-Linker-Drug Conjugates are useful for killing or inhibiting the multiplication of a cell that produces an infectious disease or for treating an infectious disease. The Ligand-Linker-Drug Conjugates can be used accordingly in a variety of settings for the treatment of an infectious disease in a patient. The Ligand-Linker-Drug Conjugates can be used to deliver a drug (e.g., an antibiotic) to a target cell. In one embodiment, the Ligand unit binds to the infectious disease cell.

In one embodiment, the conjugates kill or inhibit the multiplication of cells that produce a particular infectious disease.

Methods for treating an infectious disease are disclosed including administering to a patient in need thereof a Ligand-Linker-Drug Conjugate and another therapeutic agent that is an anti-infectious disease agent.

Compositions and Methods of Administration

The present invention further provides pharmaceutical compositions comprising the Ligand-Linker-Drug Conjugates described herein and a pharmaceutically acceptable carrier. The Ligand-Linker-Drug Conjugates can be in any form that allows for the compound to be administered to a patient for treatment of a disorder associated with expression of the antigen to which the Ligand unit specifically binds. For example, the conjugates can be in the form of a liquid or solid. The preferred route of administration is parenteral. Parenteral administration includes subcutaneous, intravenous, intramuscular, intrasternal injection or infusion techniques. In one aspect, the compositions are administered parenterally. In another aspect, the compounds are administered intravenously.

Pharmaceutical compositions of the Ligand-Linker-Drug Conjugates can be formulated so as to allow a compound to be bioavailable upon administration of the conjugate to a patient. Compositions can take the form of one or more dosage units, where for example, a vial can be a single dosage unit.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the compound, the manner of administration, and the composition employed.

The pharmaceutical compositions can be, for example, in the form of a liquid. The liquid can be useful for delivery by injection. In a composition for administration by injection or intravenous administration, one or more of a surfactant, preservative, wetting agent, dispersing agent, suspending agent, buffer, stabilizer and/or isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as amino acids, acetates, citrates or phosphates; detergents, such as nonionic surfactants, polyols; and agents for the adjustment of tonicity such as sodium chloride or dextrose. A parenteral composition can be enclosed in ampoule, a disposable syringe or a single or multiple-dose vial made of glass, plastic or other material. Physiological saline is an exemplary adjuvant. An injectable composition is preferably sterile.

The amount of the conjugate that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the pharmaceutical compositions will also depend on the route of administration, and the seriousness of the disease or disorder, and should be decided according to the judgment of the practitioner and each patient's circumstances.

The compositions comprise an amount of a compound such that a suitable dosage will be obtained. Typically, this amount is at least about 0.01% of a compound by weight of the composition.

For intravenous administration, the composition can comprise from about 0.01 to about 10 mg of a Ligand-Linker-Drug Conjugate per kg of the animal's body weight. In one aspect, the composition can include from about 0.01 to about 10 mg of a Ligand-Drug Conjugate per kg of the animal's body weight. In another aspect, the amount administered will be in the range from about 0.1 to about 7.5 mg/kg of body weight of a compound.

Generally, the dosage of a compound administered to a patient is typically about 0.01 mg/kg to about 10 mg/kg of the subject's body weight. In some embodiments, the dosage administered to a patient is between about 0.01 mg/kg to about 7.5 mg/kg of the subject's body weight. In some embodiments, the dosage administered to a patient is between about 0.1 mg/kg and about 5 mg/kg of the subject's body weight. In some embodiments, the dosage administered to a patient is between about 0.1 mg/kg and about 4 mg/kg of the subject's body weight. In some embodiments, the dosage administered is between about 0.1 mg/kg to about 3 mg/kg or about 0.1 mg/kg to about 2 mg/kg of the subject's body weight. In some embodiments, the dosage administered is between about 0.5 mg/kg to about 5 mg/kg of the subject's body weight. In some embodiments, the dosage administered is between about 1 mg/kg to about 5 mg/kg of the subject's body weight. In some embodiments, the dosage administered is between about 0.1 to 4 mg/kg, even more preferably 0.1 to 3.2 mg/kg, or even more preferably 0.1 to 2.7 mg/kg of the subject's body weight over a treatment cycle.

The Ligand-Linker Drug Conjugates can be administered by any convenient route, for example by infusion or bolus injection, by absorption through epithelial or mucocutaneous linings (e.g., oral mucosa, rectal and intestinal mucosa). Administration can be systemic or local. Various delivery systems are known, e.g., encapsulation in liposomes, microparticles, microcapsules, capsules, and can be used to administer a compound. In certain embodiments, more than one compounds or composition is administered to a patient.

The term "carrier" refers to a diluent, adjuvant or excipient, with which a compound is administered. Such pharmaceutical carriers can be liquids, such as water. The carriers can be saline, gum acacia, gelatin, starch paste, talc, keratin, colloidal silica, urea. In addition, auxiliary, stabilizing, thickening, lubricating and coloring agents can be used. In one embodiment, when administered to a patient, the compound or compositions and pharmaceutically acceptable carriers are sterile. Water is an exemplary carrier when the compounds are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol. The present compositions, if desired, can also contain minor amounts of wetting or emulsifying agents, or pH buffering agents.

In an embodiment, the conjugates are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a conjugate is to be administered by infusion, it can be dispensed, for example, with an infusion bottle containing sterile pharmaceutical grade water or saline. Where the conjugate is administered by injection, an ampoule of sterile water for injection or saline can be provided so that the ingredients can be mixed prior to administration.

The pharmaceutical compositions are generally formulated as sterile, substantially isotonic and in full compliance with all Good Manufacturing Practice (GMP) regulations of the U.S. Food and Drug Administration.

Pharmaceutical compositions of the present invention comprise the Ligand Drug Conjugates of the present invention and a pharmaceutically acceptable carrier. In some preferred embodiments, all, or substantially all, or more than 50% of the Ligand Drug Conjugates present in the pharmaceutical composition comprises a hydrolyzed thio-substituted succinimide. In some preferred embodiments, more than 55%, 60%, 65%, 70%, 75%, 80%, 85%, 90%, 91%, 92%, 93%, 94%, 95%, 96%, 97%, 98%, or 99% of the Ligand Drug Conjugates present in the pharmaceutical composition comprises a hydrolyzed thio-substituted succinimide.

Methods for Preparing Ligand-Drug Conjugates

In another aspect, the present invention provides methods of preparing Ligand-Drug Conjugates, Linkers, Drug-Linker and Linker-Ligand Conjugates In some embodiments, methods of the present invention comprise the steps of providing a Drug-Linker or Linker unit as described herein, conjugating said Drug-Linker or Linker unit to a sulfhydryl group of a Ligand unit to form a conjugate. In some further embodiments, the thio-substituted maleimide or succinimide group(s) of conjugate may undergo a hydrolysis reaction.

The rate of the thio-substituted succinimide hydrolysis can be manipulated by adjusting the reaction conditions following conjugation of the Drug-Linker to the Ligand, e.g., by adjusting the pH or temperature. In some embodiments of the present invention, all, substantially all, or at least 50%, 60%, 70%, 80%, 85%, 90% or even 95% of the thio-substituted succinimide is hydrolyzed without manipulation of the reaction conditions, i.e., the hydrolysis reaction occurs under the same reaction conditions as the conjugation reaction. In some embodiments, all, substantially all, or at least 50%, 60%, 70%, 80%, 85%, 90% or even 95% of the thio-substituted succinimide is hydrolyzed from 20 minutes, to 4 hours following conjugation, preferably from 20 minutes to 2 hours following conjugation. In exemplary embodiments, the conjugation conditions are pH of about 7.4 and a temperature of about 22° C.

In some embodiments, methods for preparing a Ligand-Drug Conjugate comprises the steps of providing a Drug-Linker or Linker unit; conjugating said Drug-Linker or Linker unit to a sulfhydryl group of a Ligand to form a Ligand-Drug Conjugate conjugate comprising a non-hydrolyzed thio-substituted succinimide; allowing the non-hydrolyzed thio-substituted succinimide to undergo a hydrolysis reaction, wherein all, substantially all, or at least 50%, 60%, 70%, 80% or even 85% of the succinimide is hydrolyzed from 10 minutes to 4 hours following conjugation. In some embodiments, all, substantially all, or at least 50%, 60%, 70%, 80%, 85%, 90% or even 95% of the succinimide is hydrolyzed by 10 minutes, by 20 minutes, 40 minutes 60 minutes, 90 minutes or 120 minutes following conjugation. In some embodiments, the hydrolysis reaction occurs under the same reaction conditions as the conjugation reaction. In exemplary embodiments, the conjugation conditions are pH of about 7.4 and a temperature of About 22° C.

Assembly of the Ligand-Drug Conjugates

The Ligand-Drug conjugates of the present invention can be assembled following the general scheme outlined in FIG. 1.

EXAMPLES

General

Unless otherwise noted, materials were obtained from commercial suppliers in the highest purity grade available and used without further purifications. Anhydrous DMF and $CH_2Cl_2$ were purchased from Aldrich. Fmoc-Dolaproine-OH was custom synthesized by Albany Molecular Research, Inc. (Albany, N.Y.). Dolavaline-Val-Dil-OH was prepared as described elsewhere. Fmoc-Dpr(ivDde)-OH and 2-Chlorotrityl chloride resin (200-300 mesh, 1% DVB, substitution 1 mmol/grain) were purchased from Novabiochem. Solid phase synthesis was performed in plastic syringes (National Scientific Company) fitted with a filter cut out of fritware PE medium grade porous sheet (Scienceware). A Burrell wrist Action® shaker (Burrell Scientific, Pittsburgh, Pa.) was used for agitation. All solid-phase yields reported are based upon the initial substitution level of the resin and constitute a mass balance of isolated pure material, unless otherwise stated.

Preparative HPLC purifications were performed on Varian instrument equipped with C12 Phenomenex Synergy MAX-RP 4μ reversed phase column, 250×10 mm, eluting with 0.05% TFA in a water-acetonitrile gradient.

Mass spectra data were obtained on a XEVO TOF MS interfaced to a Waters 2795 HPLC equipped with a C12 Phenomenex Synergi 2.0×150 mm, 4 μm, 80 Å reverse-phase column. The eluent consisted of a linear gradient of acetonitrile from 5% to 95% in 0.1% aqueous formic acid over 10 min, followed by isocratic 95% acetonitrile for 5 min at flow rate 0.4 mL/min.

The humanized h1F6 antibody specifically binds to the human CD70 antigen (Cancer Res 2006, 66(4), p. 2328; U.S. Pat. No. 8,067,546). The humanized bBU12 antibody specifically binds to the human CD19 antigen (Blood, 2009, 113(18), p. 4362; U.S. Pat. No. 7,968,687). Human renal cell carcinoma cell lines 786-0 and Caki-1 expressing human CD70, and human transformed follicular lymphoma DOHH2 cells expressing human CD19 were purchased from the American Type Culture Collection (ATCC; Manassas, Va.). All cell lines were grown according to the suppliers' recommendations and routinely checked for mycoplasma contamination.

Abbreviations: DPR means diaminopropionic acid; ivDde is 1-(4,4-dimeth-2,6-dioxocyclohex-1-ylidene)-3-methylbutyl-, Example 1—General Procedures to Syntheses Synthesis of Maleimido-Dpr(Boc)-OH $N_β$-Boc-L-2,3-diaminopropionic acid (1 mmol) and maleic anhydride (98 mg, 1 mmol) were dissolved in acetic acid (1 mL) in a 50 ml round bottom flask, and the solution was stirred at room temperature for 3 hours. The solution was then concentrated to an oil under reduced pressure. The maleic acid intermediate was precipitated by adding ~10 mL $CH_2Cl_2$/hexane, 1/1, v/v, and the precipitate was collected by vacuum filtration. This material was then suspended in toluene (9 mL), followed by the addition of DMA (0.3 mL), and triethylamine (0.42 mL, 3 mmol). The mixture was stirred at 40-60° C. under $N_2$ until all material was in solution. The flask was then equipped with a condenser and the solution heated to 120° C. and refluxed for 4 hours over molecular sieves. The reaction mixture was filtered through a sintered glass funnel and concentrated to near dryness under reduced pressure. The residue was dissolved in ethyl acetate (10 mL), transferred to a separatory funnel and washed with 10% citric acid in water (2×10 mL) and brine (2×10 mL). The organic layer was dried over magnesium sulfate, concentrated under reduced pressure, and dried under high vacuum overnight yielding product as a white powder with 72% yield. $^1$H NMR (DMSO): δ 1.29 (s, 9H), 3.41 (m, 1H), 152 (ran 1H) 4.57 (dd, 1H). 6.97 (t, 1H), 7.07 (s, 2H). LCMS (ESI) calcd. for $(M+Na)^+$307.09; found, m/z 307.17.

General Procedures for Auristatin-$AA_1$-MDpr Synthesis.

FIG. 1 illustrates an exemplary synthesis of auristatin-$(AA_2)$-$AA_1$-MDpr drug-linkers.

Resin loading. In a 20 mL solid phase reaction vessel (plastic syringe with PET frit) was added 1 g of 2-chlorotrityl chloride resin (1 mmol based on the manufacturer's label), followed by a solution of Fmoc-Dpr(ivDde)-OH or Fmoc-Lys(ivDde)-OH (1.5 mmol, 1.5 equiv), and DIEA (1 mmol, 1 equiv) in 10 mL of dry $CH_2Cl_2$/DMF, 1/1, v/v. The vessel was shaken for 5 min, and then more DIEA (1.5 mmol, 1.5 equiv) was added. The mixture was shaken for additional 2 hours at RT, Methanol (2.5 mL) was added to quench unreacted sites. After 30 min, resin was washed with DMF (5×10 mL), CH$_2$Cl$_2$ (5×10 mL), ethyl ether (5×10 mL), and dried in vacuo.

Loading was determined by treating the small amount of resin (2-4 mg) with 20% piperidine/DMF (2 mL) for 2 hours in volumetric flask (10 or 20 mL). Volume was adjusted with DMF; absorption at 301 nm was measured. Loading was calculated by the following equation:

Loading(mmol/g)=(flask volume×$A_{301}$)/800×mg)× 1000

Average loading was ~0.6 mmol/g

Fmoc removal step. Resin containing Fmoc-protected peptide was treated with 20% piperidine ire DMF (10 mL per gram of resin) for 2 h at room temperature. Then the resin was washed with DMF (5×1 mL per gram of resin), CH$_2$Cl$_2$ (5×1 mL per gram of resin), ethyl ether (5×1 mL per gram of resin), and dried in vacuo.

Coupling step. To the resin (1 equiv) containing deprotected N-terminus amino acid (AA), a solution of Fmoc-AA-OH (2 equiv), HATU (2 equiv), and DIEA (4 equiv) iii DMF (1 mL per gram of resin) was added. The reaction vessel was agitated for 3-4 h. Then the resin was washed with DMF (5×1 mL per gram of resin), CH$_2$Cl$_2$ (5×1 mL per gram of resin), ethyl ether (5×1 mL per gram of resin), and dried in vacuo. Reaction completion was confirmed by negative Kaiser test where appropriate.

Coupling of N-terminal Dolavaline-Val-Dil-OH was performed in a similar way.

ivDde Deprotection and coupling of MDpr(Boc)-OH. After coupling of Dolavaline-Val-Dil-OH tripeptide, the resin was treated with 2% hydrazine/DMF (1 mL per gram of resin) for 2 hours at RT. Then the resin was washed with DMF (5×1 mL per gram of resin), CH$_2$Cl$_2$ (5×1 mL per gram of resin), ethyl ether (5×1 mL per gram of resin), and dried in vacuo. A solution of Fmoc-MDpr(Boc)-OH (2 equiv), HATU (2 equiv), and DIEA (4 equiv) in DMF (1 mL per gram of resin) was added to the resin and the mixture was shaken for 3 hours at room temperature (RT). Reaction completion was confirmed by negative Kaiser test. The resin was washed with DMF (5×1 mL per gram of resin), CH$_2$Cl$_2$ (5×1 mL per gram of resin), ethyl ether (5×1 mL per gram of resin), and dried in vacuo.

Cleavage off the resin and deprotection. Peptide-containing resin was treated with 20% TFA/CH$_2$Cl$_2$ (2 mL per gram of resin) for 10 min at room temperature, and solution was collected in a round bottom flask. The resin was washed with 20% TFA/CH$_2$Cl$_2$ (2×0.5 mL per gram of resin). Pooled solutions were left at RT for 3 hours. After deprotection, completion was confirmed by LC-MS. Volatiles were removed under reduced pressure on Rotavap, and the final product was purified by reverse phase preparative HPLC. All drug-linkers were obtained with >95% purity by reverse phase HPLC at 215 nm.

Drug-linkers with MA maleimide were prepared in a similar way as described above using α-maleimidoacetic acid-NHS (Molecular Biosciences, Boulder Colo.) instead of MDpr(Boc)-OH.

Drug-linkers with an ethylene diamine (EDA) stretcher were prepared by the procedure similar to the one reported earlier (Bioconjugate Chem. 2008, 19, 1960-1963).

Example 2 Drug Linkers

Drug linkers were synthesized as described above. The general formula was as follows:

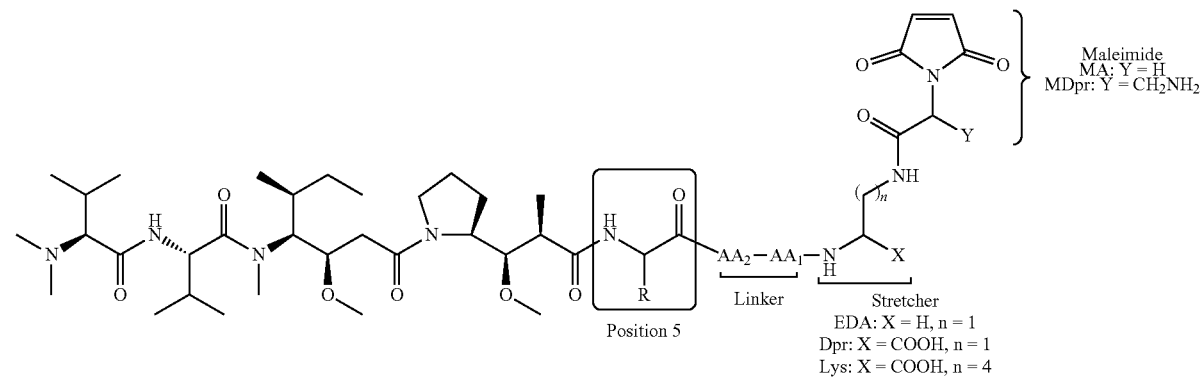

(In this formula, note the designation of AA$_2$ and AA$_1$ is reversed, R corresponds to R$^{12}$.)

The following Table 1 summarizes the syntheses and characterizations of the various drug linkers. In the table, the first column (left) refers to the Compound Number. The second column (left) refers to amino acid at the C-terminus of the auristatin. The third, fourth and fifth columns refer to the components of the linker. In column 3, the amino acid components of the linker are identified. In column 4, additional amino acid and/or non-amino acid components of the linker are identified. In column 5, the composition of the maleimide moiety of the linker is identified. The sixth column refers to the yield of the drug-linker. The seventh and eighth columns refer to the calculated and observed masses of the drug-linkers, as determined by mass spectroscopy. The last column (at right) refers to the MC retention time of ADC's containing the drug linkers as 8 loads (generally determined as described in Example 3).

TABLE 1

| # | Position 5 of the auristatin | Amino Acid(s) | Linker Amino Acid or other stretcher | Maleimide (MA or MDpr) | Yield, % | MS: Calculated (MH)+ | MS: Found, m/z | HIC retention time (min) |
|---|---|---|---|---|---|---|---|---|
| 1 | Phe | none | Dpr | MA | 14 | 969.6 | 969.7 | NT |
| 2 | Phe | Glu | Dpr | MA | 11 | 1098.6 | 1098.8 | NT |
| 3 | Thr | none | Dpr | MA | 7.3 | 923.5 | 923.7 | NT |
| 4 | Thr | Glu | Dpr | MA | 8.1 | 1052.6 | 1052.8 | 5 |
| 5 | Phe | Glu | Dpr | MDpr | 20 | 1127.6 | 1127.4 | NT |
| 6 | Thr | Glu | Dpr | MDpr | 20 | 1081.6 | 1081.7 | 4.5 |
| 7 | Thr | Glu | Lys | MDpr | 36 | 1123.7 | 562.5 Dbl chrgd | 4.6 |
| 8 | Thiazole | Glu | Lys | MDpr | 28 | 1176.6 | 588.9 Dbl chrgd | NT |
| 9 | Phe | Glu | EDA | MDpr | 30 | 1083.6 | 1083.9 | 5.8 |
| 10 | Thr | Glu | EDA | MDPr | 23 | 1037.6 | 1037.8 | NT |
| 11 | Phe | Ile | EDA | MDPr | 25 | 1067.7 | 1067.9 | 6.9 |
| 12 | Thr | Ile | EDA | MDPr | 20 | 1021.7 | 511.5 Dbl chrgd | 5.2 |
| 13 | Thiazole | Glu | EDA | MDPr | 43 | 1090.6 | 1091.6 | 4.9 |
| 14 | Asp | Ala | Lys | MDPr | 70 | 1079.6 | 1079.9 | 4.98 |
| 15 | Glu | Ala | Lys | MDPr | 81 | 1093.6 | 1093.8 | 5.02 |
| 16 | PhosphoThr | Ala | Lys | MDPr | 4.5 | 1145.6 | 1145.9 | 4.81 |
| 17 | Asn | AlaGlu | Dpr | MDPr | 70 | 1165.6 | 1165.5 | 5 |
| 18 | Gln | AlaGlu | Dpr | MDPr | 40 | 1179.7 | 1180.09 | 5.1 |
| 19 | Asp | AlaGlu | Dpr | MDPr | 67 | 1166.6 | 1167.3 | 4.95 |
| 20 | Glu | Alaglu | Dpr | MDPr | 72 | 1180.6 | 1180.96 | 4.98 |
| 21 | hSer | AlaGLu | Dpr | MDPr | 71 | 1152.6 | 1152.7 | 5.1 |
| 22 | ValOH | AlaGlu | Dpr | MDPr | 21 | 1166.7 | 1167.1 | 5.2 |
| 23 | PhosphoThr | AlaGlu | Dpr | MDPr | 13 | 1232.6 | 1232.78 | 4.8 |
| 24 | Pyrazole | Glu | Dpr | MDPr | 73 | 1117.6 | 1117.5 | 5.2 |
| 25 | Triazole | Glu | Dpr | MDPr | 85 | 1118.6 | 1118.7 | 5 |
| 26 | Asn | Glu | Dpr | MDPr | 91 | 1108.6 | 1108.5 | 4.9 |
| 27 | Asp | Glu | Dpr | MDPr | 90 | 1095.6 | 1095.4 | 4.8 |
| 28 | Fur | Glu | Dpr | MDPr | 11 | 1117.6 | 1117.6 | 5.6 |
| 29 | ValOH | Glu | Dpr | MDPr | 22 | 1095.6 | 1095.7 | 5.1 |
| 30 | Ser | Glu | Dpr | MDPr | 86 | 1067.6 | 1068.3 | 4.9 |
| 31 | hSer | Glu | Dpr | MDPr | 68 | 1081.6 | 1081.5 | 4.96 |
| 32 | Thr | IleLeu | Dpr | MDPr | 30-50 | 1178.7 | 1178.8 | 6.1 |
| 33 | Phe | IleLeu | Dpr | MDPr | 30-50 | 1224.7 | 1224.9 | 7.4 |
| 34 | Glu | PheLeu | Dpr | MDPr | 30-50 | 1240.7 | 1241.1 | 5.9 |
| 35 | Thr | LeuPhe | Dpr | MDPr | 30-50 | 1212.7 | 1212.8 | 6.7 |
| 36 | Phe | LeuPhe | Dpr | MDPr | 30-50 | 1258.7 | 1258.9 | 7.8 |
| 37 | Glu | PhePhe | Dpr | MDPr | 30-50 | 1274.7 | 1274.8 | 6.1 |
| 38 | Thr | LysAla | Dpr | MDPr | 30-50 | 1151.7 | 1151.9 | 4.9 |
| 39 | Thr | Lys | Dpr | MDPr | 30-50 | 1080.6 | 1181.1 | 4.8 |
| | | | mc-MMAF | | | | | 7.0 |
| | | | mc-vc-PABC-MMAF | | | | | 8.2 |
| | | | mc-vc-PABC-MMAE | | | | | 9.8 |

Abbreviations:

Ala refers to L-alanine; Asn refers to asparagine; Asp refers to L-aspartate; Gln refers to L-glutamine;
Glu refers to L-glutamate; Ile refers to L-isoleucine; Leu refers to L-leucine; Lys refers to L-lysine; Phe refers to L-phenylalanine; PhosphoThr refers to L-phosphothreonine; Thr refers to L-threonine;
hSer refers to L-hydroxyserine:

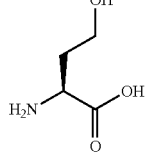

ValOH refers to L-hydroxyvaline:

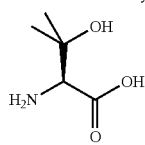

TABLE 1-continued

| | | Linker | | | | | |
|---|---|---|---|---|---|---|---|
| # | Position 5 of the auristatin | Amino Acid(s) | Amino Acid or other stretcher | Maleimide (MA or MDpr) | Yield, % | MS: Calculated (MH)+ | MS: Found, m/z | HIC retention time (min) |

Pyrazole refers to:

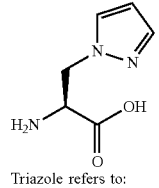

Triazole refers to:

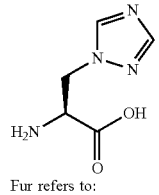

Fur refers to:

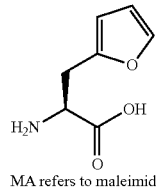

MA refers to maleimido acetyl; Dpr refers to diaminopropionic acid; MDpr refers to maleimido diaminopropionic acid; EDA refers to ethylene diamine; mc-MMAF refers to linker maleimidocaproyl MMAF; mc-vc-PABC-MMAF refers to maleimidocaproyl-valine-citrulline-p-aminobenzyl-carbamoyl MMAF; mc-vc-PABC-MMAF refers to maleimidocaproyl-valine-citrulline-p-aminobenzyl-carbamoyl MMAE.

Example 3 Antibody Drug Conjugates

Preparation of Antibody-Drug Conjugates. Exemplary for h1F6 ADCs.

h1F6 antibody-drug conjugates (ADCs) with eight drugs per antibody were prepared by full reduction of the antibody followed by reaction with the desired drug-linker. The antibody (10 mg/mL) was fully reduced by addition of 10 molar equivalents of tris(2-carboxyethyl)phosphine (TCEP) in phosphate buffered saline (PBS) pH 7.4 (Invitrogen, Carlsbad, Calif.) with 1 mM diethylenetriaminepentaacetic acid (DTPA), followed by incubation at 37° C. for ~1 h. Excess TCEP was removed by 10x dilution with PBS and concentration of the antibody, repeated 2 times using a 30 KD MWCO spin filter (EMD Millipore, Billerica, Mass.). Full reduction of the antibody was confirmed by reversed phase HPLC analysis where the light and heavy chains are completely resolved from unreduced antibody. The drug-linker (10 equivalents) was then added from a stock solution prepared in DMSO (10 mM). The reaction was allowed to stand at room temperature for approximately 2 hours to allow for conjugation and subsequent thiosuccinimide ring hydrolysis (MDpr). The reaction mixture was purified and buffer-exchanged into PBS using PD-10 desalting columns (GE Healthcare, Piscataway, N.J.). The drug/Ab ratio of the final product was estimated by PERP-MS analysis and ranged from 7.8-8.0 drugs/Ab. In addition, each ADC was analyzed by size exclusion chromatography where HMW species ranged from 0.5-2.0%.

Hydrophobic Interaction Chromatography

Analysis of the ADCs was performed using Hydrophobic Interaction Chromatography (HIC), HIC is performed by running a linear gradient from 0-100% Mobile Phase B (MPB) where Mobile Phase A (MPA) consists of 1.5 M ammonium sulfate, 25 mM potassium phosphate, pH 7.0, and MPB consists of 75% 25 mM potassium phosphate, pH 7.0, 25% isopropanol. Separation was achieved using a Tosoh t-Butyl column (TSK-Gel Butyl-NPR 4.6×35 mm, PN: 14947) heated to 25° C. Test articles were prepared by diluting 70 µg of ADC into MPA such that the total salt concentration is greater than or equal to 1.0 M ammonium sulfate at a total volume of 100 µL. Samples were injected at 90 µL, and eluted using a 12 minute gradient. Monitoring at λ=280 nm. ADCs with greater hydrophobicity, or a greater number of drugs per molecule, elute at later retention times.

Figure 4:
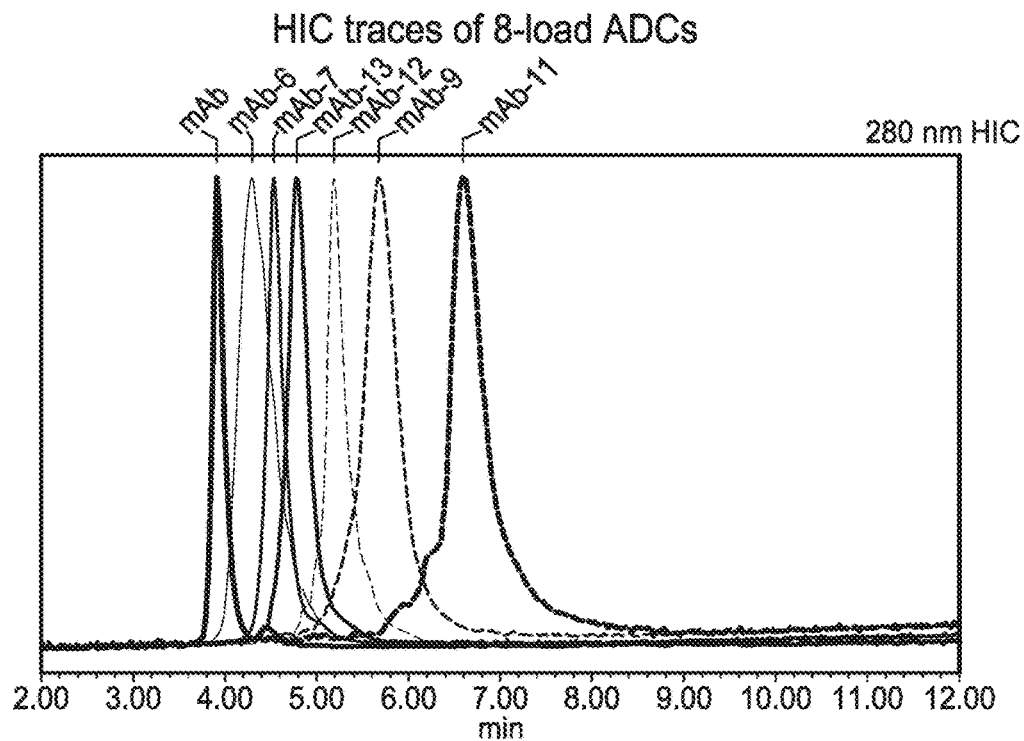
FIG. 4 shows the results of HIC chromatography of antibody drug conjugates.
Figure 5:
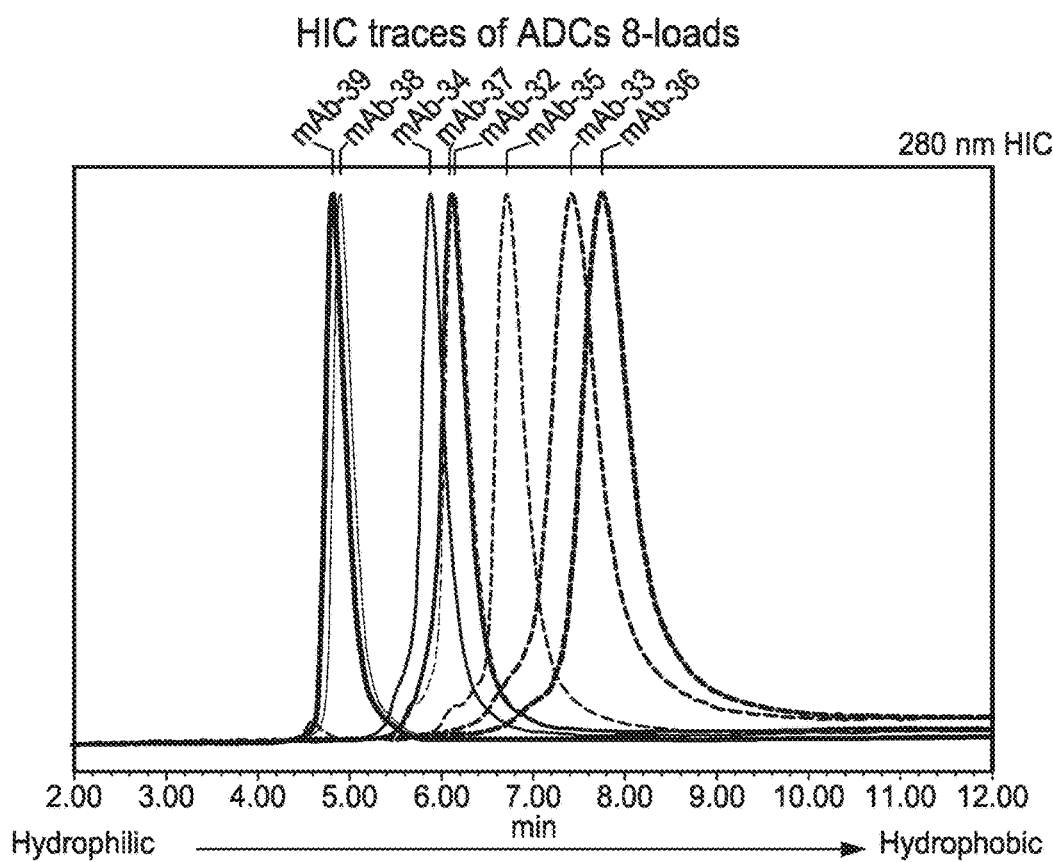
FIG. 5 shows the results of HIC chromatography of antibody drug conjugates.

FIGS. 4 and 5 show the results of HIC analyses of various 8 loaded ADCs, as compared to the parent, unconjugated antibody (h1F6). The ADCs were prepared as described above. The results generally show that increasing the hydrophilicity of the auristatin, in combination with a hydrophilic linker, decreases the apparent hydrophobicity of the conjugate.

The following Table 2 summarizes the compositions of various drug linkers of Table 1 and analyses of the resulting 8-loaded antibody drug conjugates with antibody h1F6. The HIC retention time (HIC RT) was determined as described above. h1F6 ADCs containing the drug linkers MC-vc-PABC-MMAE, MC-vc-PABC-MMAF and MC-MMAF were used as controls.

TABLE 2

| No. | (AA5 of Auristatin) - AA1-AA2-MDpr | HIC RT (min) h1F6 8-loads |
|---|---|---|
| 4967 | (Asp)-Ala-Lys(MDpr) | 4.98 |
| 4968 | (Glu)-Ala-Lys(MDpr) | 5.02 |
| 4969 | (Phospho-Thr)-Ala-Lys(MDpr) | 4.81 |
| 4970 | (Asn)-Ala-Glu-MDpr | 5.0 |
| 4971 | (Gln)-Ala-Glu-MDpr | 5.1 |
| 4972 | (Asp)-Ala-Glu-MDpr | 4.95 |
| 4973 | (Glu)-Ala-Glu-MDpr | 4.98 |
| 4974 | (homoSer)-Ala-Glu-MDpr | 5.1 |
| 4975 | (ValOH)-Ala-Glu-MDpr | 5.2 |
| 4976 | (Phospho-Thr)-Ala-Glu-MDpr | 4.8 |
| 4977 | (Pyrazol)-Glu-MDpr | 5.2 |
| 4978 | (Triazol)-Glu-MDpr | 5.0 |
| 4979 | (Asn)-Glu-MDpr | 4.9 |
| 4980 | (Asp)-Glu-MDpr | 4.8 |
| 4981 | (Furyl)-Glu-MDpr | 5.6 |
| 4982 | (ValOH)-Glu-MDpr | 5.1 |
| 4983 | (Ser)-Glu-MDpr | 4.9 |
| 4984 | (homoSer)-Glu-MDpr | 4.96 |
| 4830 | (Thr)-Glu-MDpr | 4.5 |
| 4808 | (Thr)-Glu-MA | 5.0 |
| 4851 | (Thr)-Glu-Lys(MDpr) | 4.6 |
| 4854 | (Thr)-Glu-EDA-MDpr | NT |
| 4856 | (Thr)-Ile-EDA-MDpr | 5.2 |
| 4853 | (Phe)-Glu-EDA-MDpr | 5.8 |
| 4855 | (Phe)-Ile-EDA-MDpr | 6.9 |
| 4882 | (Thiazole)-Glu-EDA-MDpr | 4.9 |
| 4883 | (Met)-Asn-(D)Lys-EDA-MDpr | 4.8 |
| 1006 | MC-vc-PABC-MMAE | 9.8 |
| 1251 | MC-vc-PABC-MMAF | 8.2 |
| 1269 | MC-MMAF | 7.0 |

Example 4 in Vitro Activity Assays

In vitro cytotoxicity assays were performed generally as described previously (see supra, Activity Assays). Briefly, log phase cultures of cells were collected and cells plated at seeding densities ranging from 500-10,000 cells/well according to pre-determined conditions. After incubating 24 hours to allow surface protein reconstitution, serial dilutions of test conjugates were added and cultures incubated further for 4 days. Assessment of cellular growth and dye reduction to generate $IC_{50}$ values was done using Alamar Blue (Biosource International, Camarillo, Calif.) dye reduction assay. Briefly, a 40% solution (wt/vol) of Alamar Blue was freshly prepared in complete media just before cultures were added. Ninety-two hours after drug exposure, Alamar Blue solution was added to cells to constitute 10% culture volume. Cells were incubated for 4 h, and dye reduction was measured on a Fusion HT fluorescent plate reader (Packard Instruments, Meriden, Conn.).

786-0 renal and Caki-1 clear cell renal cancer cell lines were used. These cell lines expressed approximately 190,000 and 135,000 human CD70 molecules per cell, respectively. The drug linkers attached to the h1F6 antibody are described in Tables 1 and 2. Referring to the following Tables 3A-C, the h1F6 ADCs have an average drug loading of 8 drugs/antibody, unless otherwise indicated. The hydrophilic h1F6 ADCs tested showed activity ($IC_{50}$ values) comparable to, or better than, the control, h1F6-mcMMAF (1269), in these studies.

TABLE 3A

IC50 summary for auristatin-based ADCs

| ADCs | Dr/Ab | Caki-1 | 786-O |
|---|---|---|---|
| h1F6-1 | 4 | 21 | 21 |
|  | 8 | 8 | 7 |
| h1F6-2 | 4 | 17 | 21 |
|  | 8 | 7 | 7 |
| h1F6-3 | 4 | 27 | 28 |
|  | 8 | 13 | 13 |
| h1F6-4 | 4 | 20 | 21 |
|  | 8 | 11 | 9 |
| h1F6-5 | 4 | 39 | 32 |
|  | 8 | 22 | 19 |
| h1F6-6 | 4 | 23 | 26 |
|  | 8 | 7 | 9 |
| h1F6-7 | 4 | 80 | 10 |
|  | 8 | 24 | 4 |
| h1F6-8 | 8 | 19 | 4 |
| h1F6-9 | 8 | 21 | 3 |
| h1F6-10 | 8 | 57 | 5 |
| h1F6-11 | 8 | 9 | 1 |
| h1F6-12 | 8 | 12 | 4 |
| h1F6-13 | 8 | 60 | 5 |

DR/Ab refers to the average drug loading; IC50s are reported in ng/mL.

TABLE 3B

IC50 summary for auristatin-based ADCs

| Auristatin-based ADCs | Dr/Ab | 786-O | Caki-1 |
|---|---|---|---|
| h1F6-14 | 8.0 | 6 | 19 |
| h1F6-15 | 8.0 | 6 | 16 |
| h1F6-16 | 8.0 | 9 | 12 |
| h1F6-17 | 8.0 | 6 | 14 |
| h1F6-18 | 8.0 | 8 | 18 |
| h1F6-19 | 8.0 | 7 | 20 |
| h1F6-20 | 8.0 | 7 | 9 |
| h1F6-21 | 8.0 | 12 | 22 |
| h1F6-22 | 8.0 | 24 | 21 |
| h1F6-23 | 8.0 | 11 | 18 |
| h1F6-24 | 8.0 | 11 | 33 |
| h1F6-25 | 8.0 | 14 | 34 |
| h1F6-26 | 8.0 | 9 | 19 |
| h1F6-27 | 8.0 | 7 | 15 |
| h1F6-28 | 8.0 | 7 | 21 |
| h1F6-29 | 8.0 | 31 | 33 |
| h1F6-30 | 8.0 | 12 | 18 |
| h1F6-31 | 8.0 | 13 | 20 |
| h1F6-6 | 8.0 | 11 | 12 |
| h1F6-mcMMAF | 4.0 | 44 | 42 |

TABLE 3C

IC50s for with h1F6-ADCs, ng/mL

| Auristatin-based ADCs | Dr/Ab | 786-O Clear RCC | Caki-1 Clear RCC |
|---|---|---|---|
| h1F6-32 | 8.0 | 5 | 3 |
| h1F6-33 | 8.0 | 0.8 | 0.8 |
| h1F6-34 | 8.0 | 3 | 6 |
| h1F6-35 | 8.0 | 3 | 3 |
| h1F6-36 | 8.0 | 0.7 | 0.5 |
| h1F6-37 | 8.0 | 4 | 4 |
| h1F6-38 | 8.0 | 3 | 3 |
| h1F6-39 | 8.0 | 3 | 3 |
| h1F6-6 | 8.0 | 7 | 5 |
| h1F6-mcMMAF | 4.0 | 34 | 12 |

Example 5—Pharmacokinetics Studies

Antibody and ADC Radiolabeling

Pharmocokinetic (PK) experiments were performed using radiolabeled antibody or ADC. PK test articles were radiolabeled using the following procedure. To a solution of antibody or ADC in 500 mM potassium phosphate (pH 8.0) and 500 mM sodium chloride was added 55 µCi N-succinimidyl propionate, [propionate-2,3-3H]-(Moravek Biochemicals, Cat. No.: MT 919, 80 Ci/mmol, 1 mCi/mL, 9:1 hexane:ethyl acetate solution) per mg of antibody or ADC. The resulting mixture was vortexed and left at room temperature for 2 hours. The mixture was centrifuged at 4,000×g for 5 minutes and the lower aqueous layer was removed and split into Amicon Ultra-15 Centrifugal Filter Units (Millipore, Cat. No.: UFC903024, 30 kDa MWCO). Unconjugated radioactivity was removed by 4 rounds of dilution and centrifugation at 4,000×g. The resulting products were filtered through sterile 0.22 µm Ultrafree-MC Centrifugal Filter Units (Millipore, Cat. No.: UFC30GV0S) and the final antibody or ADC concentration was measured spectrophotometrically. The specific activity (µCi/mg) of each product was determined by liquid scintillation counting.

Pharmacokinetic Studies

The pharmacokinetic properties of an unconjugated antibody and various ADCs of the that antibody (drug loading of 8) were examined in several rodent models. In each experiment, 3 mg of radiolabeled antibody or ADC per kg of animal weight were injected via the tail vein. Each test article was dosed once in 3 replicate animals. Blood was drawn into K2 EDTA tubes via the saphenous vein or by cardiac puncture for terminal bleeds at various time points. Plasma was isolated by centrifugation for 10 minutes at 10,000×g. A 10 µL of sample of plasma from each time point was added to 4 mL Ecoscint-A liquid scintillation cocktail (National Diagnostics) and the total radioactivity was measured by liquid scintillation counting. The resulting disintegrations per minute values were converted to µCi and the specific activity of the radiolabeled test articles was used to calculate the concentration of antibody or ADC remaining in the plasma at each time point.

Figure 2:
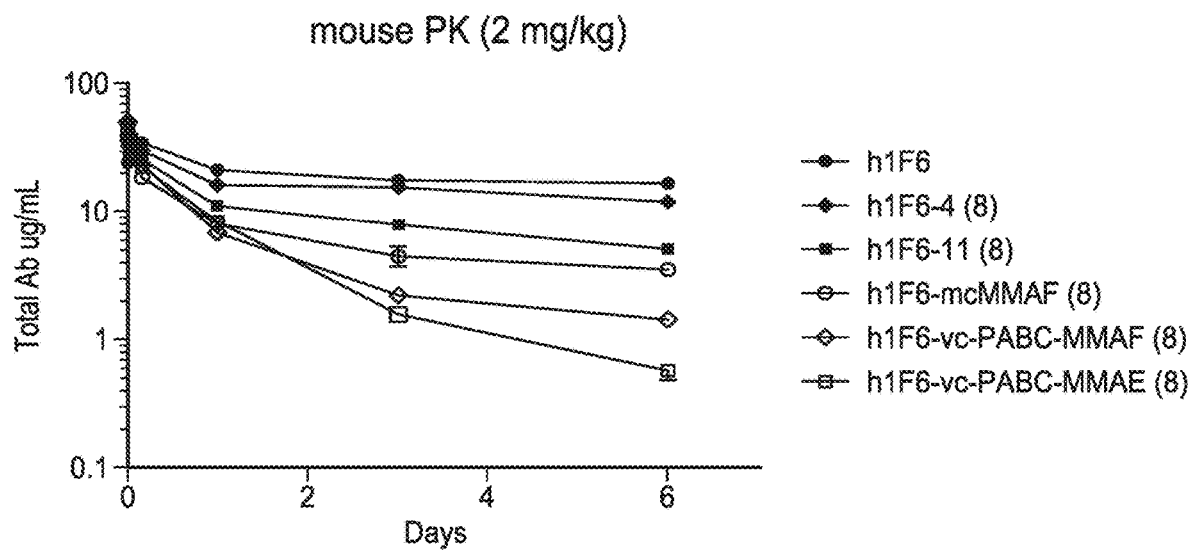
FIG. 2 shows the results of a mouse study comparing the pharmacokinetic stability of an unconjugated antibody, two hydrophilic ADCs and three control ADCs. The ADCs are shown in order from top to bottom.

Referring to FIG. 2, pharmacokinetics properties of h1F6 and two hydrophilic ADCs thereof were compared to the properties three control ADCs. The hydrophilic ADCs were h1F6-4 (8-loaded (auristatin-T)-Glu-Dpr-MA)$_8$-h1F6) and h1F6-11 ((auristatin F)-Ile-EDA-MDpr)$_8$-h1F6). The results show that the hydrophilic ADCs exhibited improved pharmacokinetic stability over the course of this mouse study. The hydrophilic auristatin with an auristatin-T exhibited stability close to that of the unconjugated antibody. The hydrophilic design of ADC h1F6-11 exhibited improved pK stability compared to the controls, two of which include a monomethyl form of the same auristatin (auristatin F vs monomethyl auristatin F).

Figure 3:
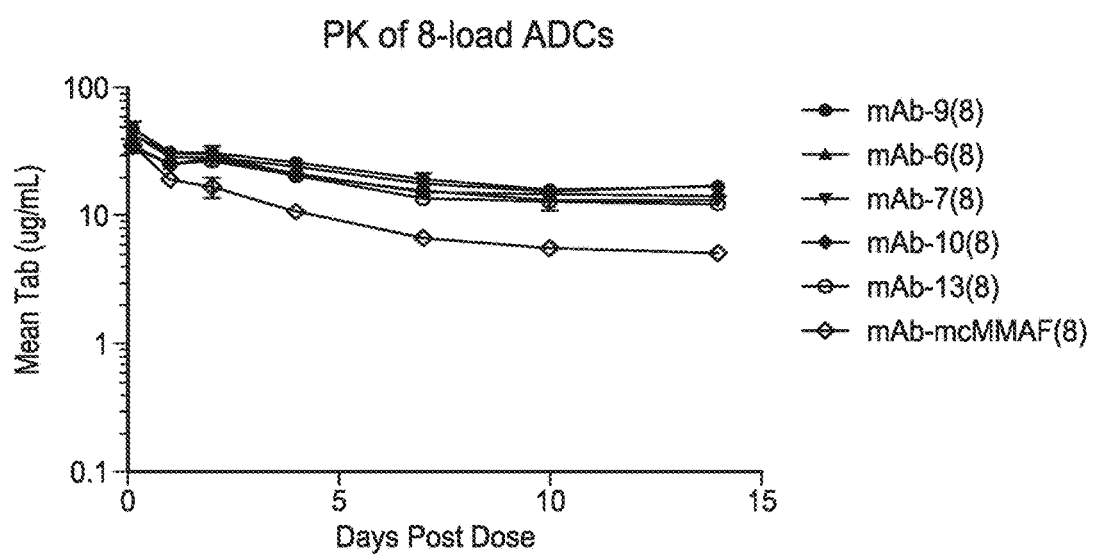
FIG. 3 shows the results of a mouse study comparing the pharmacokinetic stability of five hydrophilic ADCs and a control ADC.

Referring to FIG. 3, pharmacokinetics properties of hydrophilic conjugates of another monoclonal antibody were compared to the properties of a control conjugate, mAb-mcMMAF. All of the ADCs had an average drug loading of 8. Each of the hydrophilic ADCs exhibited improved pharmacokinetic stability, as compared to the control ADC.

Two hydrophilic ADCs thereof were compared to the properties three control ADCs. The hydrophilic ADCs were h1F6-8 (8-loaded (auristatin-thiazole)-Glu-Lys-MDpr)$_8$-h1F6) and h1F6-11 ((auristatin F)-Ile-EDA-MDpr)$_8$-h1F6). The results show that the hydrophilic ADCs exhibited improved pharmacokinetic stability over the course of this mouse study. In particular, the hydrophilic design of h1F6-11 exhibited improved stability compared to the controls, two of which include a monomethyl form of the same auristatin (auristatin. F vs monomethyl auristatin F).

Example 6 ® In Vivo Therapy Experiments

786-O cells were obtained from American Type Culture Collection (ATCC, Manassas, Va.) and propagated in culture conditions recommended by ATCC. To establish 786-0 tumors, 5×10$^6$ cells were implanted into the right flank of athymic nu/nu female donor mice (Harlan, Indianapolis, Ind.). When donor tumors were approximately 500 mm$^3$, mice were euthanized and tumors were aseptically excised and ~0.5×0.5 mm fragments were loaded into a sterilized 13-gauge trocar for implantation into nu/nu mice. When tumors reached ~100 mm$^3$, mice were randomly allocated to treatment groups.

To establish DOHH2 tumors, 5×10$^6$ cells were implanted into the right flank of C.B.-17 SCID) mice (Harlan, Indianapolis, Ind.). When tumors were approximately ~100 mm$^3$, mice were randomly allocated to treatment groups.

Experimental groups were treated via intraperitoneal injection with compounds at the dose and schedule indicated or alternatively left untreated. Tumors were measured periodically and volumes were calculated using the formula $V=((L \times W^2)/2)$. Animals were euthanized when tumors reached the volume of 1000 mm$^3$ or at the end of the study, whichever came first.

Tumor quadrupling times were chosen as time to endpoint (TTE), which was determined by using the non-liner regression analysis for exponential growth of each individual tumor growth data sets from each experimental animal. The median tumor quadrupling time was calculated based on the tumor volume at the beginning of treatment. Animals that did not reach the endpoint were assigned a T value equal to the last day of the study.

Statistical analysis was conducted using Prism (GraphPad) software for Windows. The Logrank test of the TTE was used to analyze the significance of the differences between the two groups, with differences deemed significant at $0.01 \leq P \leq 0.05$, and highly significant at $P \leq 0.01$.

Figure 6:
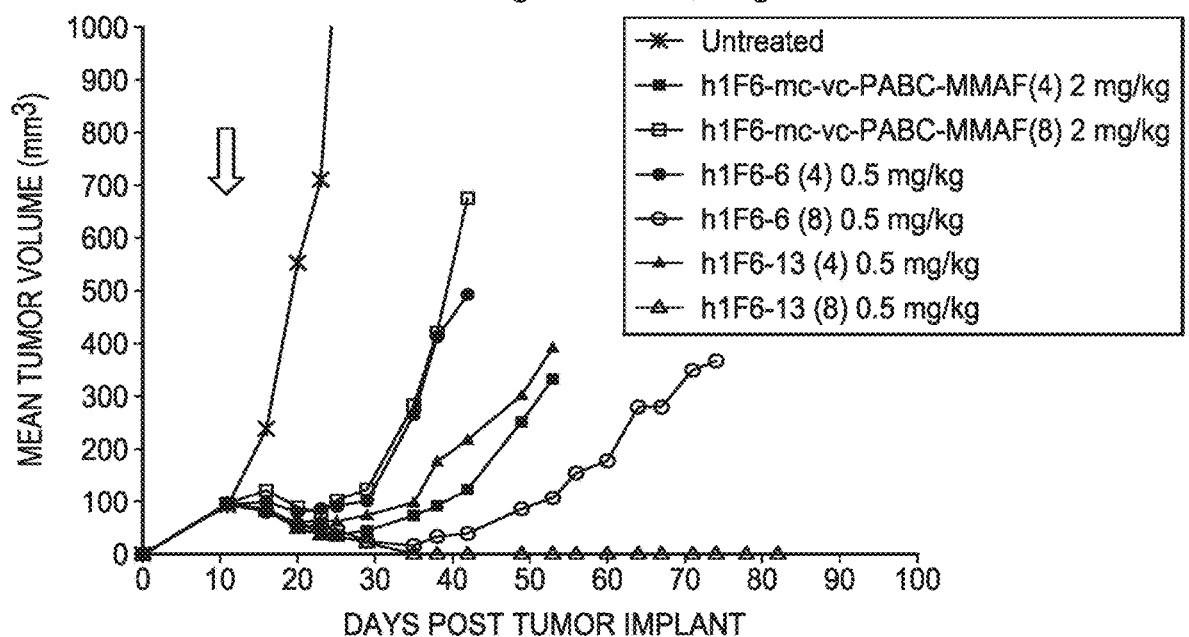
FIG. 6 shows the results of mouse xenograft studies comparing the activities of 4-loaded and 8-loaded ADCs.
Figure 7:
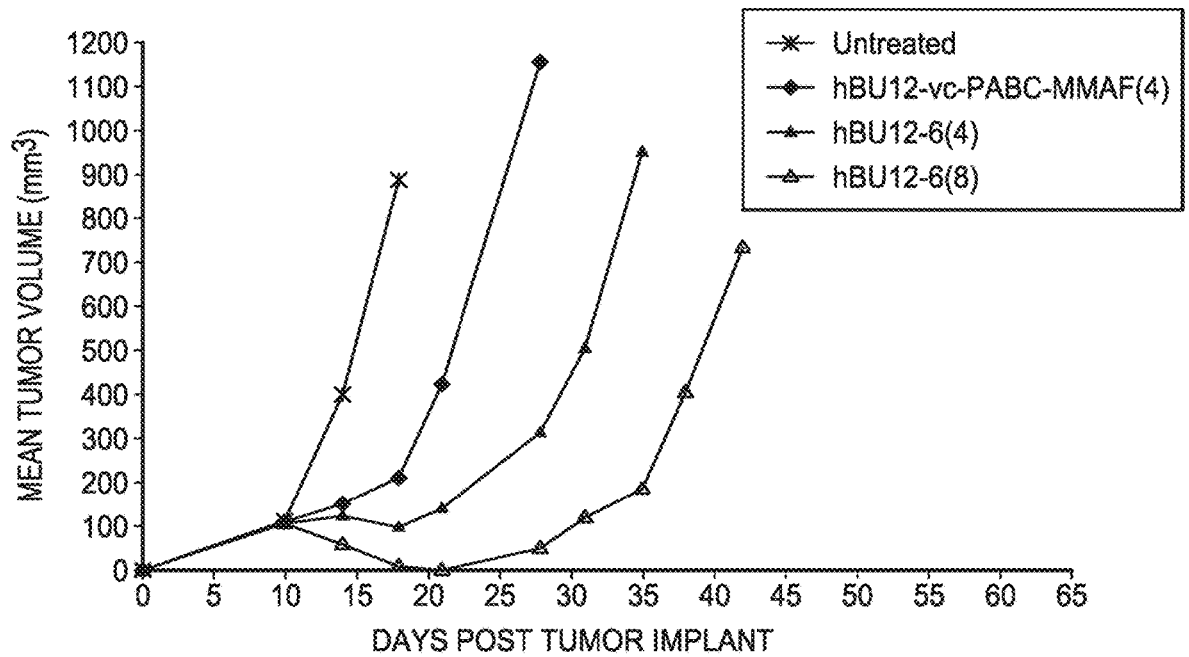
FIG. 7 shows the results of mouse xenograft studies comparing the activities of 4-loaded acid 8-loaded ADCs.

Referring to FIG. 6, the activity of 4-loaded and 8-loaded ADCs (4d/Ab and 8d/Ab, respectively) were tested in single dose, mouse xenograft studies. First, referring to the control, h1F6-mc-vc-PABC-MMAF, the 4-loaded ADC gave better activity than the 8-loaded ADC. In contrast, 8-loaded ADCs of hydrophilic h1F6-6 (auristatin T-Glu-Dpr-MDPr) and h1F6-13 (auristatin thiazole-Glu-EDA-MDPr) both exhibited greater activity than the 4-loaded counterparts, Referring to FIG. 7, the activity of different 4-loaded and 8-loaded ADCs were tested in single dose, mouse xenograft studies. Again in this model, the 8-loaded hydrophilic ADC of hBU12-6 (auristatin T-Glu-Dpr-MDPr) exhibited greater activity than its 4-loaded counterpart.

Figure 8:
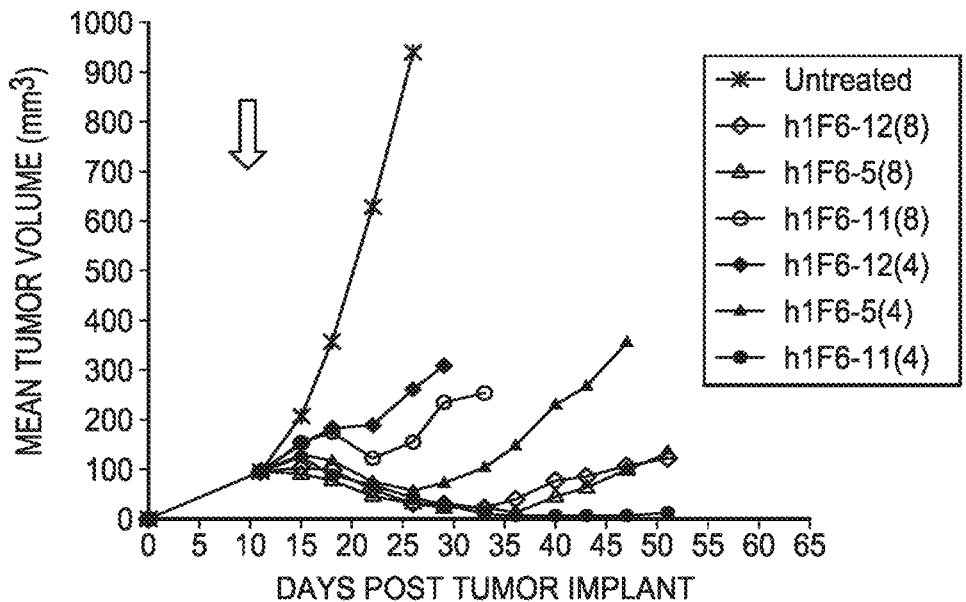
FIG. 8 shows the results of mouse xenograft studies comparing the activities of 4-loaded and 8-loaded ADCs.

Referring to FIG. 8, the activity of various 4-loaded and 8-loaded ADCs were tested in single dose, mouse xenograft studies. In this model, 8-loaded ADCs of h1F6-12 (auristatin T-Ile-EDA-MDPr) and h1F6-5 (auristatin F-Glu-Dpr-MDPr) both exhibited greater activity than the 4-loaded counterparts. 8-loaded ADC h1F6-11 (auristatin F-Ile-EDA-MDPr) exhibited the opposite trend.

Figure 9:
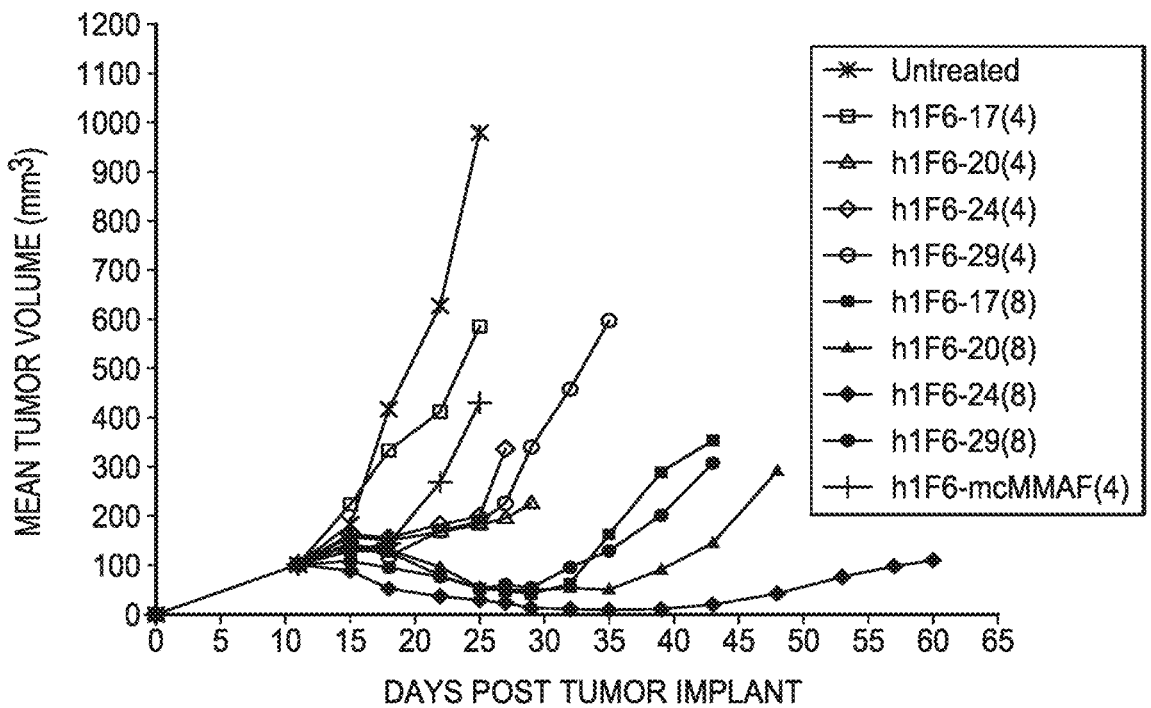
FIG. 9 shows the results of mouse xenograft studies comparing the activities of 4-loaded and 8-loaded ADCs.

Referring to FIG. 9, the activity of various 4-loaded and 8-loaded ADCs were tested in single dose, mouse xenograft studies. In this model, the 8-loaded ADCs of h1F6-17, h1F6-20, h1F6-24 and h1F6-29 exhibited greater activity than the 4-loaded counterparts.

What is claimed is:

1. A Drug-Linker Compound having the formula:

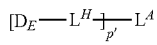

or a pharmaceutically acceptable salt or solvate thereof, wherein:

$L^A$ is a Ligand attachment component;

$L^H$ is an optionally branched hydrophilic linker having the formula:

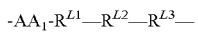

wherein:

$AA_1$ is a hydrophilic amino acid that forms a cleavable bond with the $D_E$ unit to which it is attached;

$R^{L1}$ is optional and is selected from a hydrophilic amino acid or an optionally substituted alkylene, which may share an atom with $L^A$ when $R^{L1}$ is present and $R^{L2}$ and $R^{L3}$ are not present;

$R^{L2}$ is optional and is selected from a hydrophilic amino acid and an optionally substituted alkylene, which may share an atom with $L^A$ when $R^{L2}$ is present and $R^{L3}$ is not present; and $R^{L3}$ is optional and is selected from a hydrophilic amino acid and an optionally substituted alkylene, which may share an atom with $L^A$ when $R^{L3}$ is present;

the subscript p' is an integer of from 1 to 4; and each $D_E$ is an auristatin (Aur) having the formula:

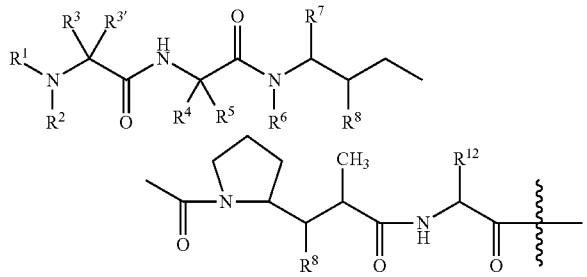

or a pharmaceutically acceptable salt or solvate thereof, wherein:

$R^1$ and $R^2$ each are independently selected from the group consisting of hydrogen (H) and optionally substituted —$C_1$-$C_8$ alkyl; with the proviso that both $R^1$ and $R^2$ are not H, unless both of $R^3$ and $R^{3'}$ are not H;

$R^3$ is selected from the group consisting of H and optionally substituted —$C_1$-$C_8$ alkyl;

$R^{3'}$ is selected from the group consisting of H and optionally substituted —$C_1$-$C_8$ alkyl, and at least one of $R^3$ and $R^{3'}$ is not H;

$R^4$ is selected from the group consisting of H and optionally substituted —$C_1$-$C_8$ alkyl;

$R^5$ is selected from the group consisting of H and optionally substituted —$C_1$-$C_8$ alkyl;

or $R^4$ and $R^5$ jointly form a carbocyclic ring and have the formula —$(CR^aR^b)_n$—, wherein $R^a$ and $R^b$ are independently selected from the group consisting of H and optionally substituted —$C_1$-$C_8$ alkyl and n is selected from the group consisting of 2, 3, 4, 5 and 6;

$R^6$ is selected from the group consisting of H and optionally substituted —$C_1$-$C_8$ alkyl;

$R^7$ is selected from the group consisting of H and optionally substituted —$C_1$-$C_8$ alkyl;

each $R^8$ is independently selected from the group consisting of H, —OH, optionally substituted —$C_1$-$C_8$ alkyl, and optionally substituted —O—($C_1$-$C_8$ alkyl);

$R^{12}$ is selected from the side chains of the group consisting of threonine, serine, asparagine, aspartic acid, glutamine, glutamic acid, homoserine, hydroxyvaline, furyl alanine, threonine($PO_3H_2$), pyrazolyl alanine, triazolyl alanine and thiazolyl alanine; or a pharmaceutically acceptable salt or solvate thereof;

wherein the left and right lines of $L^H$ indicate covalent attachments to the $D_E$ unit and $L^A$, respectively.

2. The Compound of claim 1, wherein $L^H$ comprises a modified peptide, wherein at least one of $R^{L1}$, $R^{L2}$ and $R^{L3}$ is an amino acid that is covalently linked by a reactive group on its side chain to an adjacent group; or a pharmaceutically acceptable salt or solvate thereof.

3. The Compound of claim 1, wherein $R^{12}$ is the side chain of L-threonine; or a pharmaceutically acceptable salt or solvate thereof.

4. The Compound of claim 1, wherein $L^A$ comprises a maleimide; or a pharmaceutically acceptable salt or solvate thereof.

5. The Compound of claim 1, or a pharmaceutically acceptable salt or solvate thereof, wherein:

(a) $AA_1$ is a hydrophilic amino acid selected from the group consisting of Glycine and L forms of Aspartate, Glutamate, Asparagine, Glutamine, Histidine, Lysine, Arginine, Serine and Alanine;

(b) when $R^{L1}$ is present, it is selected from the group consisting of:

Glycine; L or D forms of Aspartate, Glutamate, Asparagine, Glutamine, Histidine, Lysine, Arginine, Serine and Alanine; —NH—CH($R^a$)—CO—; and —NH—CH(COOH)—$R^b$—; wherein $R^a$ is selected from —$CH_2NH_2$, —$CH_2CH_2NH_2$, —$CH_2CH_2CH_2NH_2$, —$CH_2CH_2CH_2CH_2NH_2$, —$CH_2CH_2OH$, —$CH_2CH_2CH_2CO_2H$, —$CH_2CH_2CH_2CO_2H$ and —$CH_2CH_2CH_2CH_2CO_2H$; and $R^b$ is selected from —$CH_2NH$—, —$CH_2CH_2NH$—, —$CH_2CH_2CH_2NH$—, —$CH_2CH_2CH_2CH_2NH$—, —$CH_2CH_2CO$—, —$CH_2CH_2CH_2CO$—, —$CH_2CH_2CH_2CO$— and —$CH_2CH_2CH_2CH_2CO$—; and a $C_1$-$C_6$ alkylene, optionally substituted with 1-4 substituents selected from —NH—, —C(O)—, —COOH, —N($C_1$-$C_3$ alkyl)-, —$NH_2$ or —NH($C_1$-$C_3$ alkyl);

(c) when $R^{L2}$ is present, it is selected from the group consisting of:

Glycine; L or D forms of Aspartate, Glutamate, Asparagine, Glutamine, Histidine, Lysine, Arginine, Serine and Alanine; —NH—CH($R^a$)—CO—; and —NH—CH(COOH)—$R^b$—; wherein $R^a$ is selected from —$CH_2NH_2$, —$CH_2CH_2NH_2$, —$CH_2CH_2CH_2NH_2$, —$CH_2CH_2CH_2CH_2NH_2$, —$CH_2CH_2OH$, —$CH_2CH_2CH_2CO_2H$, —$CH_2CH_2CH_2CO_2H$ and —$CH_2CH_2CH_2CH_2CO_2H$; and $R^b$ is selected from —$CH_2NH$—, —$CH_2CH_2NH$—, —$CH_2CH_2CH_2NH$—, —$CH_2CH_2CH_2CH_2NH$—, —$CH_2CH_2CO$—, —$CH_2CH_2CH_2CO$—, —$CH_2CH_2CH_2CO$— and —$CH_2CH_2CH_2CH_2CO$—; and a $C_1$-$C_6$ alkylene, optionally substituted with 1-4 substituents selected from —NH—, —C(O)—, —COOH, —N($C_1$-$C_3$ alkyl)-, —$NH_2$ or —NH($C_1$-$C_3$ alkyl); and
(d) when $R^{L3}$ is present, it is selected from the group consisting of:

Glycine; L or D forms of Aspartate, Glutamate, Asparagine, Glutamine, Histidine, Lysine, Arginine, Serine and Alanine; —NH—CH($R^a$)—CO—; and —NH—CH(COOH)—$R^b$—; wherein $R^a$ is selected from —$CH_2NH_2$, —$CH_2CH_2NH_2$, —$CH_2CH_2CH_2NH_2$, —$CH_2CH_2CH_2CH_2NH_2$, —$CH_2CH_2OH$, —$CH_2CH_2CH_2CO_2H$, —$CH_2CH_2CH_2CO_2H$ and —$CH_2CH_2CH_2CH_2CO_2H$; and $R^b$ is selected from —$CH_2NH$—, —$CH_2CH_2NH$—, —$CH_2CH_2CH_2NH$—, —$CH_2CH_2CH_2CH_2NH$—, —$CH_2CH_2CO$—, —$CH_2CH_2CH_2CO$—, —$CH_2CH_2CH_2CO$— and —$CH_2CH_2CH_2CH_2CO$—; and an $C_1$-$C_6$ alkylene, optionally substituted with 1-4 substituents selected from —NH—, —C(O)—, —COOH, —N($C_1$-$C_3$ alkyl)-, —$NH_2$ or —NH($C_1$-$C_3$ alkyl).

6. The Compound of claim 1, or a pharmaceutically acceptable salt or solvate thereof, wherein:
(a) $AA_1$ is present and $R^{L1}$, $R^{L2}$ and $R^{L3}$ are absent;
(b) $AA_1$ is present, $R^{L1}$ is present and $R^{L2}$ and $R^{L3}$ are absent;
(c) $AA_1$ is present, $R^{L1}$ is present, $R^{L2}$ is present and $R^{L3}$ is absent;
(d) $AA_1$ is present, $R^{L1}$ is present, $R^{L2}$ is present and $R^{L3}$ is present;
(e) $AA_1$ is present and at least one of $R^{L1}$, $R^{L2}$ and $R^{L3}$ is present and is an optionally substituted alkylene;
(f) $AA_1$ is Glutamate and at least one of $R^{L1}$, $R^{L2}$ and $R^{L3}$ is present and is an optionally substituted alkylene;
(g) $AA_1$ is Glutamate, $R^{L1}$ is a hydrophilic amino acid and at least one of $R^{L2}$ and $R^{L3}$ is present and is an optionally substituted alkylene;
(h) $AA_1$ and $R^{L1}$ are hydrophilic amino acids and at least one of $R^{L2}$ and $R^{L3}$ is present and is an optionally substituted alkylene;
(i) $AA_1$ is a hydrophilic amino acid and $R^{L1}$ and optionally $R^{L2}$ are an optionally substituted alkylene;
(j) $AA_1$ is present and at least one of $R^{L1}$, $R^{L2}$ and $R^{L3}$ is present and is an optionally substituted alkylene selected from the group consisting of ethylenediamine, —NH—CH(COOH)—$CH_2$—NH— and —CO—CH($CH_2NH_2$)—;
(k) $AA_1$ is Glutamate, $R^{L1}$ is a hydrophilic amino acid and at least one of $R^{L2}$ and $R^{L3}$ is present and is an optionally substituted alkylene selected from the group consisting of ethylenediamine, —NH—CH(COOH)—$CH_2$—NH— and —CO—CH($CH_2NH_2$)—;
(l) $AA_1$ and $R^{L1}$ are hydrophilic amino acids and at least one of $R^{L2}$ and $R^{L3}$ is present and is an optionally substituted alkylene selected from the group consisting of ethylenediamine, —NH—CH(COOH)—$CH_2$—NH— and —CO—CH($CH_2NH_2$)—; or
(m) $AA_1$ is a hydrophilic amino acid and $R^{L1}$ and optionally $R^{L2}$ are an optionally substituted alkylene selected from the group consisting of ethylenediamine, —NH—CH(COOH)—$CH_2$—NH— and —CO—CH($CH_2NH_2$)—.

7. The Compound of claim 1, wherein -$L^H$- has the formula:

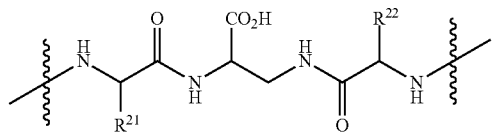

or a pharmaceutically acceptable salt or solvate thereof, wherein:

$R^{21}$ is selected from the group consisting of —$CH_2NH_2$, —$CH_2CH_2NH_2$, —$CH_2OH$, —$CH_2CH_2OH$, —$CH_2CO_2H$, —$CH_2CH_2CO_2H$, —$CH_2CH_2CH_2CO_2H$, and —$CH_2CH_2CH_2CH_2CO_2H$; and $R^{22}$ is selected from the group consisting of —$CH_2NH_2$, —$CH_2CH_2NH_2$, —$CH_2OH$; and the left and right wavy lines indicate attachment to $D_E$ and $L^A$, respectively.

8. The Compound of claim 1, wherein -$L^H$- has the formula:

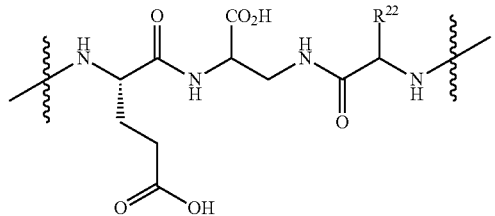

or a pharmaceutically acceptable salt or solvate thereof, wherein $R^{22}$ is selected from —$CH_2NH_2$, —$CH_2CH_2NH_2$, —$CH_2OH$, and —$CH_2CH_2OH$; and the left and right wavy lines indicate attachments to $D_E$ and $L^A$, respectively.

9. The Compound of claim 1, or a pharmaceutically acceptable salt or solvate thereof, wherein -$L^H$- has the formula selected from the group consisting of:

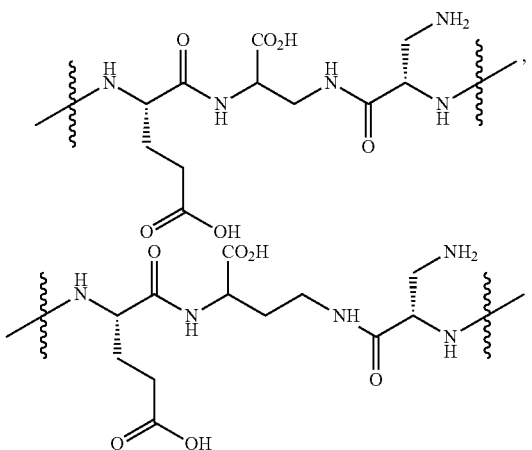

-continued

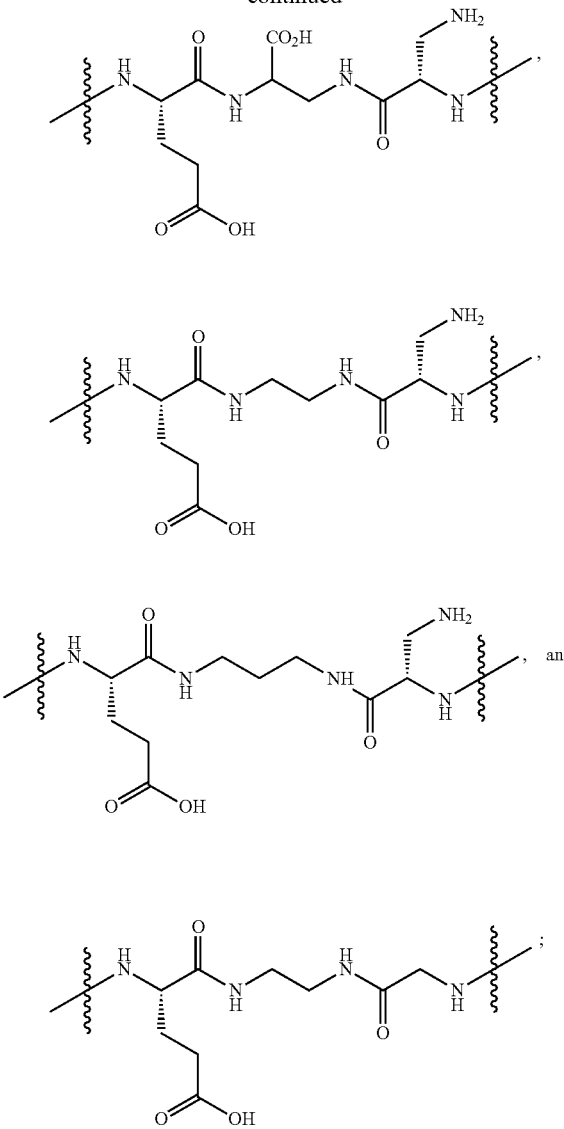

wherein the left and right wavy lines indicate attachments to $D_E$ and $L^A$, respectively.

10. The Compound of claim 1, or a pharmaceutically acceptable salt or solvate thereof, wherein the Compound comprises the formula:

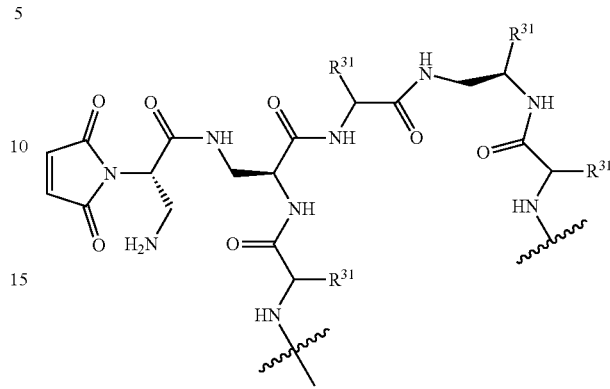

wherein each $R^{31}$ is independently selected from the group consisting of —$CH_2NH_2$, —$CH_2CH_2NH_2$, —$CH_2OH$, —$CH_2CH_2OH$, —$CH_2CO_2H$, —$CH_2CH_2CO_2H$, —$CH_2CH_2CH_2CO_2H$, and —$CH_2CH_2CH_2CH_2CO_2H$; and each of the bars indicates attachment to a $D_E$ unit.

11. The Compound of claim 1, or a pharmaceutically acceptable salt or solvate thereof, wherein the Compound comprises the formula:

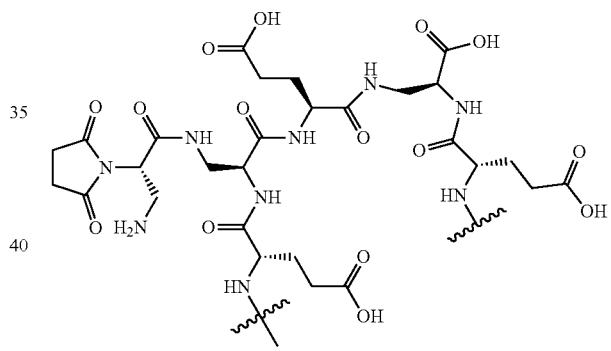

wherein each of the bars indicates attachment to a $D_E$ unit.

* * * * *